United States Patent
Sato et al.

(10) Patent No.: US 11,787,860 B2
(45) Date of Patent: Oct. 17, 2023

(54) ANTI-CD47 ANTIBODIES AND USES THEREOF

(71) Applicant: CELGENE CORPORATION, Summit, NJ (US)

(72) Inventors: Aaron Sato, Burlingame, CA (US); Ryan Stafford, Foster City, CA (US); Junhao Yang, Palo Alto, CA (US)

(73) Assignee: CELGENE CORPORATION, Summit, NJ (US)

(*) Notice: Subject to any disclaimer, the term of this patent is extended or adjusted under 35 U.S.C. 154(b) by 256 days.

(21) Appl. No.: 16/949,459

(22) Filed: Oct. 29, 2020

(65) Prior Publication Data

US 2021/0054070 A1   Feb. 25, 2021

Related U.S. Application Data

(62) Division of application No. 15/541,003, filed as application No. PCT/US2015/067642 on Dec. 28, 2015, now Pat. No. 10,870,699.

(60) Provisional application No. 62/098,291, filed on Dec. 30, 2014.

(51) Int. Cl.
| | |
|---|---|
| *A61K 39/395* | (2006.01) |
| *C07K 16/28* | (2006.01) |
| *C12P 21/02* | (2006.01) |
| *A61K 45/06* | (2006.01) |
| *A61K 39/00* | (2006.01) |

(52) U.S. Cl.
CPC .... *C07K 16/2803* (2013.01); *A61K 39/39541* (2013.01); *A61K 45/06* (2013.01); *C12P 21/02* (2013.01); *A61K 2039/505* (2013.01); *C07K 2317/14* (2013.01); *C07K 2317/24* (2013.01); *C07K 2317/56* (2013.01); *C07K 2317/73* (2013.01); *C07K 2317/732* (2013.01); *C07K 2317/734* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 8,758,750 B2 | 6/2014 | Weissman et al. |
| 9,045,541 B2 | 6/2015 | Eckelman et al. |
| 10,870,699 B2 | 12/2020 | Sato et al. |
| 2009/0060924 A1 | 3/2009 | Korytko et al. |
| 2013/0195867 A1 | 8/2013 | Hoerr et al. |
| 2013/0224188 A1 | 8/2013 | Eckelmna et al. |
| 2014/0140989 A1 | 5/2014 | Eckelman et al. |
| 2017/0081407 A1 | 3/2017 | Grosveld et al. |
| 2017/0369572 A1 | 12/2017 | Sato et al. |
| 2018/0171014 A1 | 6/2018 | Manning et al. |
| 2021/0054070 A1 | 2/2021 | Sato et al. |

FOREIGN PATENT DOCUMENTS

| | | |
|---|---|---|
| WO | 2009/131453 A1 | 10/2009 |
| WO | 2011004847 A1 | 1/2011 |
| WO | 2013/119714 A1 | 2/2013 |
| WO | 2014123580 A1 | 8/2014 |
| WO | 2014172631 A1 | 10/2014 |
| WO | 2016/109415 A1 | 7/2016 |

OTHER PUBLICATIONS

Almagro & Fransson, Frontiers in Bioscience 2008; 13:1619-33 (Year: 2008).*
De Genst et al., Dev Comp Immunol 2006; 30:187-98 (Year: 2006).*
Yoshinaga et al., J. Biochem 2008; 143:593-601 (Year: 2008).*
Yin et al. (Mabs. Mar.-Apr. 2012 4(2), pp. 217-225; cited on IDS filed Oct. 29, 2020) (Year: 2012).*
Groff, D., et al, "Engineering toward a bacterial "endoplasmic reticulum" for the rapid expression of immunoglobulin proteins", MABS, US, (Feb. 11, 2014), vol. 6, No. 3, ISSN 1942-0870, pp. 671-678.
Yang, W. C., et al, "Simplifying and streamlining *Escherichia coli*-based cell-free protein synthesis", Biotechnology Progress, (Jan. 1, 2012), ISSN 8756-7938.
Yin, G., et al., Aglycosylated antibodies and antibody fragments produced in a scalable in vitro transcriptiontranslation system, ISSN: 1942-0862 (Print) 1942-0870 (Online) Journal homepage: https://www.tandfonline.com/loi/kmab20.
International Search Report for International Application No. PCT/US2015/067642, dated Mar. 17, 2016.
Yin, et al, "Aglycosylated Antibodies and Antibody Fragments Produced in a Scalable in Vitro Transcription-Translation System", InMAbs, vol. 4, No. 2, pp. 217-225, Mar. 1, 2012.
Almagro & Fransson, Humanization of antibodies, Frontiers in Bioscience 2008; 13:1619-33.
De Genst et al., Antibody repertoire development in camelids, Dev Comp Immunol 2006; 30:187-98.
Yoshinaga et al., Ig L-chain shuffling for affinity maturation of phage library-derived human anti-human MCP-1 antibody blocking its chemotactic activity, J. Biochem 2008; 143:593-601.
Mendelsohn, N.J. et al., Elimination of Antibodies to Recombinant Enzyme in Pompe's Disease, N Engl J Med, in 2009, vol. 360, pp. 194-195.
Kekow, J. et al., Long Persistence of Anti-Drug Antibodies in AdalimumabTreated RA Patients, Arthritis Rheumatol, In 2016, vol. 68, No. S10, Abstract No. 2550.
Hassan, R. et al., Pretreatment with Rituximab Does Not Inhibit the Human Immune Response against the Immunogenic Protein LMB-1, Clin Cancer Res, in 2004, vol. 10, pp. 16-18.

(Continued)

*Primary Examiner* — Meera Natarajan
(74) *Attorney, Agent, or Firm* — Debora Plehn-Dujowich; Eckert Seamans Cherin & Mellott, LLC

(57) ABSTRACT

Provided herein are compositions, methods and uses involving antibodies that specifically bind to human CD47. Also provided are uses and methods, such as therapeutic methods, diagnostic methods, and methods of making such antibodies.

21 Claims, 9 Drawing Sheets
Specification includes a Sequence Listing.

(56) References Cited

OTHER PUBLICATIONS

Liu et al in "Pre-Clinical Development of a Humanized Anti-CD47 Antibody with Anti-Cancer Therapeutic Potential"; PLoS One. Sep. 21, 2015; 10(9).

Sehn et al. "Introduction of Combined CHOP Plus Rituximab Therapy Dramatically Improved Outcome of Diffuse Large B-Cell Lymphoma in British Columbia" J Clin Oneal. Aug. 1, 2005;23(22):5027-33.

Smith, M. "Rituximab (monoclonal anti-CD20 antibody): mechanisms of action and resistance". Oncogene (2003) 22, 7359-7368.

Onrust et al. "Rituximab". Drugs Jul. 1999; 58 (1): 79-88.

Chao, M. P., et al., Anti-CD47 antibody synergizes with rituximab to promote phagocytosis and eradicate non-Hodgkin lymphoma, Cell, Sep. 3, 2010, pp._ 699-713, vol._ 142, No._ 5.

Friedberg, J_ W., et al., Combination immunotherapy iwth tituximab and interleukin 2 in patients with relapsed or efractory follicular non-Hodgkin's lymphoma, British Journal of Haematology, Jan. 1, 2002, pp._ 828-834, vol._ 117.

Zhang, A-H, et al., Effect of B-cell depletion using anti-CD20 therapy on inhibitory antibody formation to human FVIII in hemophilia A mice, BLOOD, Feb. 17, 2011, pp._ 2223-2226, vol. 117, No._ 7.

Dierickx, D., et al., Anti-CD20 monoclonal antibodies and their use in adult autoimmune hematological disorders, American Journal of Hematology, Feb. 15, 2011, pp._ 278-291, vol._ 86, No._ 3.

Zhang, H., et al., Characterization of a Novel Humanized Anti-CD20 Antibody with Potent Anti-Tumor Activity Against Non-Hodgkin's Lymphoma, Jan. 1, 2013, pp._ 645-654, vol. 32, No. 3.

\* cited by examiner ated on Oct. 29,

ANTI-CD47 ANTIBODIES AND USES THEREOF

This application is a divisional of U.S. patent application Ser. No. 15/541,003, filed Jun. 29, 2017 as a 35 U.S.C. § 371 national phase application from International Application No. PCT/US2015/067642, filed Dec. 28, 2015, which claims benefit of U.S. Provisional Patent Application No. 62/098, 291, filed Dec. 30, 2014, the disclosure of each of which prior applications are incorporated by reference herein in their entirety.

REFERENCE TO SEQUENCE LISTING SUBMITTED ELECTRONICALLY

This application incorporates by reference a Sequence Listing submitted with this application as text file entitled 298068-00352 Sequence_Listing.txt created on Oct. 29, 2020 and having a size of 87,719 bytes.

1. FIELD

Provided herein are antibodies (anti-CD47 antibodies) which specifically bind to CD47 and compositions comprising such antibodies, including pharmaceutical compositions, diagnostic compositions and kits. Also provided are methods of using anti-CD74 antibodies for therapeutic and diagnostic purposes, and methods for making such anti-CD47 antibodies, for example with cell-free (CF) systems.

2. BACKGROUND

CD47, also known as integrin-associated protein (IAP), ovarian cancer antigen OA3, Rh-related antigen and MER6, is a multi-spanning transmembrane receptor belonging to the immunoglobulin superfamily. SIRPα (signal-regulatory-protein α) expressed on macrophages interacts with CD47, and this interaction negatively controls effector function of innate immune cells such as host cell phagocytosis. CD47 expression and/or activity have been implicated in a number of diseases and disorders. Accordingly, there exists a need for therapies that target CD47, as well as better methods for making such therapies.

3. SUMMARY

In one aspect, provided herein are antibodies (e.g., monoclonal antibodies), including antigen-binding fragments thereof, which specifically bind to CD47 (e.g., human CD47), such as an extracelluar domain (ECD) of CD47. In specific aspects, such anti-CD47 antibody blocks CD47 binding to SIRPα, promotes phagocytosis, has reduced or no Fc effector function (e.g., binding to FcγR, ADCC, or CDC) and/or has little or no agglutination (e.g., hemagglutination) activity.

In a specific aspect, provided herein is a monoclonal anti-CD47 antibody which specifically binds to human CD47, wherein the anti-CD47 antibody is a variant of a parental antibody, and wherein the anti-CD47 antibody when produced using a cell-free (CF) expression system has a higher antibody expression titer or yield compared to the parental antibody when produced in the CF expression system. In a particular aspect, anti-CD47 antibodies provided herein which are expressed in a CF system, are aglycosylated.

In one aspect, provided herein is a monoclonal anti-CD47 antibody which specifically binds to human CD47 (e.g., SEQ ID NO: 38 or 39), wherein the anti-CD47 antibody, when produced using a cell-free system, has a higher antibody expression titer or yield compared to a parental antibody produced using the cell-free system. In specific aspects, the the anti-CD47 antibody expression titer or yield is higher by at least 1 fold, at least 2 fold, or at least 3 fold compared to the parental antibody. In specific aspects, the the anti-CD47 antibody expression titer or yield is higher by at least 25%, 50%, 75%, or 100% compared to the parental antibody. In particular aspects, such anti-CD47 antibody is a humanized antibody. In specific aspects, the cell-free system comprises using S30 cell-free extract. In particular aspects, such cell-free system comprises prokaryotic disulfide bond isomerase DsbC. In certain aspects, such anti-CD47 antibody is an IgG$_1$ antibody. In certain aspects, such anti-CD47 antibody is an IgG$_4$ antibody. In certain aspects, such anti-CD47 antibody is an IgG$_4$ antibody comprising a S228P amino acid substitution according to the EU numbering index. In certain aspects, such anti-CD47 antibody is an IgG$_4$ antibody comprising a S228P and L235E amino acid substitutions according to the EU numbering index.

In specific aspects, such parental antibody of an anti-CD47 antibody provided herein comprises a heavy chain variable region comprising the amino acid sequence of SEQ ID NO: 1. In certain aspects, such parental antibody comprises a light chain variable region comprising the amino acid sequence of SEQ ID NO: 12. In particular aspects, such parental antibody comprises a heavy chain comprising the amino acid sequence of SEQ ID NO: 2, 3 or 4.

In particular aspects, an anti-CD47 antibody provided herein comprises (i) a heavy chain variable region comprising complementarity determining region (CDR) 1, 2, and 3 of antibody 2A1; and (ii) a light chain variable region comprising CDR1, CDR2, and CDR3 of antibody 2A1.

In specific aspects, an anti-CD47 antibody provided herein comprises (i) a heavy chain variable region comprising complementarity determining region (CDR) 1, 2, and 3 comprising amino acid sequences GFNIKDYYLH (SEQ ID NO: 14), WIDPDQGDTE (SEQ ID NO: 15), and NAAYGSSSYPMDY (SEQ ID NO: 16), respectively; and (ii) a light chain variable region comprising CDR1, CDR2, and CDR3 comprising amino acid sequences KASQDIHR-YLS (SEQ ID NO: 17), RANRLVS (SEQ ID NO: 18), and LQYDEFPYT (SEQ ID NO: 19), respectively.

In particular aspects, provided herein are anti-CD47 antibody comprising one or more amino acid modifications (e.g., amino acid substitutions) relative to a parental antibody. In specific aspects, such one or more amino acid substitutions is in the framework region of the heavy chain variable region or light chain variable region. In specific aspects, such anti-CD47 antibody comprises 13 or 14 amino acid modifications (e.g., amino acid substitutions) in the framework region of the heavy chain variable region. In particular aspects, such anti-CD47 antibody comprises 1 to 15 amino acid modifications (e.g., amino acid substitutions) in the framework region of the heavy chain variable region. In particular aspects, such amino acid modifications are conservative amino acid substitutions.

In specific aspects, provided herein is a monoclonal anti-CD47 antibody which specifically binds to CD47 (e.g., human CD47 such as SEQ ID NO: 38 or 39) and comprises a heavy chain variable region (V$_H$) comprising the amino acid sequence: X$_1$QX$_2$QLVQSGAEVKKX$_3$GX$_4$SVKVS CKASGFNIKDYYLHWVRQAPGQX$_5$LEWMGWIDPD QGDTEYAQKX$_6$QX$_7$RVTX$_8$TX$_9$DX$_{10}$SX$_{11}$STAYMEL X$_{12}$SLRSX$_{13}$DTAX$_{14}$YYCNAAYGSSSYPMDYWGQG TTVTV (SEQ ID NO: 20), wherein the amino acid at position $X_1$ is any amino acid or there is no amino acid at position $X_1$, and wherein the amino acid at each of positions $X_2$-$X_{14}$ is any amino acid. In certain aspects, $X_1$ is M or there is no amino acid at position $X_1$, $X_2$ is an amino acid with hydrophobic side chains such as M or V, $X_3$ is T or P, $X_4$ is S or A, $X_5$ is an amino acid having aliphatic side chains such as A or G, $X_6$ is F or L, $X_7$ is D or G, $X_8$ is an amino acid with hydrophobic side chains such as I or M, $X_9$ is R or T, $X_{10}$ is R or T, $X_{11}$ is M or T, $X_{12}$ is S or R, $X_{13}$ is a negatively charged amino acid such as E or D, and $X_{14}$ is an amino acid with hydrophobic side chains such as M or V. In particular aspects, the $V_H$ of an anti-CD47 antibody provided herein comprises the amino acid sequence of SEQ ID NO: 21. In certain aspects, the $V_H$ of an anti-CD47 antibody provided herein comprises the amino acid sequence of SEQ ID NO: 22. In specific aspects, an anti-CD47 antibody provided herein comprises a heavy chain comprising the amino acid sequence of SEQ ID NO: 5. In particular aspects, an anti-CD47 antibody provided herein comprises a heavy chain comprising the amino acid sequence of SEQ ID NO: 6. In certain aspects, an anti-CD47 antibody provided herein comprises a heavy chain comprising the amino acid sequence of SEQ ID NO: 7. In particular aspects, an anti-CD47 antibody provided herein comprises a heavy chain comprising the amino acid sequence of SEQ ID NO: 8. In specific aspects, an anti-CD47 antibody provided herein comprises a heavy chain comprising the amino acid sequence of SEQ ID NO: 9. In certain aspects, an anti-CD47 antibody provided herein comprises a heavy chain comprising the amino acid sequence of SEQ ID NO: 10. In particular aspects, an anti-CD47 antibody provided herein comprises a heavy chain comprising the amino acid sequence of SEQ ID NO: 11.

In specific aspects, an anti-CD47 antibody provided herein comprises a light chain comprising the amino acid sequence of SEQ ID NO: 13 or SEQ ID NO: 13 without amino acid M at the N-terminus.

In specific aspects, provided herein is a monoclonal anti-CD47 antibody, which specifically binds to CD47 (e.g., human CD47 such as SEQ ID NO: 38 or 39), wherein the anti-CD47 antibody does not cause or promote substantial red blood cell depletion, anemia, or both red blood cell depletion and anemia after administration. In certain aspects, such anti-CD47 antibody does not cause or promote substantial platelet depletion after administration. In particular aspects, such anti-CD47 antibody does not cause or promote substantial agglutination of cells after administration. In specific aspects, such anti-CD47 antibody does not cause or promote substantial hemagglutination of red blood cells after administration. In certain aspects, such anti-CD47 antibody inhibits (e.g., inhibits by at least about 10%, 20%, 30%, 40%, 50%, 60%, 70%, 80%, 90%, or 100%) CD47 from interacting with signal-regulatory-protein α (SIRPα). In particular aspects, such anti-CD47 antibody promotes phagocytosis, such as macrophage-mediated phagocytosis of a CD47-expressing cell. In certain aspects, such anti-CD47 antibody provided herein does not cause or promote a significant level of effector function. In certain aspects, an anti-CD47 antibody provided herein, when expressed using a cell-free system, exhibits lower (e.g., lower by at least about 10%, 20%, 30%, 40%, 50%, 60%, 70%, 80%, 90%) binding affinity, or does not bind, to an FcγR compared to when expressed using CHO cells. In particular aspects, such lower binding affinity is at least 1 log lower or at least 2 log lower. In certain aspects, the FcγR is FcγRI, FcγRIIA R131, FcγRIIA H131, FcγRIIB, or FcγRIIIA V158.

In particular aspects, an anti-CD47 antibody provided herein is aglycosylated or has less (e.g., at least about 10%, 20%, 30%, 40%, 50%, 60%, 70%, 80%, 90% less) glycosylation when expressed using the cell free system compared to when expressed in CHO cells.

In specific aspects, provided herein is a monoclonal anti-CD47 antibody, which specifically binds to CD47 (e.g., human CD47 such as SEQ ID NO: 38 or 39), wherein the anti-CD47 antibody (i) promotes phagocytosis such as macrophage-mediated phagocytosis of a CD47-expressing cell; (ii) does not cause or promote a significant level of hemagglutination of red blood cells after administration; (iii) does not cause or promote a significant level of ADCC or CDC; and/or (iv) exhibits lower (e.g., lower by at least about 10%, 20%, 30%, 40%, 50%, 60%, 70%, 80%, 90%) binding affinity, or does not bind, to an FcγR compared to when expressed using CHO cells or compared to a parental antibody.

In certain aspects, an anti-CD47 antibody provided herein is a bispecific antibody. In particular aspects, an anti-CD47 antibody provided herein is conjugated to an agent. In certain aspects, the agent is a label or a toxin.

In particular aspects, provided herein is a pharmaceutical composition comprising an effective amount of an anti-CD47 antibody provided herein or an antigen-binding fragment thereof. In specific aspects, the pharmaceutical composition provided herein further comprising a pharmaceutically acceptable carrier.

In specific aspects, provided herein is a polynucleotide comprising a nucleotide sequence encoding a VH chain region, a VL chain region, or both a VL chain region and a VH chain region, of an anti-CD47 antibody described herein. In particular aspects, provided herein is a polynucleotide comprising a nucleotide sequence encoding a heavy chain, a light chain, or both heavy chain and a light chain of an anti-CD47 antibody described herein. In particular aspects, such polynucleotide comprises a nucleotide sequence of any one of SEQ ID NOs: 26-32 encoding a heavy chain. In specific aspects, such polynucleotide comprises a nucleotide sequence of SEQ ID NO: 33 encoding a light chain.

In particular aspects, provided herein is a population of polynucleotides comprising (i) a first polynucleotide comprising nucleotide sequences encoding a VH or a heavy chain of an anti-CD47 antibody described herein, and (ii) a second polypeptide comprising nucleotide sequences encoding a VL or a light chain of an anti-CD47 antibody described herein. In certain aspects, such first polynucleotide is operably linked to a first promoter, and such second polynucleotide is operably linked to a second promoter.

In particular aspects, provided herein is a vector comprising one or more polynucleotides described herein.

In specific aspects, provided herein is a population of vectors comprising (i) a first vector comprising nucleotide sequences encoding a VH or a heavy chain of an anti-CD47 antibody described herein, and (ii) a second vector comprising nucleotide sequences encoding a VL or a light chain of an anti-CD47 antibody described herein.

In particular aspects, provided herein is a composition for cell-free protein expression comprising a cell-free extract and one or more polynucleotides or vectors described herein. In specific aspects, the composition further comprising S30 cell-free extract. In particular aspects, the composition provided herein further comprises prokaryotic disulfide bond isomerase DsbC.

In specific aspects, provided herein is a method of treating cancer, wherein the method comprises administering an anti-CD47 antibody described herein to a subject in need thereof in an amount sufficient to treat the cancer in the subject.

In particular aspects, provided herein is a method of alleviating a symptom of a cancer, the method comprising administering an anti-CD47 antibody described herein to a subject in need thereof in an amount sufficient to alleviate one or more symptoms of the cancer in the subject.

In specific aspects, such method provided herein further comprises administering radiation or chemotherapy.

In specific aspects, such method provided herein further comprises administering another anti-cancer agent.

In specific aspects of the methods provided herein, the cancer is a hematological cancer. In a particular aspect, the cancer is a solid cancer. In a certain aspect, the cancer is multiple myeloma, non-Hodgkin's lymphoma, acute myeloid leukemia (AML), breast cancer, bladder cancer, non-small cell lung cancer/carcinoma, hepatocellular carcinoma (HCC), sarcoma, or head and neck cancer.

In particular aspects, provided herein is an isolated cell comprising one or more polynucleotides or vectors described herein.

In specific aspects, provided herein is an isolated cell comprising a population of polynucleotides or vectors described herein.

In specific aspects, provided herein is an isolated cell producing an anti-CD47 antibody or antigen-binding fragment described herein.

In particular aspects, provided herein is a population of host cells comprising (i) a first host cell comprising a polynucleotide comprising nucleotide sequences encoding a VH or a heavy chain of an anti-CD47 antibody described herein, and (ii) a second host cell comprising a polynucleotide comprising nucleotide sequences encoding a VL or a light chain of an anti-CD47 antibody described herein.

In particular aspects, provided herein is a method of making an anti-CD47 antibody comprising expressing an anti-CD47 antibody described herein with a composition for cell-free protein expression described herein. In a certain aspect, such method further comprises purifying the anti-CD47 antibody.

In specific aspects, provided herein is a method of making an anti-CD47 antibody comprising expressing the anti-CD47 antibody with a cell described herein. In a certain aspect, such method further comprises purifying the anti-CD47 antibody.

4. BRIEF DESCRIPTION OF THE FIGURES

5. DETAILED DESCRIPTION

Figure 1A:
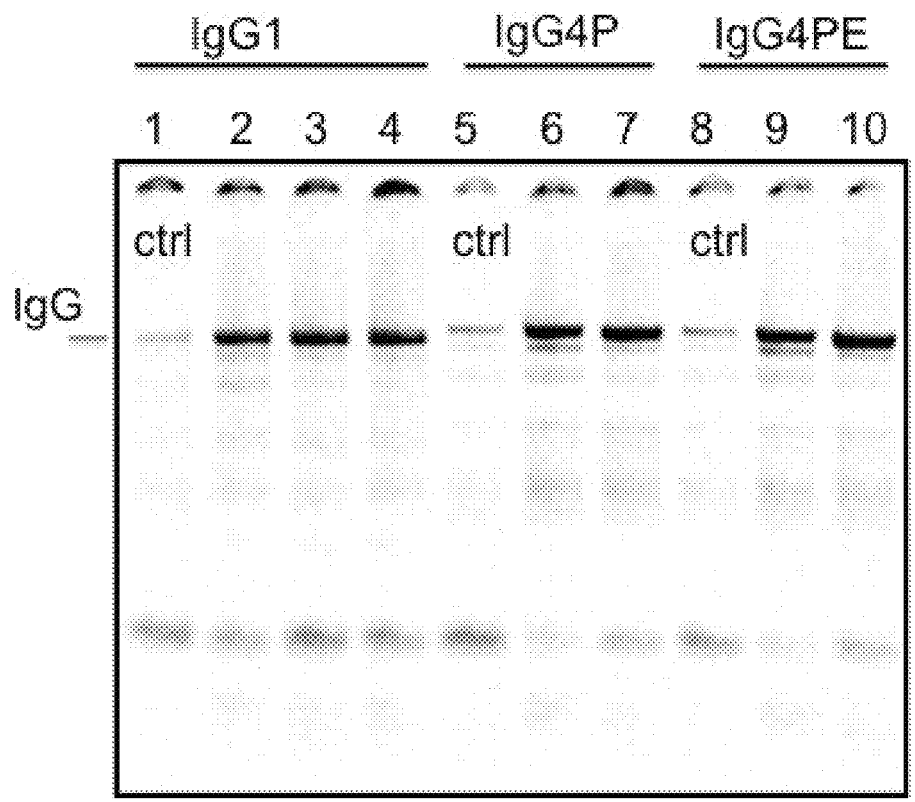
FIG. 1A depicts the autoradiogram of anti-CD47 antibodies expressed with a cell-free (CF) system. Samples 1-10 correspond to CF-expressed anti-CD47 IgG1 (1), IgG1-5m (2), IgG1-13m (3), IgG1-13mZ (4), IgG4P (5), IgG4P-5m (6), IgG4P-13m (7), IgG4PE (8), IgG4PE-5m (9), and IgG4PE-13m (10) antibodies, respectively.

In one aspect, provided herein are antibodies (e.g., monoclonal antibodies), and antigen-binding fragments thereof, that specifically bind to CD47 (e.g., human CD47). In specific aspects, such anti-CD47 antibody blocks CD47 binding to SIRPα, promotes phagocytosis, has reduced or no Fc effector function (e.g., binding to FcγR, ADCC, or CDC) and/or has little or no agglutination (e.g., hemagglutination) activity.

In a specific aspect, provided herein is a monoclonal anti-CD47 antibody which specifically binds to human CD47, wherein the anti-CD47 antibody is a variant of a parental antibody, and wherein the anti-CD47 antibody when produced using a cell-free (CF) expression system has a higher antibody expression titer or yield compared to the parental antibody when expressed in the CF system. In a particular aspect, anti-CD47 antibodies provided herein which are expressed in a CF system, are aglycosylated.

As used herein, the terms "CD47" or "integrin-associated protein" or "IAP" or "ovarian cancer antigen" or "OA3" or "Rh-related antigen" or "MER6" can be used interchangeably and refer to a multi-spanning transmembrane receptor belonging to the immunoglobulin superfamily. The amino acid sequence of an exemplary human CD47 is provided below (GenBank Accession No. Q08722.1 (GI:1171879), incorporated herein by reference). The signal sequence (amino acids 1-18) is underlined.

```
                                        (SEQ ID NO: 38)
  1  MWPLVAALLL GSACCGSAQL LFNKTKSVEF TFCNDTVVIP

CFVTNMEAQN TTEVYVKWKF

61  KGRDIYTFDG ALNKSTVPTD FSSAKIEVSQ LLKGDASLKM

DKSDAVSHTG NYTCEVTELT

121  REGETIIELK YRVVSWFSPN ENILIVIFPI FAILLFWGQF

GIKTLKYRSG GMDEKTIALL

181  VAGLVITVIV IVGAILFVPG EYSLKNATGL GLIVTSTGIL

ILLHYYVFST AIGLTSFVIA

241  ILVIQVIAYI LAVVGLSLCI AACIPMHGPL LISGLSILAL

AQLLGLVYMK FVASNQKTIQ

301  PPRKAVEEPL NAFKESKGMM NDE
```

For clarity, the amino acid sequence of an exemplary human CD47 excluding the signal sequence is provided below.

```
                                                   (SEQ ID NO: 39)
  1  QLLFNKTKSV EFTFCNDTVV IPCFVTNMEA QNTTEVYVKW

KFKGRDIYTF DGALNKSTVP

61  TDFSSAKIEV SQLLKGDASL KMDKSDAVSH TGNYTCEVTE

LTREGETIIE LKYRVVSWFS

121  PNENILIVIF PIFAILLFWG QFGIKTLKYR SGGMDEKTIA

LLVAGLVITV IVIVGAILFV

181  PGEYSLKNAT GLGLIVTSTG ILILLHYYVF STAIGLTSFV

IAILVIQVIA YILAVVGLSL

241  CIAACIPMHG PLLISGLSIL ALAQLLGLVY MKFVASNQKT

IQPPRKAVEE PLNAFKESKG

301  MMNDE
```

The terms red blood cell(s) and erythrocyte(s) are synonymous and used interchangeably herein.

The term agglutination refers to cellular clumping, while the term hemagglutination refers to clumping of a specific subset of cells, i.e., red blood cells. Thus, hemagglutination is a type of agglutination.

5.1 Antibodies

In a specific aspect, provided herein are antibodies which specifically bind to CD47 (e.g., human CD47). In particular aspects, provided herein are anti-CD47 antibodies comprising modifications in one or more amino acid residues (e.g., 5-13 amino acid substitutions in the framework region of the heavy chain variable region) that surprisingly allow for better production in a cell-free (CF) expression system than the parental antibody without the modifications. In certain aspects, such anti-CD47 antibodies inhibit SIRPα interaction with CD47, are aglycosylated, promote phagocytosis, either in vivo or in vitro or both, have anti-tumor activity (e.g., without promoting agglutination, such as hemagglutination), and/or have low or no Fc effector function (e.g., binding to an FcγR, ADCC, or CDC).

In certain embodiments, antibodies or antigen-binding fragments described herein can comprise sequences that do not naturally exist within the antibody germline repertoire of an animal or mammal (e.g., human) in vivo.

As used herein and unless otherwise specified, the terms "about" or "approximately" mean within plus or minus 10% of a given value or range. In instances where an integer is required, the terms mean within plus or minus 10% of a given value or range, rounded either up or down to the nearest integer.

As used herein, the terms "antibody" and "immunoglobulin" and "Ig" are terms of art and can be used interchangeably herein and refer to a molecule with an antigen binding site that specifically binds an antigen.

Antibodies can include, for example, monoclonal antibodies, recombinantly produced antibodies, monospecific antibodies, multispecific antibodies (including bispecific antibodies), human antibodies, humanized antibodies, murine antibodies (e.g., mouse or rat antibodies), chimeric antibodies, synthetic antibodies, and tetrameric antibodies comprising two heavy chain and two light chain molecules. In specific embodiments, antibodies can include, but are not limited to an antibody light chain monomer, an antibody heavy chain monomer, an antibody light chain dimer, an antibody heavy chain dimer, an antibody light chain-antibody heavy chain pair, intrabodies, heteroconjugate antibodies, single domain antibodies, and monovalent antibodies. In a specific embodiment, antibodies can include antigen-binding fragments or epitope binding fragments such as, but not limited to, single chain antibodies or single-chain Fvs (scFv) (e.g., including monospecific, bispecific, etc.), camelized antibodies, affybodies, Fab fragments, F(ab') fragments, F(ab')$_2$ fragments, and disulfide-linked Fvs (sdFv). In certain embodiments, antibodies described herein refer to polyclonal antibody populations.

Antibodies can be of any type (e.g., IgG, IgE, IgM, IgD, IgA or IgY), any class, (e.g., IgG$_1$, IgG$_2$, IgG$_3$, IgG$_4$, IgA$_1$ or IgA$_2$), or any subclass (e.g., IgG$_{2a}$ or IgG$_{2b}$) of immunoglobulin molecule. In certain embodiments, antibodies described herein are IgG antibodies, or a class (e.g., human IgG$_1$, IgG$_2$, IgG$_3$ or IgG$_4$) or subclass thereof. In certain embodiments, antibodies described herein are IgG$_1$ antibodies (e.g., human IgG$_1$) or a subclass thereof. In certain embodiments, IgG$_1$ antibodies described herein comprise one or more amino acid substitutions and/or deletions in the constant region. In certain embodiments, antibodies described herein are IgG$_4$ antibodies (e.g., human IgG$_4$) or a subclass thereof. In certain embodiments, IgG$_4$ antibodies described herein comprise one or more amino acid substitutions and/or deletions in the constant region.

As used herein, an "antigen" is a moiety or molecule that contains an epitope to which an antibody can specifically bind. As such, an antigen is also specifically bound by an antibody.

As used herein, an "epitope" is a term in the art and refers to a localized region of an antigen to which an antibody can specifically bind. An epitope can be a linear epitope or a conformational, non-linear, or discontinuous, epitope. In the case of a polypeptide antigen, for example, an epitope can be contiguous amino acids of the polypeptide (a "linear" epitope) or an epitope can comprise amino acids from two or more non-contiguous regions of the polypeptide (a "conformational," "non-linear" or "discontinuous" epitope). It will be appreciated by one of skill in the art that, in general, a linear epitope may or may not be dependent on secondary, tertiary, or quaternary structure.

As used herein, the terms "immunospecifically binds," "immunospecifically recognizes," "specifically binds," and "specifically recognizes" are analogous terms in the context of antibodies and refer to molecules that bind to an antigen/epitope as such binding is understood by one skilled in the art. For example, a molecule (e.g., an antibody) that specifically binds to an antigen may bind to other peptides or polypeptides, generally with lower affinity as determined by, e.g., immunoassays, surface plasmon resonance assays, for example, Biacore™ KinExA platform (Sapidyne Instruments, Boise, Id.), or other assays known in the art. In a specific embodiment, molecules that specifically bind to an antigen bind to the antigen with a K$_a$ that is at least 2 logs, 2.5 logs, 3 logs, 4 logs or greater than the K$_a$ when the molecules bind to another antigen. In another specific embodiment, molecules that specifically bind to an antigen do not cross react with other proteins. In another specific embodiment, molecules that specifically bind to an antigen do not cross react with other non-CD47 proteins.

As used herein, the term "monoclonal antibody" is a well known term of art that refers to an antibody obtained from a population of homogenous or substantially homogeneous antibodies. The term "monoclonal" is not limited to any particular method for making the antibody. Generally, a population of monoclonal antibodies can be generated by cells, a population of cells, or a cell line. In specific embodiments, a "monoclonal antibody," as used herein, is an antibody produced by a single cell or cell line wherein the antibody immunospecifically binds to a CD47 epitope as determined, e.g., by ELISA or other antigen-binding or competitive binding assay known in the art or in the Examples provided herein. In particular embodiments, a monoclonal antibody can be a chimeric antibody or a humanized antibody. In certain embodiments, a monoclonal antibody is a monovalent antibody or multivalent (e.g., bivalent) antibody.

As used herein, the term "non-natural amino acid" refers to an amino acid that is not a proteinogenic amino acid, or a post-translationally modified variant thereof. In particular, the term refers to an amino acid that is not one of the 20 common amino acids or pyrrolysine or selenocysteine, or post-translationally modified variants thereof.

As used herein, the term "polyclonal antibodies" refers to an antibody population that includes a variety of different antibodies that immunospecifically bind to the same and/or to different epitopes within an antigen or antigens.

As used herein, the terms "variable region" or "variable domain" refer to a portion of an antibody, generally, a portion of an antibody light or heavy chain, typically about the amino-terminal 110 to 120 amino acids in a mature heavy chain and about the amino-terminal 90 to 100 amino acids in a mature light chain. Variable regions comprise complementarity determining regions (CDRs) flanked by framework regions (FRs). Generally, the spacial orientation of CDRs and FRs are as follows, in an N-terminal to C-terminal direction: FR1-CDR1-FR2-CDR2-FR3-CDR3-FR4. Without wishing to be bound by any particular mechanism or theory, it is believed that the CDRs of the light and heavy chains are primarily responsible for the interaction of the antibody with antigen and for the specificity of the antibody for an epitope. In a specific embodiment, numbering of amino acid positions of antibodies described herein is according to the EU Index, as in Kabat et al. (1991) *Sequences of Proteins of Immunological Interest*, Fifth Edition, U.S. Department of Health and Human Services, NIH Publication No. 91-3242. In certain embodiments, the variable region is a human variable region. In certain embodiments, the variable region comprises murine (e.g., mouse or rat) CDRs and human framework regions (FRs). In particular embodiments, the variable region is a primate (e.g., human or non-human primate) variable region. In certain embodiments, the variable region comprises murine (e.g., mouse or rat) CDRs and primate (e.g., human or non-human primate) framework regions (FRs). As a non-limiting example, a variable region described herein is obtained from assembling two or more fragments of human sequences into a composite human sequence.

In certain aspects, the CDRs of an antibody can be determined according to (i) the Kabat numbering system (Kabat et al. (1971) *Ann. NY Acad. Sci.* 190:382-391 and, Kabat et al. (1991) *Sequences of Proteins of Immunological Interest*, Fifth Edition, U.S. Department of Health and Human Services, NIH Publication No. 91-3242); or (ii) the Chothia numbering scheme, which will be referred to herein as the "Chothia CDRs" (see, e.g., Chothia and Lesk, 1987, J. Mol. Biol., 196:901-917; Al-Lazikani et al., 1997, J. Mol. Biol., 273:927-948; Chothia et al., 1992, J. Mol. Biol., 227:799-817; Tramontano A et al., 1990, J. Mol. Biol. 215(1):175-82; and U.S. Pat. No. 7,709,226); or (iii) the ImMunoGeneTics (IMGT) numbering system, for example, as described in Lefranc, M.-P., 1999, The Immunologist, 7:132-136 and Lefranc, M.-P. et al., 1999, Nucleic Acids Res., 27:209-212 ("IMGT CDRs"); or (iv) MacCallum et al., 1996, J. Mol. Biol., 262:732-745. See also, e.g., Martin, A., "Protein Sequence and Structure Analysis of Antibody Variable Domains," in *Antibody Engineering*, Kontermann and Dübel, eds., Chapter 31, pp. 422-439, Springer-Verlag, Berlin (2001).

With respect to the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). As is well known to those of skill in the art, using the Kabat numbering system, the actual linear amino acid sequence of the antibody variable domain can contain fewer or additional amino acids due to a shortening or lengthening of a FR and/or CDR and, as such, an amino acid's Kabat number is not necessarily the same as its linear amino acid number.

Antibodies provided herein can be of any type (e.g., IgG, IgE, IgM, IgD, IgA or IgY), any class, (e.g., $IgG_1$, $IgG_2$, $IgG_3$, $IgG_4$, $IgA_1$ or $IgA_2$), or any subclass (e.g., $IgG_{2a}$ or $IgG_{2b}$, or a mixture thereof) of immunoglobulin molecule. In certain embodiments, antibodies described herein are IgG antibodies (e.g., human IgG), or a class (e.g., human $IgG_1$, $IgG_2$, $IgG_3$ or $IgG_4$) or subclass thereof.

In specific aspects, provided herein is an antibody comprising an antibody light chain and heavy chain, e.g., a separate light chain and heavy chain. With respect to the light chain, in a specific embodiment, the light chain of an antibody described herein is a kappa (κ) light chain. In another specific embodiment, the light chain of an antibody described herein is a lambda (λ) light chain. In another embodiment, light chain is a mixed sequence, e.g., the variable portion of the light chain comprises kappa light chain sequences and the constant region of the light chain comprises lambda light chain sequences, or vice versa. In certain embodiments, the light chain of an antibody described herein is a human kappa light chain or a human lambda light chain. Non-limiting examples of human constant region sequences have been described in the art, e.g., see U.S. Pat. No. 5,693,780 and Kabat et al. (1991) *Sequences of Proteins of Immunological Interest*, Fifth Edition, U.S. Department of Health and Human Services, NIH Publication No. 91-3242.

In a specific aspect, provided herein is an antibody, e.g. a monoclonal antibody, which specifically binds to human CD47, wherein such an anti-CD47 antibody is a variant of a parental anti-CD47 antibody, wherein the anti-CD47 antibody, when produced using a cell-free (CF) expression system, has a higher antibody expression titer or yield compared to that of the parental anti-CD47 antibody when expressed in the CF system, and wherein the anti-CD47 antibody comprises one or more amino acid modifications, for example, 1-15 amino acid modifications, relative to the the parental anti-CD47 antibody. In a particular aspect, the one or more amino acid modifications, for example, 1-15 amino acid modifications, are within the heavy chain or VH (e.g., SEQ ID NO: 1). In a particular aspect, the one or more amino acid modifications, for example, 1-15 amino acid modifications, are within the framework region of a VH (e.g., SEQ ID NO: 1). In a certain aspect, the anti-CD47 antibody provided herein which is a variant of a parental anti-CD47 antibody comprising the CDRs (e.g., Kabat CDRs) of the parental anti-CD47 antibody.

In a specific aspect, provided herein is an antibody, e.g. a monoclonal antibody, which specifically binds to human CD47, wherein such an anti-CD47 antibody is a variant of a parental anti-CD47 antibody, wherein the anti-CD47 antibody, when produced using a cell-free (CF) expression system, has a higher antibody expression titer or yield compared to that of the parental anti-CD47 antibody when expressed in the CF system, and wherein the anti-CD47 antibody comprising one or more amino acid modifications, for example, 1-15 amino acid modifications, relative to the the parental anti-CD47 antibody. In a particular aspect, the one or more amino acid modifications, for example, 5 or 14 amino acid modifications, are within the heavy chain or VH (e.g., SEQ ID NO: 1). In a particular aspect, the one or more amino acid modifications, for example, 5, 10, 13 or 14 amino acid modifications, are within the framework region of a VH (e.g., SEQ ID NO: 1). In a particular aspect, the one or more amino acid modifications, for example, 5, 13 or 14 amino acid modifications are within the framework region of a VH (e.g., SEQ ID NO: 1). In a certain aspect, the anti-CD47 antibody provided herein which is a variant of a parental anti-CD47 antibody comprising the CDRs (e.g., Kabat CDRs) of the parental anti-CD47 antibody. In certain aspects, such anti-CD47 antibody is an IgG1, IgG2, IgG3, or IgG4 isotype antibody. In certain aspects, such anti-CD47 antibody is an IgG1 isotype antibody. In certain aspects, such anti-CD47 antibody is an IgG1 Z allotype isotype antibody. In certain aspects, such anti-CD47 antibody is an IgG4, such as an IgG4P or IgG4PE, isotype antibody.

In a specific aspect, provided herein is an antibody, e.g. a monoclonal antibody, which specifically binds to human CD47, wherein such an anti-CD47 antibody is a variant of a parental anti-CD47 antibody, wherein the anti-CD47 antibody, when produced using a cell-free (CF) expression system, has a higher antibody expression titer or yield compared to that of the parental anti-CD47 antibody when expressed in the CF system. In specific embodiments, the parental anti-CD47 antibody is antibody AB6.12 (see, e.g., U.S. Application Publication No. US 2014/0140989 A1, which is incorporated herein by reference in its entirety). The amino acid sequences of the heavy chain variable region (VH) and light chain variable region (VL) of antibody AB6.12 are provided below, wherein the Kabat CDRs are underlined. In a certain aspect, the anti-CD47 antibody provided herein is a variant of parental antibody AB6.12, and comprises the CDRs (e.g., Kabat CDRs) of parental antibody AB6.12, for example SEQ ID NOs: 14-19. In certain aspects, such anti-CD47 antibody is an IgG1, IgG2, IgG3, or IgG4 isotype antibody. In certain aspects, such anti-CD47 antibody is an IgG1 isotype antibody. In certain aspects, such anti-CD47 antibody is an IgG1 Z allotype isotype antibody. In certain aspects, such anti-CD47 antibody is an IgG4, such as an IgG4P or IgG4PE, isotype antibody.

Anti-CD47 antibody AB6.12 heavy chain variable region (VH) (Kabat CDRs 1-3 are underlined, SEQ ID NOs: 14-16):

```
                                            (SEQ ID NO: 1)
QMQLVQSGAEVKKTGSSVKVSCKASGFNIKDYYLHWVRQAPGQALEWMGW

IDPDQGDTEYAQKFQDRVTITRDRSMSTAYMELSSLRSEDTAMYYCNAAY

GSSSYPMDYWGQGTTVTV
```

Anti-CD47 antibody AB6.12 light chain variable region (VL) (Kabat CDRs 1-3 are underlined, SEQ ID NOs: 17-19):

```
                                            (SEQ ID NO: 12)
NIQMTQSPSAMSASVGDRVTITCKASQDIHRYLSWFQQKPGKVPKHLIYR

ANRLVSGVPSRFSGSGSGTEFTLTISSLQPEDFATYYCLQYDEFPYTFGG

GTKVEIK
```

In a specific embodiment, an anti-CD47 described herein comprises one or more amino acid modifications (e.g., 1-15 amino acid modifications), for example in the VH framework region, of a parental antibody, e.g., a parental antibody selected from anti-CD47 antibodies described in U.S. Application Publication No. US 2014/0140989 A1, which is hereby incorporated by reference in its entirety, for example anti-CD47 antibodies described in Table 1 of U.S. Application Publication No. US 2014/0140989 A1 (e.g., anti-CD47 antibody 2A1, AB2.03, AB2.04, AB2.05, AB2.06, AB2.07, AB2.08, AB2.09, AB2.13, AB3.09, AB6.12, AB6.13, AB6.14, AB6.17, AB10.13, AB10.14, AB11.05, AB12.05, AB15.05, AB16.05, AB17.05, AB22.05, AB23.05, AB24.05, and AB25.05).

In a specific aspect, provided herein is an antibody, e.g. a monoclonal antibody, which specifically binds to human CD47, wherein such an anti-CD47 antibody is a variant of a parental anti-CD47 antibody, wherein the anti-CD47 antibody, when produced using a cell-free (CF) expression system, has a higher antibody expression titer or yield compared to that of the parental anti-CD47 antibody when expressed in the CF system, and wherein the anti-CD47 antibody comprises a VH comprising the following N-terminal to C-terminal sequence: $\underline{X_1}$Q$\underline{X_2}$QLVQSGAEVKK$\underline{X_3}$G$\underline{X_4}$SVKVSCKASGFNIKDYYLHWVRQAPGQ$\underline{X_5}$LEWMGWIDP DQGDTEYAQK$\underline{X_6}$Q$\underline{X_7}$RVT$\underline{X_8}$T$\underline{X_9}$D$\underline{X_{10}}$S$\underline{X_{11}}$STAYMEL$\underline{X_{12}}$SLRS$\underline{X_{13}}$DTA$\underline{X_{14}}$YYCNAAYGSS SYPMDYWGQGTTVTV (SEQ ID NO: 20), wherein the underlined amino acid residues for $X_1$-$X_{14}$ are ordered from N-terminus to C-terminus, wherein $X_1$ is M or there is no amino acid at position $X_1$, $X_2$ is an amino acid with hydrophobic side chains such as M or V, $X_3$ is T or P, $X_4$ is S or A, $X_5$ is an acid having aliphatic side chains such as A or G, $X_6$ is F or L, $X_7$ is D or G, $X_8$ is an amino acid with hydrophobic side chains such as I or M, $X_9$ is R or T, $X_{10}$ is R or T, $X_{11}$ is M or T, $X_{12}$ is S or R, $X_{13}$ is a negatively charged amino acid such as E or D, and $X_{14}$ is an amino acid with hydrophobic side chains such as M or V.

In particular aspects, an anti-CD47 antibody described herein comprises a VH comprising the sequence of SEQ ID NO: 20, wherein the amino acid at position $X_1$ is any amino acid such as M, $X_2$ is not M, $X_3$ is not T, $X_4$ is not S, $X_5$ is not A, $X_6$ is not F, $X_7$ is not D, $X_8$ is not I, $X_9$ is not R, $X_{10}$ is not R, $X_{11}$ is not M, $X_{12}$ is not S, $X_{13}$ is not E, and/or $X_{14}$ is not M. In particular aspects, any 1, 2, 3, 4, 5, 6, 7, 8, 9, 10, 11, 12, 13, or 14 of $X_1$ to $X_{14}$ are not these amino acids. In particular aspects, the VH amino acid sequence is not the VH amino acid sequence of antibody AB6.12, for example, the VH amino acid sequence is not SEQ ID NO: 1.

In particular aspects, an anti-CD47 antibody described herein comprises a VH comprising the sequence of SEQ ID NO: 20, wherein the amino acid at position $X_7$ is not G, $X_9$ is not A and/or $X_{11}$ is not S. In particular aspects, any 1, 2, or 3 of $X_7$, $X_9$ and $X_{11}$ are not these amino acids. In particular aspects, when the amino acid at position $X_7$ is G, then $X_8$ is M and/or $X_{10}$ is T, $X_9$ is not A and/or $X_{11}$ is not S.

In particular aspects, an anti-CD47 antibody described herein comprises a VH comprising the sequence of SEQ ID NO: 20, wherein the amino acid at position $X_7$ is not G, $X_8$ is not M, $X_9$ is not E, $X_{10}$ is not T, and/or $X_{11}$ is not T. In particular aspects, any 1, 2, 3, or 4 of $X_7$ to $X_{11}$ are not these amino acids. In particular aspects, when the amino acid at position $X_7$ is G, then $X_8$ is M, $X_{10}$ is T, $X_9$ is not E, and $X_{11}$ is T.

In a particular aspect, an anti-CD47 antibody described herein comprises a VH comprising the sequence of SEQ ID NO: 20, wherein the VH does not comprise the amino acid sequence of SEQ ID NO: 5, 6, 7, 8, 9, 10, 12, 13, 14, 15, 16, 17, 18, 19, 20, 21, 22, 23, 24, 25, 26, 27, 28, 29, or 30, of U.S. Application Publication No. US2014/0140989 A1, which is incorporated herein by reference in its entirety. In a particular aspect, an anti-CD47 antibody described herein comprises a VH comprising the consensus sequence of SEQ ID NO: 20, wherein the VH does not comprise the framework regions of the amino acid sequence of SEQ ID NO: 5, 6, 7, 8, 9, 10, 12, 13, 14, 15, 16, 17, 18, 19, 20, 21, 22, 23, 24, 25, 26, 27, 28, 29, or 30, of U.S. Application Publication No. US2014/0140989 A1, which is incorporated herein by reference in its entirety.

In particular aspects, $X_1$ is M, $X_2$ is V, $X_3$ is P, $X_4$ is A, $X_5$ is G, $X_6$ is L, $X_7$ is G, $X_8$ is M, $X_9$ is T, $X_{10}$ is T, $X_{11}$ is T, $X_{12}$ is R, $X_{13}$ is D, and/or $X_{14}$ is V. In particular embodiments, any 1, 2, 3, 4, 5, 6, 7, 8, 9, 10, 11, 12, 13, or 14 of $X_1$ to $X_{14}$ are these amino acids.

In particular aspects, $X_1$ is M, $X_2$ is M, $X_3$ is P, $X_4$ is S, $X_5$ is A, $X_6$ is F, $X_7$ is G, $X_8$ is I, $X_9$ is R, $X_{10}$ is R, $X_{11}$ is T, $X_{12}$ is R, $X_{13}$ is E, and/or $X_{14}$ is V. In particular embodiments, any 1, 2, 3, 4, 5, 6, 7, 8, 9, 10, 11, 12, 13, or 14 of $X_1$ to $X_{14}$ are these amino acids.

In a particular aspect, an anti-CD47 antibody provided herein is not antibody AB6.12. In a particular aspect, an anti-CD47 antibody provided herein does not comprise a VH (e.g., SEQ ID NO: 1) and/or a VL (e.g., SEQ ID NO: 12) of antibody AB6.12.

In a specific aspect, an anti-CD47 antibody provided herein, comprises one of the following VH amino acid sequences presented in Table 1.

TABLE 1

| | VH amino acid sequence | |
|---|---|---|
| SEQ ID NO: | Description | VH amino acid sequence |
| 20 | Consensus | X1QX2QLvQSGAEVKKX3GX4SVKVSCKA SGFNIKDYYLHWVRQAPGQX5LEWMGWID PDQGDTEYAQKX6QX7RVTX8TX9DX10S X11STAYMELX12SLRSX13DTAX14YYC NAAYGSSSYPMDYWGQGTTVTV |
| 21 | 13 m | MQVQLVQSGAEVKKPGASVKVSCKASGFN IKDYYLHWVRQAPGQGLEWMGWIDPDQGD TEYAQKLQGRVTMTTDTSTSTAYMELRSL RSDDTAVYYCNAAYGSSSYPMDYWGQGTT VTV |
| 22 | 5 m | MQMQLVQSGAEVKKPGSSVKVSCKASGFN IKDYYLHWVRQAPGQALEWMGWIDPDQGD TEYAQKLQGRVTMTTDTSTSTAYMELRSL RSDDTAVYYCNAAYGSSSYPMDYWGQGTT VTV |

In a specific aspect, provided herein is an antibody, e.g. a monoclonal antibody, which specifically binds to human CD47, wherein such an anti-CD47 antibody is a variant of a parental anti-CD47 antibody, wherein the anti-CD47 antibody, when produced using a cell-free (CF) expression system, has a higher antibody expression titer or yield compared to that of the parental anti-CD47 antibody when expressed in the CF system, and wherein the anti-CD47 antibody comprises a VH comprising SEQ ID NO: 21. In certain aspects, such anti-CD47 antibody is an IgG1, IgG2, IgG3, or IgG4 isotype antibody. In certain aspects, such anti-CD47 antibody is an IgG1 isotype antibody. In certain aspects, such anti-CD47 antibody is an IgG1 Z allotype isotype antibody. In certain aspects, such anti-CD47 antibody is an IgG4, such as an IgG4P or IgG4PE, isotype antibody.

In a specific aspect, provided herein is an antibody, e.g. a monoclonal antibody, which specifically binds to human CD47, wherein such an anti-CD47 antibody is a variant of a parental anti-CD47 antibody, wherein the anti-CD47 antibody, when produced using a cell-free (CF) expression system, has a higher antibody expression titer or yield compared to that of the parental anti-CD47 antibody when expressed in the CF system, and wherein the anti-CD47 antibody comprises a VH comprising SEQ ID NO: 22. In certain aspects, such anti-CD47 antibody is an IgG1, IgG2, IgG3, or IgG4 isotype antibody. In certain aspects, such anti-CD47 antibody is an IgG1 isotype antibody. In certain aspects, such anti-CD47 antibody is an IgG1 Z allotype isotype antibody. In certain aspects, such anti-CD47 antibody is an IgG4, such as an IgG4P or IgG4PE, isotype antibody.

In a particular aspect, an anti-CD47 antibody (IgG1-13m) provided herein comprises an IgG1 heavy chain comprising the amino acid sequence as set forth below:

```
                                         (SEQ ID NO: 5)
MQVQLVQSGAEVKKPGASVKVSCKASGFNIKDYYLHWVRQAPGQGLEWMG

WIDPDQGDTEYAQKLQGRVTMTTDTSTSTAYMELRSLRSDDTAVYYCNAA

YGSSSYPMDYWGQGTTVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSPG

K
```

In a particular aspect, an anti-CD47 antibody (IgG1-13mZ) provided herein comprises an IgG1-Z allotype heavy chain comprising the amino acid sequence as set forth below:

```
                                         (SEQ ID NO: 6)
MQVQLVQSGAEVKKPGASVKVSCKASGFNIKDYYLHWVRQAPGQGLEWMG

WIDPDQGDTEYAQKLQGRVTMTTDTSTSTAYMELRSLRSDDTAVYYCNAA

YGSSSYPMDYWGQGTTVTVSSASTKGPSVFPLAPSSKSTSGGTAALGCLV

KDYFPEPVTVSWNSGALTSGVHTFPAVLQSSGLYSLSSVVTVPSSSLGTQ
```

```
TYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSREEMTKNQVSLTCLVKGFYPSDIAVEWESNGQPENNYKTTPP

VLDSDGSFFLYSKLTVDKSRWQQGNVFSCSVMHEALHNHYTQKSLSLSPG

K
```

In a particular aspect, an anti-CD47 antibody (IgG1-5m) provided herein comprises an IgG1 heavy chain comprising the amino acid sequence as set forth below:

```
                                         (SEQ ID NO: 7)
MQMQLVQSGAEVKKPGSSVKVSCKASGFNIKDYYLHWVRQAPGQALEWMG

WIDPDQGDTEYAQKFQGRVTITRDRSTSTAYMELRSLRSEDTAVYYCNAA

YGSSSYPMDYWGQGTTVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSPG

K
```

In a particular aspect, an anti-CD47 antibody (IgG4P-13m) provided herein comprises an IgG4P antibody comprising the amino acid sequence as set forth below:

```
                                         (SEQ ID NO: 8)
MQVQLVQSGAEVKKPGASVKVSCKASGFNIKDYYLHWVRQAPGQGLEWMG

WIDPDQGDTEYAQKLQGRVTMTTDTSTSTAYMELRSLRSDDTAVYYCNAA

YGSSSYPMDYWGQGTTVTVSSASTKGPSVFPLAPCSRSTSESTAALGCLV

KDYFPEPVTVSWNSGALTSGVHTFPAVLQSSGLYSLSSVVTVPSSSLGTK

TYTCNVDHKPSNTKVDKRVESKYGPPCPPCPAPEFLGGPSVFLFPPKPKD

TLMISRTPEVTCVVVDVSQEDPEVQFNWYVDGVEVHNAKTKPREEQFNST

YRVVSVLTVLHQDWLNGKEYKCKVSNKGLPSSIEKTISKAKGQPREPQVY

TLPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLGK
```

In a particular aspect, an anti-CD47 antibody (IgG4P-5m) provided herein comprises an IgG4P heavy chain comprising the amino acid sequence as set forth below:

```
                                         (SEQ ID NO: 9)
MQMQLVQSGAEVKKPGSSVKVSCKASGFNIKDYYLHWVRQAPGQALEWMG

WIDPDQGDTEYAQKFQGRVTITRDRSTSTAYMELRSLRSEDTAVYYCNAA

YGSSSYPMDYWGQGTTVTVSSASTKGPSVFPLAPCSRSTSESTAALGCLV

KDYFPEPVTVSWNSGALTSGVHTFPAVLQSSGLYSLSSVVTVPSSSLGTK

TYTCNVDHKPSNTKVDKRVESKYGPPCPPCPAPEFLGGPSVFLFPPKPKD

TLMISRTPEVTCVVVDVSQEDPEVQFNWYVDGVEVHNAKTKPREEQFNST

YRVVSVLTVLHQDWLNGKEYKCKVSNKGLPSSIEKTISKAKGQPREPQVY

TLPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLGK
```

In a particular aspect, an anti-CD47 antibody (IgG4PE-13m) provided herein comprises an IgG4PE heavy chain comprising the amino acid sequence as set forth below:

```
                                         (SEQ ID NO: 10)
MQVQLVQSGAEVKKPGASVKVSCKASGFNIKDYYLHWVRQAPGQGLEWMG

WIDPDQGDTEYAQKLQGRVTMTTDTSTSTAYMELRSLRSDDTAVYYCNAA

YGSSSYPMDYWGQGTTVTVSSASTKGPSVFPLAPCSRSTSESTAALGCLV

KDYFPEPVTVSWNSGALTSGVHTFPAVLQSSGLYSLSSVVTVPSSSLGTK

TYTCNVDHKPSNTKVDKRVESKYGPPCPPCPAPEFEGGPSVFLFPPKPKD

TLMISRTPEVTCVVVDVSQEDPEVQFNWYVDGVEVHNAKTKPREEQFNST

YRVVSVLTVLHQDWLNGKEYKCKVSNKGLPSSIEKTISKAKGQPREPQVY

TLPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLGK
```

In a particular aspect, an anti-CD47 antibody (IgG4PE-5m) provided herein comprises an IgG4PE heavy chain comprising the amino acid sequence as set forth below:

```
                                         (SEQ ID NO: 11)
MQMQLVQSGAEVKKPGSSVKVSCKASGFNIKDYYLHWVRQAPGQALEWMG

WIDPDQGDTEYAQKFQGRVTITRDRSTSTAYMELRSLRSEDTAVYYCNAA

YGSSSYPMDYWGQGTTVTVSSASTKGPSVFPLAPCSRSTSESTAALGCLV

KDYFPEPVTVSWNSGALTSGVHTFPAVLQSSGLYSLSSVVTVPSSSLGTK

TYTCNVDHKPSNTKVDKRVESKYGPPCPPCPAPEFEGGPSVFLFPPKPKD

TLMISRTPEVTCVVVDVSQEDPEVQFNWYVDGVEVHNAKTKPREEQFNST

YRVVSVLTVLHQDWLNGKEYKCKVSNKGLPSSIEKTISKAKGQPREPQVY

TLPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLGK
```

In a specific aspect, provided herein is an antibody, e.g. a monoclonal antibody, which specifically binds to human CD47, wherein such an anti-CD47 antibody is a variant of a parental anti-CD47 antibody, wherein the anti-CD47 antibody, when produced using a cell-free (CF) expression system, has a higher antibody expression titer or yield compared to that of the parental anti-CD47 antibody when expressed in the CF system, and wherein the anti-CD47 antibody comprises a light chain comprising a kappa or lambda light chain constant region (e.g., human kappa or lambda light chain constant region), for example SEQ ID NO: 13.

In a specific aspect, provided herein is an antibody, e.g. a monoclonal antibody, which specifically binds to human CD47, wherein such an anti-CD47 antibody is a variant of a parental anti-CD47 antibody, wherein the anti-CD47 antibody, when produced using a cell-free (CF) expression system, has a higher antibody expression titer or yield compared to that of the parental anti-CD47 antibody when expressed in the CF system, and wherein the anti-CD47 antibody comprises (i) a VH described herein (e.g., SEQ ID NO: 20, 21, or 22) or a heavy chain described herein (e.g., any one of SEQ ID NOs:5-11), and (ii) a light chain comprising a kappa or lambda light chain constant region (e.g., human kappa or lambda light chain constant region), for example SEQ ID NO: 13, e.g., as set forth below (anti-CD47 antibody light chain (Ig K)), or SEQ ID NO: 13 without the amino acid M at the N-terminus:

```
                                               (SEQ ID NO: 13)
MNIQMTQSPSAMSASVGDRVTITCKASQDIHRYLSWFQQKPGKVPKHLIY

RANRLVSGVPSRFSGSGSGTEFTLTISSLQPEDFATYYCLQYDEFPYTFG

GGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC
```

In a specific embodiment, an anti-CD47 described herein is not an anti-CD47 antibody described in U.S. Application Publication No. US 2014/0140989 A1, which is hereby incorporated by reference in its entirety, for example any one of anti-CD47 antibodies in Table 1 of the publication (e.g., anti-CD47 antibody 2A1, AB2.03, AB2.04, AB2.05, AB2.06, AB2.07, AB2.08, AB2.09, AB2.13, AB3.09, AB6.12, AB6.13, AB6.14, AB6.17, AB10.13, AB10.14, AB11.05, AB12.05, AB15.05, AB16.05, AB17.05, AB22.05, AB23.05, AB24.05, and AB25.05), or any antibody comprising any of SEQ ID NOS: 5-30 of the publication.

In some embodiments, an anti-CD47 antibody provided herein or an antigen-binding fragment thereof is an IgG isotype. In some embodiments, the constant region of the antibody is of human IgG1 isotype, having an amino acid sequence:

```
                                               (SEQ ID NO: 34)
ASTKGPSVFP LAPSSKSTSG GTAALGCLVK DYFPEPVTVS

WNSGALTSGV HTFPAVLQSS GLYSLSSVVT VPSSSLGTQT

YICNVNHKPS NTKVDKKVEP KSCDKTHTCP PCPAPELLGG

PSVFLFPPKP KDTLMISRTP EVTCVVVDVS HEDPEVKFNW

YVDGVEVHNA KTKPREEQYN STYRVVSVLT VLHQDWLNGK

EYKCKVSNKA LPAPIEKTIS KAKGQPREPQ VYTLPPSRDE

LTKNQVSLTC LVKGFYPSDI AVEWESNGQP ENNYKTTPPV

LDSDGSFFLY SKLTVDKSRW QQGNVFSCSV MHEALHNHYT

QKSLSLSPGK
```

In some embodiments, the human IgG1 constant region is modified at amino acid Asn297 (Boxed, Kabat Numbering) to prevent to glycosylation of the antibody, for example Asn297Ala (N297A). In some embodiments, the constant region of the antibody is modified at amino acid Leu235 (Kabat Numbering) to alter Fc receptor interactions, for example Leu235Glu (L235E) or Leu235Ala (L235A). In some embodiments, the constant region of the antibody is modified at amino acid Leu234 (Kabat Numbering) to alter Fc receptor interactions, e.g., Leu234Ala (L234A). In some embodiments, the constant region of the antibody is altered at both amino acid 234 and 235, for example Leu234Ala and Leu235Ala (L234A/L235A) (EU index of Kabat et al 1991 *Sequences of Proteins of Immunological Interest*).

In some embodiments, the constant region of an anti-CD47 antibody provided herein is of human IgG2 isotype, having an amino acid sequence:

```
                                               (SEQ ID NO: 35)
ASTKGPSVFP LAPCSRSTSE STAALGCLVK DYFPEPVTVS

WNSGALTSGV HTFPAVLQSS GLYSLSSVVT VPSSNFGTQT

YTCNVDHKPS NTKVDKTVER KCCVECPPCP APPVAGPSVF

LFPPKPKDTL MISRTPEVTC VVVDVSHEDP EVQFNWYVDG

VEVHNAKTKP REEQFNSTFR VVSVLTVVHQ DWLNGKEYKC

KVSNKGLPAP IEKTISKTKG QPREPQVYTL PPSREEMTKN

QVSLTCLVKG FYPSDISVEW ESNGQPENNY KTTPPMLDSD

GSFFLYSKLT VDKSRWQQGN VFSCSVMHEA LHNHYTQKSL

SLSPGK
```

In some embodiments, the human IgG2 constant region is modified at amino acid Asn297 (Boxed, Kabat Numbering) to prevent to glycosylation of the antibody, e.g., Asn297Ala (N297A).

In some embodiments, the constant region of an anti-CD47 antibody provided herein is of human IgG3 isotype, having an amino acid sequence:

```
                                               (SEQ ID NO: 36)
ASTKGPSVFP LAPCSRSTSG GTAALGCLVK DYFPEPVTVS

WNSGALTSGV HTFPAVLQSS GLYSLSSVVT VPSSSLGTQT

YTCNVNHKPS NTKVDKRVEL KTPLGDTTHT CPRCPEPKSC

DTPPPCPRCP EPKSCDTPPP CPRCPEPKSC DTPPPCPRCP

APELLGGPSV FLFPPKPKDT LMISRTPEVT CVVVDVSHED

PEVQFKWYVD GVEVHNAKTK PREEQYNSTF RVVSVLTVLH

QDWLNGKEYK CKVSNKALPA PIEKTISKTK GQPREPQVYT

LPPSREEMTK NQVSLTCLVK GFYPSDIAVE WESSGQPENN

YNTTPPMLDS DGSFFLYSKL TVDKSRWQQG NIFSCSVMHE

ALHNRFTQKS LSLSPGK
```

In some embodiments, the human IgG3 constant region is modified at amino acid Asn297 (Boxed, Kabat Numbering) to prevent to glycosylation of the antibody, e.g., Asn297Ala (N297A). In some embodiments, the human IgG3 constant region is modified at amino acid 435 to extend the half-life, e.g., Arg435His (R435H) (EU index of Kabat et al 1991 *Sequences of Proteins of Immunological Interest*).

In some embodiments, the constant region of an anti-CD47 antibody provided herein is of human IgG4 isotype, having an amino acid sequence:

```
                                               (SEQ ID NO: 37)
ASTKGPSVFP LAPCSRSTSE STAALGCLVK DYFPEPVTVS

WNSGALTSGV HTFPAVLQSS GLYSLSSVVT VPSSSLGTKT
```

```
YTCNVDHKPS NTKVDKRVES KYGPPCPSCP APEFLGGPSV

FLFPPKPKDT LMISRTPEVT CVVVDVSQED PEVQFNWYVD

GVEVHNAKTK PREEQFNSTY RVVSVLTVLH QDWLNGKEYK

CKVSNKGLPS SIEKTISKAK GQPREPQVYT LPPSQEEMTK

NQVSLTCLVK GFYPSDIAVE WESNGQPENN YKTTPPVLDS

DGSFFLYSRL TVDKSRWQEG NVFSCSVMHE ALHNHYTQKS

LSLSLGK
```

In some embodiments, the human IgG4 constant region is modified within the hinge region to prevent or reduce strand exchange, e.g., Ser228Pro (S228P). In other embodiments, the human IgG4 constant region is modified at amino acid 235 to alter Fc receptor interactions, e.g., Leu235Glu (L235E). In some embodiments, the human IgG4 constant region is modified within the hinge and at amino acid 235, e.g., Ser228Pro and Leu235Glu (S228P/L235E). In some embodiments, the human IgG4 constant region is modified at amino acid Asn297 (Kabat Numbering) to prevent to glycosylation of the antibody, e.g., Asn297Ala (N297A). In some embodiments of the invention, the human IgG4 constant region is modified at amino acid positions Ser228, Leu235, and Asn297 (e.g., S228P/L235E/N297A). (EU index of Kabat et al 1991 *Sequences of Proteins of Immunological Interest*). In other embodiments of the invention, the antibody is of human IgG4 subclass and lacks glycosylation. In these embodiments the glycosylation can be eliminated by mutation at position 297 (Kabat numbering), for example N297A. In other embodiments, the glycosylation can be eliminated by production of the antibody in a host cell that lacks the ability for post-translational glycosylation, for example a bacterial or yeast derived system or a modified mammalian cell expression system.

In some embodiments, the human IgG constant region is modified to alter antibody-dependent cellular cytotoxicity (ADCC) and/or complement-dependent cytotoxicity (CDC), e.g., the amino acid modifications described in Natsume et al., 2008 Cancer Res, 68(10): 3863-72; Idusogie et al., 2001 J Immunol, 166(4): 2571-5; Moore et al., 2010 mAbs, 2(2): 181-189; Lazar et al., 2006 PNAS, 103(11): 4005-4010, Shields et al., 2001 JBC, 276(9): 6591-6604; Stavenhagen et al., 2007 Cancer Res, 67(18): 8882-8890; Stavenhagen et al., 2008 Advan. Enzyme Regul., 48: 152-164; Alegre et al, 1992 J Immunol, 148: 3461-3468; Reviewed in Kaneko and Niwa, 2011 Biodrugs, 25(1):1-11.

In some embodiments, the human IgG constant region is modified to induce heterodimerization. For example, having an amino acid modification within the CH3 domain at Thr366, which when replaced with a more bulky amino acid, e.g., Try (T366W), is able to preferentially pair with a second CH3 domain having amino acid modifications to less bulky amino acids at positions Thr366, Leu368, and Tyr407, e.g., Ser, Ala and Val, respectively (T366S/L368A/Y407V). Heterodimerization via CH3 modifications can be further stabilized by the introduction of a disulfide bond, for example by changing Ser354 to Cys (S354C) and Y349 to Cys (Y349C) on opposite CH3 domains (Reviewed in Carter, 2001 Journal of Immunological Methods, 248: 7-15).

In other aspects, the antibody lacks glycosylation, but is not modified at amino acid Asn297 (Kabat numbering). In these embodiments the glycosylation can, for example, be eliminated by production of the antibody in a host cell that lacks a post-translational glycosylation capacity, for example a bacterial or yeast derived system or a modified mammalian cell expression system. In certain aspects, such a system can be a CF expression system.

In certain embodiments, an anti-CD47 antibody described herein or an antigen-binding fragment thereof comprises amino acid sequences with certain percent identity relative to a parental antibody.

The determination of percent identity between two sequences (e.g., amino acid sequences or nucleic acid sequences) can be accomplished using a mathematical algorithm. A non-limiting example of a mathematical algorithm utilized for the comparison of two sequences is the algorithm of Karlin and Altschul, 1990, Proc. Natl. Acad. Sci. U.S.A. 87:2264 2268, modified as in Karlin and Altschul, 1993, Proc. Natl. Acad. Sci. U.S.A. 90:5873 5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules described herein. BLAST protein searches can be performed with the XBLAST program parameters set, e.g., to score 50, wordlength=3 to obtain amino acid sequences homologous to a protein molecule described herein. To obtain gapped alignments for comparison purposes, Gapped BLAST can be utilized as described in Altschul et al., 1997, Nucleic Acids Res. 25:3389 3402. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi.nlm.nih.gov). Another preferred, non limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

In certain embodiments, an antibody described herein or an antigen-binding fragment thereof comprises a VL domain having at least 80%, at least 85%, at least 90%, at least 95%, at least 98%, or at least 99% sequence identity to the amino acid sequence of SEQ ID NO: 12, wherein the antibody specifically binds to CD47. In certain embodiments, an antibody described herein or an antigen-binding fragment thereof comprises a VL domain having at least 80%, at least 85%, at least 90%, at least 95%, at least 98%, or at least 99% sequence identity to the amino acid sequence of SEQ ID NO: 12, wherein the antibody specifically binds to CD47, and wherein the antibody comprises CDRs (e.g., VL CDRs 1-3) that are identical to the CDRs (e.g., VL CDRs 1-3) of SEQ ID NO: 12 (e.g., SEQ ID NO: 17-19).

In certain embodiments, an antibody described herein or an antigen-binding fragment thereof comprises a light chain having at least 80%, at least 85%, at least 90%, at least 95%, at least 98%, or at least 99% sequence identity to the amino acid sequence of SEQ ID NO: 13, wherein the antibody specifically binds to CD47. In certain embodiments, an antibody described herein or an antigen-binding fragment thereof comprises a light domain having at least 80%, at least 85%, at least 90%, at least 95%, at least 98%, or at least 99% sequence identity to the amino acid sequence of SEQ ID NO: 13, wherein the antibody specifically binds to CD47, and wherein the antibody comprises CDRs (e.g., VL CDRs 1-3) that are identical to the CDRs (e.g., VL CDRs 1-3) of SEQ ID NO: 13 (e.g., SEQ ID NO: 17-19).

In certain embodiments, an antibody described herein or an antigen-binding fragment thereof comprises a VH domain having at least 80%, at least 85%, at least 90%, at least 95%, at least 98%, or at least 99% sequence identity to the amino acid sequence of SEQ ID NO: 1, wherein the antibody specifically binds to CD47 and wherein the anti-CD47 antibody, when produced using a cell-free expression system, has a higher antibody expression titer or yield compared to the parental antibody when produced in the CF expression system. In certain embodiments, an antibody described herein or an antigen-binding fragment thereof comprises a VH domain having at least 80%, at least 85%, at least 90%, at least 95%, at least 98%, or at least 99% sequence identity to the amino acid sequence of SEQ ID NO: 1, wherein the antibody specifically binds to CD47, and wherein the antibody comprises CDRs (e.g., VL CDRs 1-3) that are identical to the CDRs (e.g., VL CDRs 1-3) of SEQ ID NO: 1 (e.g., SEQ ID NO: 14-16).

In certain embodiments, an antibody described herein or an antigen-binding fragment thereof comprises a light chain having at least 80%, at least 85%, at least 90%, at least 95%, at least 98%, or at least 99% sequence identity to the amino acid sequence of SEQ ID NO: 2, wherein the antibody specifically binds to CD47 and wherein the anti-CD47 antibody, when produced using a cell-free expression system, has a higher antibody expression titer or yield compared to the parental antibody when produced in the CF expression system. In certain embodiments, an antibody described herein or an antigen-binding fragment thereof comprises a heavy domain having at least 80%, at least 85%, at least 90%, at least 95%, at least 98%, or at least 99% sequence identity to the amino acid sequence of SEQ ID NO: 2, wherein the antibody specifically binds to CD47, and wherein the antibody comprises CDRs (e.g., VL CDRs 1-3) that are identical to the CDRs (e.g., VL CDRs 1-3) of SEQ ID NO: 2 (e.g., SEQ ID NO: 17-19).

In certain embodiments, an antibody described herein or an antigen-binding fragment thereof comprises a light chain having at least 80%, at least 85%, at least 90%, at least 95%, at least 98%, or at least 99% sequence identity to the amino acid sequence of SEQ ID NO: 3, wherein the antibody specifically binds to CD47 and wherein the anti-CD47 antibody, when produced using a cell-free expression system, has a higher antibody expression titer or yield compared to the parental antibody when produced in the CF expression system. In certain embodiments, an antibody described herein or an antigen-binding fragment thereof comprises a heavy domain having at least 80%, at least 85%, at least 90%, at least 95%, at least 98%, or at least 99% sequence identity to the amino acid sequence of SEQ ID NO: 3, wherein the antibody specifically binds to CD47, and wherein the antibody comprises CDRs (e.g., VL CDRs 1-3) that are identical to the CDRs (e.g., VL CDRs 1-3) of SEQ ID NO: 3 (e.g., SEQ ID NO: 17-19).

In certain embodiments, an antibody described herein or an antigen-binding fragment thereof comprises a light chain having at least 80%, at least 85%, at least 90%, at least 95%, at least 98%, or at least 99% sequence identity to the amino acid sequence of SEQ ID NO: 4, wherein the antibody specifically binds to CD47 and wherein the anti-CD47 antibody, when produced using a cell-free expression system, has a higher antibody expression titer or yield compared to the parental antibody when produced in the CF expression system. In certain embodiments, an antibody described herein or an antigen-binding fragment thereof comprises a heavy domain having at least 80%, at least 85%, at least 90%, at least 95%, at least 98%, or at least 99% sequence identity to the amino acid sequence of SEQ ID NO: 4, wherein the antibody specifically binds to CD47, and wherein the antibody comprises CDRs (e.g., VL CDRs 1-3) that are identical to the CDRs (e.g., VL CDRs 1-3) of SEQ ID NO: 4 (e.g., SEQ ID NO: 17-19).

In certain aspects, anti-CD47 antibodies provided herein exhibit one or more desirable characteristics, such as, by way of non-limiting example, blocking of the interaction between CD47 and its ligand SIRPα and/or promoting (e.g., inducing or increasing) phagocytosis, without promoting (e.g., inducing or increasing) hemagglutination of erythrocytes, as well as anti-tumor activity. For example, anti-CD47 antibodies provided herein block at least 40%, at least 45%, at least 50%, at least 55%, at least 60%, at least 65%, at least 70%, at least 75%, at least 80%, at least 85%, at least 95%, or at least 99% of the interaction between CD47 and SIRPα as compared to the level of interaction between CD47 and SIRPα in the absence of the anti-CD47 antibody described herein.

In specific aspects, anti-CD47 antibodies described herein promote (e.g., induce or increase) phagocytosis of cells, e.g., CD47-expressing cells (e.g., CCRF-CEM cells), for example, by macrophages. In one aspect, the level of phagocytosois in the presence of anti-CD47 antibodies described herein is increased by at least 5%, at least 10%, at least 20%, at least 30%, at least 40%, at least 50%, at least 60%, at least 70%, at least 80%, at least 90%, at least 99%, at least 150%, at least 200%, compared to the level of aphagocytosis in the presence of anti-CD47 antibodies described herein.

In specific aspects, anti-CD47 antibodies described herein do not promote (e.g, induce or increase), or cause a significant level of, agglutination of cells, e.g., anti-CD47 antibodies described herein do not promote (e.g, induce or increase), or cause a significant level of, hemagglutination of red blood cells. In one aspect, the level of agglutination in the presence of anti-CD47 antibodies described herein is reduced by at least 5%, at least 10%, at least 20%, at least 30%, at least 40%, at least 50%, at least 60%, at least 70%, at least 80%, at least 90%, or at least 99% compared to the level of agglutination in the presence of anti-CD47 antibodies known to induce agglutination, such as MCA911 mouse anti-human CD47 antibody (BRIC126). In some aspects, anti-CD47 antibodies described herein do not promote (e.g., induce or increase), or cause a significant level of, agglutination if the level of agglutination in the presence of anti-CD47 antibodies described herein is reduced by at least 5%, at least 10%, at least 20%, at least 30%, at least 40%, at least 50%, at least 60%, at least 70%, at least 80%, at least 90%, or at least 99% compared to the level of agglutination in the presence of existing anti-CD47 antibodies known to induce agglutination, such as MCA911 mouse anti-human CD47 antibody (BRIC126).

Anti-CD47 antibodies described herein also include monoclonal antibodies that specifically bind CD47, wherein the antibody does not promote (e.g., induce or increase), or cause a significant level of, agglutination, e.g., red blood cell hemagglutination ("RBC hemagglutination").

In some aspects, the level of RBC depletion is determined by measuring the RBC count in a subject after administration of a treatment, e.g., an anti-CD47 antibody described herein. In some embodiments, anti-CD47 antibodies described herein do not promote (e.g., induce or increase), or cause a significant level of, RBC depletion if the RBC count in a subject after administration of an anti-CD47 antibody described herein is within the range of a normal, healthy subject. For example, the RBC count for a normal, healthy male human is about 4.7 to about 6.1 million cells per microliter of blood sample. For example, the RBC count for a normal, healthy female human is 4.2 to about 5.4 million cells per microliter of blood sample. In some aspects, anti-CD47 antibodies described herein do not promote (e.g., induce or increase), or cause a significant level of, RBC depletion if the RBC count in a subject after administration (e.g., 5 min, 10 min, 30 min, 1 h, 2 h, 3 h, 4 h, 5 h, 12 h, 24 h, 2 days, 4 days, 6 days, 1 week, 2 weeks, 3 weeks, 1 month, 2 months, or more) of an anti-CD47 antibody described herein is at least 50%, 60%, 70%, 80%, 90%, 95%, 97%, 98%, 99%, or 99.5% of the RBC count prior to administration. In specific aspects, anti-CD47 antibodies described herein do not promote (e.g., induce or increase), or cause a significant level of, RBC depletion if the RBC count in a subject after administration (5 min, 10 min, 30 min, 1 h, 2 h, 3 h, 4 h, 5 h, 12 h, 24 h, 2 days, 4 days, 6 days, 1 week, 2 weeks, 3 weeks, 1 month, 2 months, or more) of an anti47 antibody described herein is at least 50%, 60%, 70%, 80%, 90%, 95%, 97%, 98%, 99%, or 99.5% of the RBC count in a subject after administration of a placebo treatment (e.g., vehicle). RBC counts are determined by standard methods in the art.

In specific aspects, anti-CD47 antibodies described herein do not promote (e.g., induce or increase), or cause a significant level of, platelet depletion. For example, administration of an anti-CD47 antibody described herein leads to a percentage of platelets remaining of at least 30%, 40%, 50%, 60%, 70%, 80%, 90%, or 100%.

Also, anti-CD47 antibodies described herein include but are not limited to antibodies that do not bind to, or have a low binding affinity to, a Fcγ receptor (FcγR). For example, the constant region of an anti-CD47 antibody, e.g., when produced using a CF expression system, has a lower binding affinity to a FcγR than the constant region of an anti-CD47 antibody, e.g., when produced using a host cell (e.g., CHO cells) expression system.

Those skilled in the art will recognize that it is possible to quantitate, without undue experimentation, the level of agglutination, e.g., the level of hemagglutination of RBCs. For example, those skilled in the art will recognize that the level of hemagglutination is ascertained by measuring the area of an RBC dot after performing a hemagglutination assay in the presence of anti-CD47 antibodies described, as described in the Examples below. In some cases, the area of the RBC dot in the presence of anti-CD47 antibody described herein is compared to the area of the RBC dot in the absence of an anti-CD47 antibody, e.g., in the presence of zero hemagglutination. In this manner, hemagglutination is quantified relative to a baseline control. A larger RBC dot area corresponds to a higher level of hemagglutination. Alternatively, densitometry of the RBC dot may also be utilized to quantitate hemagglutination.

Those skilled in the art will recognize that it is possible to quantitate, without undue experimentation, the level of RBC depletion. For example, those skilled in the art will recognize that the level of RBC depletion is ascertained, e.g., by measuring the RBC count (i.e., the total number of RBCs in a sample of blood, e.g., by using a cell counter or a hemacytometer. Those of skill in the art will recognize that the RBCs in a sample of blood can optionally be isolated by fractionating whole blood using, e.g., centrifugation, prior to counting. In some cases, the RBC count in the presence of an anti-CD47 antibody described herein is compared to the RBC count in the absence of the CD47 antibody, e.g., in the presence of zero RBC depletion. In this manner, the level of RBC depletion is normalized relative to a baseline control.

In specific aspects, anti-CD47 antibodies provided herein exhibit inhibitory activity, for example by inhibiting CD47 expression (e.g., inhibiting cell surface expression of CD47), activity, and/or signaling, or by interfering with the interaction between CD47 and SIRPα. In certain aspects, anti-CD47 antibodies provided herein completely or partially reduce or otherwise modulate CD47 expression or activity upon binding to, or otherwise interacting with, CD47, e.g., a human CD47. The reduction or modulation of a biological function of CD47 is complete, significant, or partial upon interaction between the antibodies and the human CD47 polypeptide and/or peptide. Anti-CD47 antibodies described herein are considered to completely inhibit CD47 expression or activity when the level of CD47 expression or activity in the presence of the antibody is decreased by at least 95%, e.g., by 96%, 97%, 98%, 99% or 100% as compared to the level of CD47 expression or activity in the absence of interaction, e.g., binding, with the antibody described herein. In a particular aspect, anti-CD47 antibodies are considered to significantly inhibit CD47 expression or activity when the level of CD47 expression or activity in the presence of the CD47 antibody is decreased by at least 50%, e.g., 55%, 60%, 75%, 80%, 85% or 90% as compared to the level of CD47 expression or activity in the absence of binding with a CD47 antibody described herein. In certain aspects, anti-CD47 antibodies are considered to partially inhibit CD47 expression or activity when the level of CD47 expression or activity in the presence of the antibody is decreased by less than 95%, e.g., 10%, 20%, 25%, 30%, 40%, 50%, 60%, 75%, 80%, 85% or 90% as compared to the level of CD47 expression or activity in the absence of interaction, e.g., binding, with an antibody described herein.

In particular aspects, anti-CD47 antibodies provided herein comprise one or more non-natural amino acid residues at site-specific positions. See, e.g., U.S. Application Publication No. US 2014/0046030 A1, which is incorporated herein by reference in its entirety. In specific aspects, non-natural amino acid residues at site specific positions has advantages for antibody production yield, solubility, binding affinity, and/or activity. Non-limiting examples of non-natural amino acids have been described, see, e.g., U.S. Application Publication No. US 2014/0066598 A1.

In a particular aspect, provided herein are anti-CD47 antibodies conjugated to a conjugation moiety or an agent such as a label or toxin. A conjugation moiety can be any conjugation moiety deemed useful to one of skill in the art. For instance, a conjugation moiety can be a polymer, such as polyethylene glycol, that can improve the stability of the antibody in vitro or in vivo. A conjugation moiety can have therapeutic activity, thereby yielding an antibody-drug conjugate. A conjugation moiety can be a molecular payload that is harmful to target cells. A conjugation moiety can be a label useful for detection or diagnosis. In certain aspects, a conjugation moiety is linked to the antibody via a direct covalent bond. In certain aspects, a conjugation moiety is linked to the antibody via a linker. In particular aspects, a conjugation moiety or a linker is attached via one of the non-natural amino acids of an anti-CD47 antibody. Exemplary conjugation moieties and linkers have been described, e.g., see U.S. Application Publication No. US2014/0046030 A1, which is incorporated herein by reference in its entirety.

5.2 Antibody Production

Antibodies or an antigen-binding fragments described herein that immunospecifically bind to CD47 (e.g., ECD of human CD47) can be produced by any method known in the art, for example, by chemical synthesis or by recombinant expression techniques (e.g., CF expression systems).

Such methods can employ conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis et al. (1982) *Molecular Cloning: A Laboratory Manual*, Cold Spring Harbor Laboratory Press; Sambrook et al. (1989), *Molecular Cloning: A Laboratory Manual*, Second Edition, Cold Spring Harbor Laboratory Press; Sambrook et al. (2001) *Molecular Cloning: A Laboratory Manual*, Cold Spring Harbor Laboratory Press, Cold Spring Harbor, N.Y.; Ausubel et al., *Current Protocols in Molecular Biology*, John Wiley & Sons (1987 and annual updates); *Current Protocols in Immunology*, John Wiley & Sons (1987 and annual updates) Gait (ed.) (1984) *Oligonucleotide Synthesis: A Practical Approach*, IRL Press; Eckstein (ed.) (1991) *Oligonucleotides and Analogues: A Practical Approach*, IRL Press; Birren et al. (eds.) (1999) *Genome Analysis: A Laboratory Manual*, Cold Spring Harbor Laboratory Press.'

In specific aspects, anti-CD47 antibodies as provided herein can be produced using a CF expression system, for example, a CF expression system as known in the art, and, for example, as described in the Examples below. For example, CF expression systems can include cell-free extracts, such as S30 cell-free extracts, with DsbC, and 20 amino acids (e.g., natural or non-natural), and optionally, one or more of iodoacetamide, magnesium glutamate, ammonium glutamate, mM potassium glutamate, sodium pyruvate, AMP, GMP, UMP, and CMP, sodium oxalate, putrescine, spermidine, potassium phosphate, T7 RNAP, and oxidized (GSSG) glutathione. Heavy chain plasmids and light chain plasmids are added accordingly to the CF extract composition for polypeptide production and purification.

In some aspects, the CF expression system is an in vitro transcription and translation system as described in Yin et al., *mAbs*, 2012, 4:217-225, incorporated by reference in its entirety. In some aspects, the cell-free system utilizes a cell-free extract from a eukaryoctic cell or from a prokaryotic cell. In some aspects, the prokaryotic cell is *E. coli*.

In particular embodiments, the CF expression system can utilize a system as described in US Application Publication No. US 2014/0315245, which is hereby incorporated by reference in its entirety. For example, the CF expression system can comprise a bacterial extract having an oxidative phosphorylation system and components necessary for cell free protein synthesis and, in certain embodiments, can further comprise an exogenous protein chaperone, e.g., a protein disulfide isomerase (PDI), or a peptide-prolyl cis-trans isomerase. In specific embodiments, the PDI is a member of the Dsb (disulfide bond formation) family of *E. coli*, for example, DsbA or DsbC. In certain embodiments, the CF expression system comprises a cell extract of *E. coli* strain SBDG028, SBDG031, or SBDG044, as described in US Application Publication No. US 2014/0315245, which can, for example, be prepared according to Zawada et al., Biotechnology and Bioengineering (2011) vol. 108, No. 7.

In particular aspects, anti-CD47 antibodies provided herein comprise amino acid modifications that allow for antibody production using CF expression systems better than the parental antibodies. In a particular aspect, anti-CD47 antibodies provided herein which are produced using CF expression systems are aglycosylated.

Monoclonal antibodies can, for example, be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563 681 (Elsevier, N.Y., 1981). The term "monoclonal antibody" as used herein is not limited to antibodies produced through hybridoma technology. For example, monoclonal antibodies can be produced recombinantly from host cells engineered to express an antibody described herein (e.g., anti-CD47 antibody comprising the CDRs of any one of antibodies Ab235-Ab255) or a fragment thereof, for example, a light chain and/or heavy chain of such an antibody.

Further, the antibodies described herein or antigen-binding fragments thereof can also be generated using various phage display methods known in the art. In phage display methods, functional antibody domains are displayed on the surface of phage particles which carry the polynucleotide sequences encoding them. Examples of phage display methods that can be used to make the antibodies described herein include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; PCT Application No. PCT/GB91/O1 134; International Publication Nos. WO 90/02809, WO 91/10737, WO 92/01047, WO 92/18619, WO 93/1 1236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108.

Antibodies described herein can, for example, include chimeric antibodies. A chimeric antibody is a molecule in which different portions of the antibody are derived from different immunoglobulin molecules. For example, a chimeric antibody can contain a variable region of a mouse or rat monoclonal antibody fused to a constant region of a human antibody. Methods for producing chimeric antibodies are known in the art. See, e.g., Morrison, 1985, Science 229: 1202; Oi et al., 1986, BioTechniques 4:214; Gillies et al., 1989, J. Immunol. Methods 125:191-202; and U.S. Pat. Nos. 5,807,715, 4,816,567, 4,816,397, and 6,331,415.

Antibodies or antigen-binding fragments produced using techniques such as those described herein can be isolated using standard, well known techniques. For example, antibodies or antigen-binding fragments can be suitably separated from, e.g., culture medium, ascites fluid, serum, cell lysate, synthesis reaction material or the like by conventional immunoglobulin purification procedures such as, for example, protein A-Sepharose, hydroxylapatite chromatography, gel electrophoresis, dialysis, or affinity chromatography. As used herein, an "isolated" or "purified" antibody is substantially free of cellular material or other proteins from the cell or tissue source from which the antibody is derived, or substantially free of chemical precursors or other chemicals when chemically synthesized, or from the components of the CF expression system used to produce the antibodies.

Antibodies described herein include antibody fragments which recognize specific CD47 antigens and can be generated by any technique known to those of skill in the art. For example, Fab and F(ab')$_2$ fragments described herein can be produced by proteolytic cleavage of immunoglobulin molecules, using enzymes such as papain (to produce Fab fragments) or pepsin (to produce F(ab')$_2$ fragments). A Fab fragment corresponds to one of the two identical arms of an antibody molecule and contains the complete light chain paired with the VH and CH1 domains of the heavy chain. A F(ab')2 fragment contains the two antigen-binding arms of an antibody molecule linked by disulfide bonds in the hinge region. Alternatively, antibody fragments described herein can routinely be produced via well known recombinant expression techniques. See, e.g., PCT publication No. WO 92/22324; Mullinax et al., 1992, BioTechniques 12(6):864-869; Sawai et al., 1995, AJRI 34:26-34; and Better et al., 1988, Science 240:1041-1043.

Antibodies described herein can, for example, include humanized antibodies, e.g., deimmunized or composite human antibodies. A humanized antibody can comprise human constant region sequences. In certain embodiments, a humanized antibody can be selected from any class of immunoglobulins, including IgM, IgG, IgD, IgA and IgE, and any isotype, including IgG$_1$, IgG$_2$, IgG$_3$ and IgG$_4$. In certain embodiments, a humanized antibody can comprise kappa or lambda light chain constant sequences.

Humanized antibodies can be produced using a variety of techniques known in the art, including but not limited to, CDR-grafting (European Patent No. EP 239,400; International publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, PNAS 91:969-973), chain shuffling (U.S. Pat. No. 5,565,332), and techniques disclosed in, e.g., U.S. Pat. Nos. 6,407,213, 5,766,886, WO 9317105, Tan et al., J. Immunol. 169:1119 25 (2002), Caldas et al., Protein Eng. 13(5):353-60 (2000), Morea et al., Methods 20(3):267 79 (2000), Baca et al., J. Biol. Chem. 272(16):10678-84 (1997), Roguska et al., Protein Eng. 9(10):895 904 (1996), Couto et al., Cancer Res. 55 (23 Supp):5973s-5977s (1995), Couto et al., Cancer Res. 55(8):1717-22 (1995), Sandhu J S, Gene 150(2):409-10 (1994), and Pedersen et al., J. Mol. Biol. 235(3):959-73 (1994). See also U.S. Patent Pub. No. US 2005/0042664 A1 (Feb. 24, 2005), each of which is incorporated by reference herein in its entirety.

Antibodies described herein can, for example, be multispecific, e.g., bispecific, antibodies. Methods for making multispecific (e.g, bispecific antibodies) have been described, see, for example, U.S. Pat. Nos. 7,951,917, 7,183,076, 8,227,577, 5,837,242, 5,989,830, 5,869,620, 6,132,992, and 8,586,713.

Single domain antibodies, for example, antibodies lacking the light chains, can be produced by methods well-known in the art. See Riechmann et al., 1999, J. Immunol. 231:25-38; Nuttall et al., 2000, Curr. Pharm. Biotechnol. 1(3):253-263; Muylderman, 2001, J. Biotechnol. 74(4):277302; U.S. Pat. No. 6,005,079; and International Publication Nos. WO 94/04678, WO 94/25591, and WO 01/44301.

Human antibodies can be produced using any method known in the art. For example, well known transgenic mice which are incapable of expressing functional endogenous murine immunoglobulins, but which can express human immunoglobulin genes, can be used. Alternatively, for example, phage display techniques, described above, can be utilized. Moreover, in some embodiments, human antibodies can, for example, be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that immunospecifically bind to a target antigen (e.g., ECD of human CD47). Such methods are known and are described in the art, see, e.g., Shinmoto et al., Cytotechnology, 2004, 46:19-23; Naganawa et al., Human Antibodies, 2005, 14:27-31.

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

5.2.1 Polynucleotides, Cells and Vectors

In certain aspects, provided herein are polynucleotides comprising a nucleotide sequence encoding an antibody described herein or a fragment thereof (e.g., a variable light chain region and/or variable heavy chain region) that immunospecifically binds to a CD47 antigen, and vectors, e.g., vectors comprising such polynucleotides for recombinant expression in host cells (e.g., *E. coli* and mammalian cells). In certain aspects, provided herein are cells (e.g., host cells). Also provided herein are methods of making the antibodies and antigen-binding fragments described herein.

In certain aspects, provided herein are polynucleotides comprising a nucleotide sequence encoding the light chain or heavy chain of an antibody described herein. In certain embodiments, provided herein are polynucleotides comprising a nucleotide sequence encoding the light chain and heavy chain of an antibody described herein. The polynucleotides can comprise nucleotide sequences encoding a light chain comprising the VL FRs and CDRs of antibodies described herein. The polynucleotides can comprise nucleotide sequences encoding a heavy chain comprising the VH FRs and CDRs of antibodies described herein. In specific embodiments, a polynucleotide described herein encodes a VL chain region of SEQ ID NO: 13 or SEQ ID NO: 13 without amino acid M at the N-terminus. In specific embodiments, a polynucleotide described herein encodes a VH chain region of any one of SEQ ID NOs: 5-11 20-22. In specific embodiments, a polynucleotide described herein encodes a light chain comprising the amino acid sequence of SEQ ID NO: 13. In specific embodiments, a polynucleotide described herein encodes a heavy chain comprising the amino acid sequence of any one of SEQ ID NOs: 5-11.

In specific embodiments, a polynucleotide described herein comprises a nucleotide sequence provided in Table 2 encoding a light chain or a heavy chain of an anti-CD47 antibody provided here.

TABLE 2

Anti-CD47 antibody VH and VL nucleotide sequences

| SEQ ID NO: | Nucleotide sequences |
|---|---|
| 26 | Anti-CD47 IgG1-13m HC:<br>ATGCAAGTCCAATTGGTCCAGAGCGGTGCGGAAGTCAAGAAACCGGGTGCAAG<br>CGTCAAAGTTTCGTGCAAGGCGAGCGGTTTCAATATCAAAGACTATTATCTGC<br>ACTGGGTTCGTCAGGCTCCGGGCCAAGGCCTGGAGTGGATGGGTTGGATCGAT<br>CCGGACCAGGGCGACACGGAGTACGCTCAGAAGCTGCAGGGTCGTGTTACCAT<br>GACCACCGACACCAGCACGAGCACCGCGTACATGGAACTGCGCTCTCTGCGTT<br>CGGATGATACCGCGGTGTACTATTGCAACGCCGCGTACGGTAGCAGCAGCTAT<br>CCGATGGATTATTGGGGTCAAGGCACTACGGTGACTGTCAGCAGCGCCAGCAC<br>CAAGGGCCCGTCCGTGTTTCCGCTGGCGCCAAGCTCCAAGAGCACCAGCGGTG<br>GCACGGCCGCACTGGGTTGTCTGGTAAAAGATTACTTTCCTGAGCCGGTGACC<br>GTGAGCTGGAATTCAGGTGCACTGACGTCCGGCGTTCACACGTTCCCGGCAGT<br>TCTGCAGAGCTCCGGTTTGTACAGCCTGTCTAGCGTCGTGACGGTGCCGAGCA<br>GCAGCCTGGGTACCCAAACCTACATTTGCAACGTTAACCATAAGCCGAGCAAT<br>ACCAAAGTTGACAAGAAAGTCGAACCTAAGAGCTGTGATAAGACGCATACCTG<br>TCCGCCGTGCCCGGCACCGGAACTGTTGGGCGGTCCGAGCGTGTTCCTGTTTC<br>CGCCGAAGCCGAAAGATACCCTGATGATTAGCCGCACCCCTGAGGTGACGTGC<br>GTGGTTGTGGACGTTAGCCATGAGGATCCAGAGGTCAAATTCAATTGGTATGT<br>CGATGGTGTTGAGGTTCACAATGCCAAGACCAAACCGCGTGAAGAACAGTACA<br>ATAGCACCTACCGCGTGGTGAGCGTGCTGACGGTCCTGCACCAGGACTGGCTG<br>AACGGCAAAGAGTACAAGTGTAAGGTCAGCAACAAGGCGCTGCCAGCACCGAT<br>TGAAAAGACCATTTCTAAAGCGAAAGGTCAGCCGCGTGAGCCGCAAGTCTATA<br>CCCTGCCGCCGTCGCGCGATGAGCTGACTAAAAACCAGGTTAGCCTGACGTGC<br>CTGGTGAAAGGTTTCTACCCGAGCGACATCGCGGTGGAGTGGGAGAGCAACGG<br>TCAACCGGAGAATAACTACAAAACCACCCCACCGGTCTTGGACTCCGATGGCA<br>GCTTCTTTCTGTACTCTAAACTGACCGTTGACAAAAGCCGTTGGCAACAGGGC<br>AACGTCTTTAGCTGCAGCGTGATGCATGAGGCTCTGCACAACCACTACACCCA<br>AAAATCCCTGAGCCTGAGCCCGGGTAAGTAA |
| 27 | Anti-CD47 IgG1-13mZ HC:<br>ATGCAAGTCCAATTGGTCCAGAGCGGTGCGGAAGTCAAGAAACCGGGTGCAAG<br>CGTCAAAGTTTCGTGCAAGGCGAGCGGTTTCAATATCAAAGACTATTATCTGC<br>ACTGGGTTCGTCAGGCTCCGGGCCAAGGCCTGGAGTGGATGGGTTGGATCGAT<br>CCGGACCAGGGCGACACGGAGTACGCTCAGAAGCTGCAGGGTCGTGTTACCAT<br>GACCACCGACACCAGCACGAGCACCGCGTACATGGAACTGCGCTCTCTGCGTT<br>CGGATGATACCGCGGTGTACTATTGCAACGCCGCGTACGGTAGCAGCAGCTAT<br>CCGATGGATTATTGGGGTCAAGGCACTACGGTGACTGTCAGCAGCGCCAGCAC<br>CAAGGGCCCGTCCGTGTTTCCGCTGGCGCCAAGCTCCAAGAGCACCAGCGGTG<br>GCACGGCCGCACTGGGTTGTCTGGTAAAAGATTACTTTCCTGAGCCGGTGACC<br>GTGAGCTGGAATTCAGGTGCACTGACGTCCGGCGTTCACACGTTCCCGGCAGT<br>TCTGCAGAGCTCCGGTTTGTACAGCCTGTCTAGCGTCGTGACGGTGCCGAGCA<br>GCAGCCTGGGTACCCAAACCTACATTTGCAACGTTAACCATAAGCCGAGCAAT<br>ACCAAGGTTGACAAAAAAGTTGAACCGAAATCTTGTGATAAAACTCATACCTG<br>TCCGCCGTGCCCGGCGCCTGAGCTGTTGGGTGGTCCGTCGGTCTTTCTGTTCC<br>CGCCGAAGCCGAAAGACACCCTGATGATTAGCCGCACCCCGGAAGTTACGTGC<br>GTCGTCGTGGATGTCAGCCACGAGGACCCGGAGGTTAAGTTCAATTGGTATGT<br>CGATGGCGTGGAGGTTCACAACGCGAAAACCAAGCCGCGTGAGGAACAATACA<br>ATAGCACGTATCGCGTAGTGAGCGTGCTGACCGTGCTGCACCAAGATTGCTG<br>AATGGTAAAGAATACAAGTGCAAAGTGAGCAACAAGGCATTGCCGGCACCGAT<br>CGAAAAGACGATCAGCAAAGCGAAAGGCCAACCGCGTGAACCGCAGGTCTATA<br>CCCTGCCGCCGAGCCGTGAAGAAATGACGAAAAACCAAGTTAGCCTGACCTGT<br>CTGGTGAAGGGCTTTTACCCGAGCGACATCGCCGTCGAGTGGGAGTCTAACGG<br>CCAGCCGGAAAACAATTACAAAACCACGCCGCCAGTCCTGGACAGCGACGGTA<br>GCTTCTTTCTGTATAGCAAGCTGACCGTCGATAAAAGCCGTTGGCAGCAGGGT<br>AATGTGTTCAGCTGCAGCGTTATGCATGAGGCGCTGCACAATCACTATACCCA<br>GAAATCCTTGTCCCTGTCCCGGGTAAGTAA |

TABLE 2-continued

Anti-CD47 antibody VH and VL nucleotide sequences

| SEQ ID NO: | Nucleotide sequences |
|---|---|
| 28 | Anti-CD47 IgG1-5m HC:<br>ATGCAAATGCAATTGGTACAAAGCGGTGCGGAAGTAAAGAAACCGGGTTCGTC<br>GGTAAAGGTTAGCTGTAAAGCTTCTGGCTTCAATATCAAGGATTACTATCTGC<br>ACTGGGTGCGTCAGGCGCCAGGTCAGGCCTTGGAATGGATGGGCTGGATTGAC<br>CCGGATCAAGGTGACACCGAATATGCCCAAAAGTTTCAGGGTCGTGTGACCAT<br>CACCCGTGACCGTAGCACCTCCACCGCATATATGGAGCTGCGTAGCCTGCGCA<br>GCGAAGATACTGCGGTGTATTACTGCAATGCGGCCTATGGTAGCAGCTCCTAT<br>CCGATGGATTACTGGGGCCAGGGTACCACGGTGACGGTTAGCAGCGCAAGCAC<br>CAAGGGCCCGAGCGTTTTCCCTCTGGCGCCGAGCAGCAAAAGCACTAGCGGCG<br>GTACGGCAGCCCTGGGTTGTCTGGTTAAAGATTACTTTCCGGAACCGGTTACC<br>GTGTCCTGGAACTCTGGCGCGCTGACCAGCGGTGTTCACACGTTTCCGGCGGT<br>TCTGCAGAGCAGCGGTCTGTATTCTTTGAGCTCCGTCGTCACCGTCCCGTCTA<br>GCTCGCTGGGCACGCAGACGTACATCTGCAATGTTAACCATAAGCCGAGCAAT<br>ACCAAAGTTGACAAGAAAGTCGAACCTAAGAGCTGTGATAAGACGCATACCTG<br>TCCGCCGTGCCCGGCACCGGAACTGTTGGGCGGTCCGAGCGTGTTCCTGTTTC<br>CGCCGAAGCCGAAAGATACCCTGATGATTAGCCGCACCCCTGAGGTGACGTGC<br>GTGGTTGTGGACGTTAGCCATGAGGATCCAGAGGTCAAATTCAATTGGTATGT<br>CGATGGTGTTGAGGTTCACAATGCCAAGACCAAACCGCGTGAAGAACAGTACA<br>ATAGCACCTACCGCGTGGTGAGCGTGCTGACGGTCCTGCACCAGGACTGGCTG<br>AACGGCAAAGAGTACAAGTGTAAGGTCAGCAACAAGGCGCTGCCAGCACCGAT<br>TGAAAAGACCATTTCTAAAGCGAAAGGTCAGCCGCGTGAGCCGCAAGTCTATA<br>CCCTGCCGCCGTCGCGCGATGAGCTGACTAAAAACCAGGTTAGCCTGACGTGC<br>CTGGTGAAAGGTTTCTACCCGAGCGACATCGCGGTGGAGTGGGAGAGCAACGG<br>TCAACCGGAGAATAACTACAAAACCACCCCACCGGTCTTGGACTCCGATGGCA<br>GCTTCTTTCTGTACTCTAAACTGACCGTTGACAAAAGCCGTTGGCAACAGGGC<br>AACGTCTTTAGCTGCAGCGTGATGCATGAGGCTCTGCACAACCACTACACCCA<br>AAAATCCCTGAGCCTGAGCCCGGGTAAGTAA |
| 29 | Anti-CD47 IgG4-13m HC:<br>ATGCAAGTCCAATTGGTCCAGAGCGGTGCGGAAGTCAAGAAACCGGGTGCAAG<br>CGTCAAAGTTTCGTGCAAGGCGAGCGGTTTCAATATCAAAGACTATTATCTGC<br>ACTGGGTTCGTCAGGCTCCGGGCCAAGGCCTGGAGTGGATGGGTTGGATCGAT<br>CCGGACCAGGGCGACACGGAGTACGCTCAGAAGCTGCAGGGTCGTGTTACCAT<br>GACCACCGACACCAGCACGAGCACCGCGTACATGGAACTGCGCTCTCTGCGTT<br>CGGATGATACCGCGGTGTACTATTGCAACGCCGCGTACGGTAGCAGCAGCTAT<br>CCGATGGATTATTGGGGTCAAGGCACTACGGTGACTGTCAGCAGCGCCAGCAC<br>CAAGGGCCCGTCTGTGTTTCCGTTGGCACCGTGCAGCCGTAGCACTAGCGAAT<br>CCACTGCAGCGCTGGGTTGCCTGGTTAAGGACTATTTCCCGGAGCCGGTTACC<br>GTGTCCTGGAACTCTGGCGCCCTGACCAGCGGTGTTCACACGTTTCCAGCCGT<br>CCTGCAGAGCAGCGGTCTGTACAGCCTGAGCTCGGTGGTGACCGTTCCGAGCA<br>GCTCTCTGGGTACCAAAACCTATACCTGTAATGTCGATCACAAACCGTCTAAC<br>ACGAAGGTCGATAAACGTGTTGAAAGCAAGTACGGTCCGCCTTGTCCGCCGTG<br>CCCGGCACCGGAGTTTCTGGGCGGTCCGTCCGTATTCCTGTTCCCGCCGAAAC<br>CGAAAGATACCTTGATGATTAGCCGTACGCCAGAGGTCACGTGCGTCGTGGTG<br>GACGTTAGCCAAGAGGATCCGGAAGTCCAATTCAACTGGTACGTGGACGGTGT<br>CGAGGTGCACAATGCCAAAACCAAGCCGCGTGAAGAACAGTTTAACAGCACTT<br>ACCGCGTCGTTAGCGTCCTGACCGTGCTGCACCAAGATTGGCTGAATGGTAAA<br>GAGTACAAGTGCAAGGTTAGCAATAAGGGTCTGCCGAGCAGCATCGAGAAAAC<br>CATTAGCAAGGCGAAAGGTCAACCGCGCGAGCCACAGGTCTACACGCTGCCGC<br>CGAGCCAAGAAGAAATGACCAAAAATCAGGTTAGCCTGACTTGTCTGGTGAAA<br>GGCTTCTACCCGAGCGATATTGCAGTTGAATGGGAGAGCAACGGCCAGCCTGA<br>GAACAACTATAAGACGACCCCGCCAGTGCTGGACAGCGATGGCAGCTTCTTTT<br>TGTATTCTCGTCTGACCGTGGACAAGTCCCGTTGGCAAGAGGGCAATGTGTTC<br>AGCTGTTCTGTCATGCACGAAGCGCTGCATAACCATTACACCCAGAAGTCCCT<br>GAGCCTGTCGCTGGGCAAATAA |
| 30 | Anti-CD47 IgG4P-5m HC:<br>ATGCAAATGCAATTGGTACAAAGCGGTGCGGAAGTAAAGAAACCGGGTTCGTC<br>GGTAAAGGTTAGCTGTAAAGCTTCTGGCTTCAATATCAAGGATTACTATCTGC<br>ACTGGGTGCGTCAGGCGCCAGGTCAGGCCTTGGAATGGATGGGCTGGATTGAC<br>CCGGATCAAGGTGACACCGAATATGCCCAAAAGTTTCAGGGTCGTGTGACCAT<br>CACCCGTGACCGTAGCACCTCCACCGCATATATGGAGCTGCGTAGCCTGCGCA<br>GCGAAGATACTGCGGTGTATTACTGCAATGCGGCCTATGGTAGCAGCTCCTAT<br>CCGATGGATTACTGGGGCCAGGGTACCACGGTGACGGTTAGCAGCGCAAGCAC<br>CAAGGGCCCGTCTGTGTTTCCGTTGGCACCGTGCAGCCGTAGCACTAGCGAAT<br>CCACTGCAGCGCTGGGTTGCCTGGTTAAGGACTATTTCCCGGAGCCGGTTACC<br>GTGTCCTGGAACTCTGGCGCCCTGACCAGCGGTGTTCACACGTTTCCAGCCGT<br>CCTGCAGAGCAGCGGTCTGTACAGCCTGAGCTCGGTGGTGACCGTTCCGAGCA<br>GCTCTCTGGGTACCAAAACCTATACCTGTAATGTCGATCACAAACCGTCTAAC<br>ACGAAGGTCGATAAACGTGTTGAAAGCAAGTACGGTCCGCCTTGTCCGCCGTG<br>CCCGGCACCGGAGTTTCTGGGCGGTCCGTCCGTATTCCTGTTCCCGCCGAAAC<br>CGAAAGATACCTTGATGATTAGCCGTACGCCAGAGGTCACGTGCGTCGTGGTG<br>GACGTTAGCCAAGAGGATCCGGAAGTCCAATTCAACTGGTACGTGGACGGTGT<br>CGAGGTGCACAATGCCAAAACCAAGCCGCGTGAAGAACAGTTTAACAGCACTT<br>ACCGCGTCGTTAGCGTCCTGACCGTGCTGCACCAAGATTGGCTGAATGGTAAA |

TABLE 2-continued

Anti-CD47 antibody VH and VL nucleotide sequences

| SEQ ID NO: | Nucleotide sequences |
|---|---|
| | GAGTACAAGTGCAAGGTTAGCAATAAGGGTCTGCCGAGCAGCATCGAGAAAAC<br>CATTAGCAAGGCGAAAGGTCAACCGCGCGAGCCACAGGTCTACACGCTGCCGC<br>CGAGCCAAGAAGAAATGACCAAAAATCAGGTTAGCCTGACTTGTCTGGTGAAA<br>GGCTTCTACCCGAGCGATATTGCAGTTGAATGGGAGAGCAACGGCCAGCCTGA<br>GAACAACTATAAGACGACCCCGCCAGTGCTGGACAGCGATGGCAGCTTCTTTT<br>TGTATTCTCGTCTGACCGTGGACAAGTCCCGTTGGCAAGAGGGCAATGTGTTC<br>AGCTGTTCTGTCATGCACGAAGCGCTGCATAACCATTACACCCAGAAGTCCCT<br>GAGCCTGTCGCTGGGCAAATAA |
| 31 | Anti-CD47 IgG4PE-13m HC:<br>ATGCAAGTCCAATTGGTCCAGAGCGGTGCGGAAGTCAAGAAACCGGGTGCAAG<br>CGTCAAAGTTTCGTGCAAGGCGAGCGGTTTCAATATCAAAGACTATTATCTGC<br>ACTGGGTTCGTCAGGCTCCGGGCCAAGGCCTGGAGTGGATGGGTTGGATCGAT<br>CCGGACCAGGGCGACACGGAGTACGCTCAGAAGCTGCAGGGTCGTGTTACCAT<br>GACCACCGACACCAGCACGAGCACCGCGTACATGGAACTGCGCTCTCTGCGTT<br>CGGATGATACCGCGGTGTACTATTGCAACGCCGCGTACGGTAGCAGCAGCTAT<br>CCGATGGATTATTGGGGTCAAGGCACTACGGTGACTGTCAGCAGCGCCAGCAC<br>CAAGGGCCCGTCTGTGTTTCCGTTGGCACCGTGCAGCCGTAGCACTAGCGAAT<br>CCACTGCAGCGCTGGGTTGCCTGGTTAAGGACTATTTCCCGGAGCCGGTTACC<br>GTGTCCTGGAACTCTGGCGCCCTGACCAGCGGTGTTCACACGTTTCCAGCCGT<br>CCTGCAGAGCAGCGGTCTGTACAGCCTGAGCTCGGTGGTGACCGTTCCGAGCA<br>GCTCTCTGGGTACCAAAACCTATACCTGTAATGTCGATCACAAACCGTCTAAC<br>ACGAAGGTCGATAAACGTGTTGAAAGCAAGTACGGTCCGCCTTGTCCGCCGTG<br>CCCCGGCACCGGAGTTTGAGGGCGGTCCGTCCGTATTCCTGTTCCCGCCGAAAC<br>CGAAAGATACCTTGATGATTAGCCGTACGCCAGAGGTCACGTGCGTCGTGGTG<br>GACGTTAGCCAAGAGGATCCGGAAGTCCAATTCAACTGGTACGTGGACGGTGT<br>CGAGGTGCACAATGCCAAAACCAAGCCGCGTGAAGAACAGTTTAACAGCACTT<br>ACCGCGTCGTTAGCGTCCTGACCGTGCTGCACCAAGATTGGCTGAATGGTAAA<br>GAGTACAAGTGCAAGGTTAGCAATAAGGGTCTGCCGAGCAGCATCGAGAAAAC<br>CATTAGCAAGGCGAAAGGTCAACCGCGCGAGCCACAGGTCTACACGCTGCCGC<br>CGAGCCAAGAAGAAATGACCAAAAATCAGGTTAGCCTGACTTGTCTGGTGAAA<br>GGCTTCTACCCGAGCGATATTGCAGTTGAATGGGAGAGCAACGGCCAGCCTGA<br>GAACAACTATAAGACGACCCCGCCAGTGCTGGACAGCGATGGCAGCTTCTTTT<br>TGTATTCTCGTCTGACCGTGGACAAGTCCCGTTGGCAAGAGGGCAATGTGTTC<br>AGCTGTTCTGTCATGCACGAAGCGCTGCATAACCATTACACCCAGAAGTCCCT<br>GAGCCTGTCGCTGGGCAAATAA |
| 32 | Anti-CD47 IgG4PE-5m HC:<br>ATGCAAATGCAATTGGTACAAAGCGGTGCGGAAGTAAAGAAACCGGGTTCGTC<br>GGTAAAGGTTAGCTGTAAAGCTTCTGGCTTCAATATCAAGGATTACTATCTGC<br>ACTGGGTGCGTCAGGCGCCAGGTCAGGCCTTGGAATGGATGGGCTGGATTGAC<br>CCGGATCAAGGTGACACCGAATATGCCCAAAAGTTTCAGGGTCGTGTGACCAT<br>CACCCGTGACCGTAGCACCTCCACCGCATATATGGAGCTGCGTAGCCTGCGCA<br>GCGAAGATACTGCGGTGTATTACTGCAATGCGGCCTATGGTAGCAGCTCCTAT<br>CCGATGGATTACTGGGGCCAGGGTACCACGGTGACGGTTAGCAGCGCAAGCAC<br>CAAGGGCCCGTCTGTGTTTCCGTTGGCACCGTGCAGCCGTAGCACTAGCGAAT<br>CCACTGCAGCGCTGGGTTGCCTGGTTAAGGACTATTTCCCGGAGCCGGTTACC<br>GTGTCCTGGAACTCTGGCGCCCTGACCAGCGGTGTTCACACGTTTCCAGCCGT<br>CCTGCAGAGCAGCGGTCTGTACAGCCTGAGCTCGGTGGTGACCGTTCCGAGCA<br>GCTCTCTGGGTACCAAAACCTATACCTGTAATGTCGATCACAAACCGTCTAAC<br>ACGAAGGTCGATAAACGTGTTGAAAGCAAGTACGGTCCGCCTTGTCCGCCGTG<br>CCCCGGCACCGGAGTTTGAGGGCGGTCCGTCCGTATTCCTGTTCCCGCCGAAAC<br>CGAAAGATACCTTGATGATTAGCCGTACGCCAGAGGTCACGTGCGTCGTGGTG<br>GACGTTAGCCAAGAGGATCCGGAAGTCCAATTCAACTGGTACGTGGACGGTGT<br>CGAGGTGCACAATGCCAAAACCAAGCCGCGTGAAGAACAGTTTAACAGCACTT<br>ACCGCGTCGTTAGCGTCCTGACCGTGCTGCACCAAGATTGGCTGAATGGTAAA<br>GAGTACAAGTGCAAGGTTAGCAATAAGGGTCTGCCGAGCAGCATCGAGAAAAC<br>CATTAGCAAGGCGAAAGGTCAACCGCGCGAGCCACAGGTCTACACGCTGCCGC<br>CGAGCCAAGAAGAAATGACCAAAAATCAGGTTAGCCTGACTTGTCTGGTGAAA<br>GGCTTCTACCCGAGCGATATTGCAGTTGAATGGGAGAGCAACGGCCAGCCTGA<br>GAACAACTATAAGACGACCCCGCCAGTGCTGGACAGCGATGGCAGCTTCTTTT<br>TGTATTCTCGTCTGACCGTGGACAAGTCCCGTTGGCAAGAGGGCAATGTGTTC<br>AGCTGTTCTGTCATGCACGAAGCGCTGCATAACCATTACACCCAGAAGTCCCT<br>GAGCCTGTCGCTGGGCAAATAA |
| 33 | Anti-CD47 IgK:<br>ATGAACATCCAAATGACTCAATCCCCATCCGCAATGTCCGCATCCGTAGGTGA<br>CCGCGTGACCATCACGTGCAAGGCGAGCCAGGATATTCATCGTTATCTGAGCT<br>GGTTTCAACAGAAACCGGGCAAGGTTCCTAAGCATCTGATTTACCGCGCGAAC<br>CGCTTGGTTAGCGGTGTTCCGAGCCGTTTTAGCGGCAGCGGTTCTGGCACCGA<br>GTTCACCCTGACGATCTCCAGCCTGCAACCGGAAGATTTTGCGACGTACTACT<br>GCCTGCAGTATGACGAGTTCCCGTATACCTTTGGTGGTGGTACGAAGGTGGAA<br>ATCAAACGTACTGTGGCCGCTCCGAGCGTTTTCATTTTTCCGCCGTCGGATGA<br>GCAATTGAAATCTGGTACCGCGAGCGTCGTTTGTCTGCTGAACAATTTCTACC<br>CGCGTGAGGCTAAGGTGCAATGGAAGGTCGATAACGCGCTGCAGAGCGGTAAT |

TABLE 2-continued

Anti-CD47 antibody VH and VL nucleotide sequences

| SEQ ID NO: | Nucleotide sequences |
|---|---|
| | AGCCAGGAAAGCGTCACCGAACAGGATAGCAAAGACAGCACCTACTCTTTGAG<br>CAGCACCCTGACCCTGAGCAAGGCCGACTATGAGAAACACAAAGTTTACGCAT<br>GTGAGGTCACGCACCAGGGCCTGAGCAGCCCGGTGACCAAAAGCTTCAATCGT<br>GGCGAATGCTAA |

In certain embodiments, a polynucleotide provided herein is operably linked to a promoter for expression of such polynucleotide sequence in a host cell. In certain embodiments, the promoter is derived form the genome of mammalian cells (e.g., metallothionein promoter) or from mammalian viruses (e.g., the adenovirus late promoter, the vaccinia virus 7.5K promoter). In a specific embodiment, the expression of nucleotide sequences encoding antibodies described herein is regulated by a constitutive promoter, inducible promoter or tissue specific promoter.

In specific aspects, provided herein is a polynucleotide comprising a nucleotide sequence encoding an antibody comprising a light chain and a heavy chain, e.g., a separate light chain and heavy chain. With respect to the light chain, in a specific embodiment, a polynucleotide provided herein comprises a nucleotide sequence encoding a kappa light chain. In another specific embodiment, a polynucleotide provided herein comprises a nucleotide sequence encoding a lambda light chain. In yet another specific embodiment, a polynucleotide provided herein comprises a nucleotide sequence encoding an antibody described herein comprising a human kappa light chain or a human lambda light chain. For example, human constant region sequences can be those described in U.S. Pat. No. 5,693,780.

In a particular embodiment, a polynucleotide provided herein comprises a nucleotide sequence encoding an antibody described herein, which immunospecifically binds to a CD47 polypeptide, wherein the antibody comprises a heavy chain, wherein the constant region of the heavy chain comprises the amino acid sequence of a human gamma (γ) heavy chain constant region, for example, human gamma (γ) 1 heavy chain constant region, human gamma (γ) 2 heavy chain constant region, human gamma (γ) 3 heavy chain constant region, or human gamma (γ) 4 heavy chain constant region.

5.2.2 Cells and Vectors

In certain aspects, provided herein are cells (e.g., host cells) expressing (e.g., recombinantly) antibodies described herein (or an antigen-binding fragment thereof) which specifically bind to CD47 and related polynucleotides and expression vectors, for example, polynucleotides and expression vectors suitable for use in CF expression systems. Provided herein are vectors (e.g., expression vectors) comprising polynucleotides comprising nucleotide sequences encoding anti-CD47 antibodies or a fragment for recombinant expression in CF expression systems. In a particular aspect, provided herein are methods for producing an anti-CD47 antibody described herein, comprising expressing such an antibody using a CF expression system, for example, under conditions resulting in improved antibody expression titer or yield.

In certain aspects, provided herein are vectors (e.g., expression vectors) comprising polynucleotides comprising nucleotide sequences encoding anti-CD47 antibodies or a fragment for recombinant expression in host cells, e.g., in mammalian cells. Also provided herein are host cells comprising such vectors for recombinantly expressing anti-CD47 antibodies described herein (e.g., human or humanized antibody). In a particular aspect, provided herein are methods for producing an antibody described herein, comprising expressing such an antibody using host cells.

Recombinant expression of an antibody described herein (e.g., a full-length antibody, heavy and/or light chain of an antibody, or a single chain antibody described herein) that specifically binds to CD47 involves construction of an expression vector containing a polynucleotide that encodes the antibody. Once a polynucleotide encoding an antibody molecule, heavy and/or light chain of an antibody, or a fragment thereof (e.g., heavy and/or light chain variable domains) described herein has been obtained, the vector for the production of the antibody molecule can be produced by recombinant DNA technology using techniques well-known in the art. Thus, methods for preparing a protein by expressing a polynucleotide containing an antibody or antibody fragment (e.g., light chain or heavy chain) encoding nucleotide sequence are described herein. Methods which are well known to those skilled in the art can be used to construct expression vectors containing antibody or antibody fragment (e.g., light chain or heavy chain) coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody molecule described herein, a heavy or light chain of an antibody, a heavy or light chain variable domain of an antibody or a fragment thereof, or a heavy or light chain CDR, operably linked to a promoter. Such vectors can, for example, include the nucleotide sequence encoding the constant region of the antibody molecule (see, e.g., International Publication Nos. WO 86/05807 and WO 89/01036; and U.S. Pat. No. 5,122,464) and variable domains of the antibody can be cloned into such a vector for expression of the entire heavy, the entire light chain, or both the entire heavy and light chains.

An expression vector can be transferred to a cell (e.g., host cell) by conventional techniques and the resulting cells can then be cultured by conventional techniques to produce an antibody described herein or a fragment thereof. Thus, provided herein are host cells containing a polynucleotide encoding an antibody described herein or fragments thereof, or a heavy or light chain thereof, or fragment thereof, or a single chain antibody described herein, operably linked to a promoter for expression of such sequences in the host cell. In certain embodiments, for the expression of double-chained antibodies, vectors encoding both the heavy and light chains, individually, can be co-expressed in the host cell for expression of the entire immunoglobulin molecule, as detailed below. In certain embodiments, a host cell contains a vector comprising a polynucleotide encoding both the heavy chain and light chain of an antibody described herein, or a fragment thereof. In specific embodiments, a host cell contains two different vectors, a first vector comprising a polynucleotide encoding a heavy chain or a heavy chain variable region of an antibody described herein, or a fragment thereof, and a second vector comprising a polynucleotide encoding a light chain or a light chain variable region of an antibody described herein, or a fragment thereof. In other embodiments, a first host cell comprises a first vector comprising a polynucleotide encoding a heavy chain or a heavy chain variable region of an antibody described herein, or a fragment thereof, and a second host cell comprises a second vector comprising a polynucleotide encoding a light chain or a light chain variable region of an antibody described herein. In specific embodiments, a heavy chain/heavy chain variable region expressed by a first cell associated with a light chain/light chain variable region of a second cell to form an anti-CD47 antibody described herein or an antigen-binding fragment thereof. In certain embodiments, provided herein is a population of host cells comprising such first host cell and such second host cell.

In a particular embodiment, provided herein is a population of vectors comprising a first vector comprising a polynucleotide encoding a light chain/light chain variable region of an anti-CD47 antibody described herein, and a second vector comprising a polynucleotide encoding a heavy chain/heavy chain variable region of an anti-CD47 antibody described herein.

A variety of host-expression vector systems can be utilized to express antibody molecules described herein (see, e.g., U.S. Pat. No. 5,807,715). Such host-expression systems represent vehicles by which the coding sequences of interest can be produced and subsequently purified, but also represent cells which can, when transformed or transfected with the appropriate nucleotide coding sequences, express an antibody molecule described herein in situ. These include but are not limited to microorganisms such as bacteria (e.g., E. coli and B. subtilis) transformed with recombinant bacteriophage DNA, plasmid DNA or cosmid DNA expression vectors containing antibody coding sequences; yeast (e.g., Saccharomyces Pichia) transformed with recombinant yeast expression vectors containing antibody coding sequences; insect cell systems infected with recombinant virus expression vectors (e.g., baculovirus) containing antibody coding sequences; plant cell systems (e.g., green algae such as Chlamydomonas reinhardtii) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, MDCK, HEK 293, NS0, PER.C6, VERO, CRL7O3O, HsS78Bst, HeLa, and NIH 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing antibodies described herein or an antigen-binding fragment thereof are CHO cells, for example CHO cells from the CHO GS System™ (Lonza). In a specific embodiment, a mammalian expression vector is pOptiVEC™ or pcDNA3.3. In a particular embodiment, bacterial cells such as Escherichia coli, or eukaryotic cells (e.g., mammalian cells), especially for the expression of whole recombinant antibody molecule, are used for the expression of a recombinant antibody molecule. For example, mammalian cells such as Chinese hamster ovary (CHO) cells, in conjunction with a vector such as the major intermediate early gene promoter element from human cytomegalovirus is an effective expression system for antibodies (Foecking et al., 1986, Gene 45:101; and Cockett et al., 1990, Bio/Technology 8:2). In certain embodiments, antibodies described herein are produced by CHO cells or NS0 cells. In a specific embodiment, the expression of nucleotide sequences encoding antibodies described herein which immunospecifically bind to CD47 is regulated by a constitutive promoter, inducible promoter or tissue specific promoter.

In bacterial systems, a number of expression vectors can be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified can be desirable. Such vectors include, but are not limited to, the E. coli expression vector pUR278 (Ruther et al., 1983, EMBO 12:1791), in which the antibody coding sequence can be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. For example, pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhedrosis virus (AcNPV), for example, can be used as a vector to express foreign genes. The virus grows in Spodoptera frugiperda cells. The antibody coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, Proc. Natl. Acad. Sci. USA 8 1:355-359). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bittner et al., 1987, Methods in Enzymol. 153:51-544).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, COS, MDCK, HEK 293, NIH 3T3, W138, BT483, Hs578T, HTB2, BT2O and T47D, NS0 (a murine myeloma cell line that does not endogenously produce any immunoglobulin chains), CRL7O3O and HsS78Bst cells. In certain embodiments, anti-CD47 antibodies described herein (e.g., an antibody comprising the CDRs of any one of antibodies Ab235-Ab255) are produced in mammalian cells, such as CHO cells.

For long-term, high-yield production of recombinant proteins, stable expression cells can be generated. For example, cell lines which stably express an anti-CD47 antibody described herein or an antigen-binding fragment thereof can be engineered. In specific embodiments, a cell provided herein stably expresses a light chain/light chain variable domain and a heavy chain/heavy chain variable domain which associate to form an antibody described herein or an antigen-binding fragment thereof.

In certain aspects, rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA/polynucleotide, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express an anti-CD47 antibody described herein or a fragment thereof. Such engineered cell lines can be particularly useful in screening and evaluation of compositions that interact directly or indirectly with the antibody molecule.

A number of selection systems can be used, including but not limited to, the herpes simplex virus thymidine kinase (Wigler et al., 1977, Cell 11:223), hypoxanthineguanine phosphoribosyltransferase (Szybalska & Szybalski, 1992, Proc. Natl. Acad. Sci. USA 48:202), and adenine phosphoribosyltransferase (Lowy et al., 1980, Cell 22:8-17) genes can be employed in tk-, hgprt- or aprt-cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIB TECH 11(5):155-2 15); and hygro, which confers resistance to hygromycin (Santerre et al., 1984, Gene 30:147). Methods commonly known in the art of recombinant DNA technology can be routinely applied to select the desired recombinant clone, and such methods are described, for example, in Ausubel et al. (eds.), *Current Protocols in Molecular Biology*, John Wiley & Sons, N Y (1993); Kriegler, *Gene Transfer and Expression*, A Laboratory Manual, Stockton Press, N Y (1990); and in Chapters 12 and 13, Dracopoli et al. (eds.), *Current Protocols in Human Genetics*, John Wiley & Sons, N Y (1994); Colberre-Garapin et al., 1981, J. Mol. Biol. 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3 (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell can be co-transfected with two or more expression vectors described herein, the first vector encoding a heavy chain derived polypeptide and the second vector encoding a light chain derived polypeptide. The two vectors can contain identical selectable markers which enable equal expression of heavy and light chain polypeptides. The host cells can be co-transfected with different amounts of the two or more expression vectors. For example, host cells can be transfected with any one of the following ratios of a first expression vector and a second expression vector: 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, or 1:50.

Alternatively, a single vector can be used which encodes, and is capable of expressing, both heavy and light chain polypeptides. In such situations, the light chain should be placed before the heavy chain to avoid an excess of toxic free heavy chain (Proudfoot, 1986, Nature 322:52; and Kohler, 1980, Proc. Natl. Acad. Sci. USA 77:2197-2199). The coding sequences for the heavy and light chains can comprise cDNA or genomic DNA. The expression vector can be monocistronic or multicistronic. A multicistronic nucleic acid construct can encode 2, 3, 4, 5, 6, 7, 8, 9, 10 or more, or in the range of 2-5, 5-10 or 10-20 genes/nucleotide sequences. For example, a bicistronic nucleic acid construct can comprise in the following order a promoter, a first gene (e.g., heavy chain of an antibody described herein), and a second gene and (e.g., light chain of an antibody described herein). In such an expression vector, the transcription of both genes can be driven by the promoter, whereas the translation of the mRNA from the first gene can be by a cap-dependent scanning mechanism and the translation of the mRNA from the second gene can be by a cap-independent mechanism, e.g., by an IRES.

Once an antibody molecule described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies described herein can be fused to heterologous polypeptide sequences described herein or otherwise known in the art to facilitate purification.

In specific embodiments, an antibody or antigen-binding fragment described herein is isolated or purified. Generally, an isolated antibody is one that is substantially free of other antibodies with different antigenic specificities than the isolated antibody. For example, in a particular embodiment, a preparation of an antibody described herein is substantially free of cellular material and/or chemical precursors. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") and/or variants of an antibody, for example, different post-translational modified forms of an antibody or other different versions of an antibody (e.g., antibody fragments). When the antibody is recombinantly produced, it is also generally substantially free of culture medium, i.e., culture medium represents less than about 20%, 10%, 2%, 1%, 0.5%, or 0.1% of the volume of the protein preparation. When the antibody is produced by chemical synthesis, it is generally substantially free of chemical precursors or other chemicals, i.e., it is separated from chemical precursors or other chemicals which are involved in the synthesis of the protein. Accordingly, such preparations of the antibody have less than about 30%, 20%, 10%, or 5% (by dry weight) of chemical precursors or compounds other than the antibody of interest. In a specific embodiment, antibodies described herein are isolated or purified.

5.3 Pharmaceutical Compositions and Kits

Provided herein are compositions, pharmaceutical compositions, and kits comprising one or more antibodies (e.g., anti-CD47 antibodies) described herein, or antigen-binding fragments thereof, or conjugates thereof. In particular aspects, compositions (e.g., pharmaceutical compositions) described herein can be for in vitro, in vivo, or ex vivo uses. Non-limiting examples of uses include uses to modulate (e.g., inhibit or induce/enhance) CD47 activity and uses to manage or treat a disorder, for example, cancer. In specific embodiments, provided herein is a pharmaceutical composition comprising an antibody (e.g., a humanized antibody) described herein (or an antigen-binding fragment thereof) and a pharmaceutically acceptable carrier or excipient.

As used herein, the term "pharmaceutically acceptable" means being approved by a regulatory agency of the Federal or a state government, or listed in the U.S. Pharmacopeia, European Pharmacopeia or other generally recognized Pharmacopeia for use in animals, and more particularly in humans.

Formulations containing one or more antibodies provided herein or an antigen-binding fragment thereof can be prepared for storage by mixing the antibody having the desired degree of purity with optional physiologically acceptable carriers, excipients or stabilizers (*Remington's Pharmaceutical Sciences* (1990) Mack Publishing Co., Easton, Pa.; *Remington: The Science and Practice of Pharmacy*, 21st ed. (2006) Lippincott Williams & Wilkins, Baltimore, Md.). Such formulations can, for example, be in the form of, e.g., lyophilized formulations or aqueous solutions. Pharmaceutical carriers suitable for administration of the antibodies provided herein include any such carriers known to those skilled in the art to be suitable for the particular mode of administration. Acceptable carriers, excipients, or stabilizers are nontoxic to recipients at the dosages and concentrations employed, and include buffers such as phosphate, citrate, and other organic acids; and/or non-ionic surfactants such as TWEEN™, PLURONICS™ or polyethylene glycol (PEG).

Formulations to be used for in vivo administration can be sterile. This can be readily accomplished, for example, by filtration through, e.g., sterile filtration membranes.

In specific aspects, the pharmaceutical compositions provided herein contain therapeutically effective amounts of one or more of the antibodies or antigen-binding fragments provided herein in a pharmaceutically acceptable carrier. Such pharmaceutical compositions are useful in the prevention, treatment, management or amelioration of a condition or disorder described herein or one or more symptoms thereof.

Compositions provided herein can contain one or more antibodies provided herein or an antigen-binding fragment thereof. In one embodiment, compositions are provided wherein antibodies or antigen-binding fragments described herein are formulated into suitable pharmaceutical preparations, such as solutions, suspensions, powders, sustained release formulations or elixirs in sterile solutions or suspensions for parenteral administration, or as transdermal patch preparation and dry powder inhalers.

In one embodiment, compositions provided herein are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

In certain aspects, an antibody provided herein is included in the pharmaceutically acceptable carrier in an effective amount sufficient to exert a therapeutically useful effect in the absence of, or with minimal or negligible, undesirable side effects on the patient treated.

Concentrations of anti-CD47 antibody in a pharmaceutical composition provided herein will depend on, e.g., the physicochemical characteristics of the antibody, the dosage schedule, and amount administered as well as other factors.

Pharmaceutical compositions described herein are provided for administration to humans or animals (e.g., mammals) in unit dosage forms, such as sterile parenteral (e.g., intravenous) solutions or suspensions containing suitable quantities of the compounds or pharmaceutically acceptable derivatives thereof. Pharmaceutical compositions are also provided for administration to humans and animals in unit dosage form, such as tablets, capsules, pills, powders, granules, and oral or nasal solutions or suspensions, and oil-water emulsions containing suitable quantities of an anti-CD47 antibody or pharmaceutically acceptable derivatives thereof. The antibody is, in one embodiment, formulated and administered in unit-dosage forms or multiple-dosage forms. Unit-dose forms as used herein refers to physically discrete units suitable for human or animal (e.g., mammal) subjects and packaged individually. Each unit-dose contains a predetermined quantity of an anti-CD47 antibody sufficient to produce the desired therapeutic effect, in association with the required pharmaceutical carrier, vehicle or diluent. Examples of unit-dose forms include ampoules and syringes and individually packaged tablets or capsules. Unit-dose forms can be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles. Hence, in specific aspects, multiple dose form is a multiple of unit-doses which are not segregated in packaging.

In certain embodiments, one or more anti-CD47 antibodies described herein or an antigen-binding fragment thereof are in a liquid pharmaceutical formulation. Liquid pharmaceutically administrable compositions can, for example, be prepared by dissolving, dispersing, or otherwise mixing an antibody and optional pharmaceutical adjuvants in a carrier, such as, for example, water, saline, aqueous dextrose, glycerol, glycols, and the like, to thereby form a solution or suspension. In certain embodiments, a pharmaceutical composition provided herein to be administered can also contain minor amounts of nontoxic auxiliary substances such as wetting agents, emulsifying agents, solubilizing agents, and pH buffering agents and the like.

Methods of preparing such dosage forms are known, or will be apparent, to those skilled in this art; for example, see, e.g., *Remington's Pharmaceutical Sciences* (1990) Mack Publishing Co., Easton, Pa.; *Remington: The Science and Practice of Pharmacy*, 21st ed. (2006) Lippincott Williams & Wilkins, Baltimore, Md.

Parenteral administration, in one embodiment, is characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. Other routes of administration may include, enteric administration, intracerebral administration, nasal administration, intraarterial administration, intracardiac administration, intraosseous infusion, intrathecal administration, and intraperitoneal administration.

Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions can be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Pharmaceutical carriers also include ethyl alcohol, polyethylene glycol and propylene glycol for water miscible vehicles; and sodium hydroxide, hydrochloric acid, citric acid or lactic acid for pH adjustment.

In certain embodiments, intravenous or intraarterial infusion of a sterile aqueous solution containing an anti-CD47 antibody or fragment described herein is an effective mode of administration. Another embodiment is a sterile aqueous or oily solution or suspension containing an anti-CD47 antibody described herein injected as necessary to produce the desired pharmacological effect.

In specific embodiments, an anti-CD47 antibody described herein can be suspended in micronized or other suitable form. The form of the resulting mixture depends upon a number of factors, including the intended mode of administration and the solubility of the compound in the selected carrier or vehicle.

In other embodiments, the pharmaceutical formulations are lyophilized powders, which can be reconstituted for administration as solutions, emulsions and other mixtures. They can also be reconstituted and formulated as solids or gels.

Lyophilized powder can, for example, be prepared by dissolving an anti-CD47 antibody provided herein, in a suitable solvent. In some embodiments, the lyophilized powder is sterile. Suitable solvents can contain an excipient which improves the stability or other pharmacological component of the powder or reconstituted solution, prepared from the powder. Excipients that can be used include, but are not limited to, dextrose, sorbital, fructose, corn syrup, xylitol, glycerin, glucose, sucrose or other suitable agent. A suitable solvent can also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides an example of a formulation. In one embodiment, the resulting solution will be apportioned into vials for lyophilization. Lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier.

In certain aspects, anti-CD47 antibodies provided herein can be formulated for local administration or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

Anti-CD47 antibodies and other compositions provided herein can also be formulated to be targeted to a particular tissue, organ, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874. In some embodiments, anti-CD47 antibodies described herein are targeted (or otherwise administered) to the visual organs, bone marrow, gastrointestinal tract, lungs, brain, or joints. In specific embodiments, an anti-CD47 antibody described herein is capable of crossing the blood-brain barrier.

Provided herein is a pharmaceutical pack or kit comprising one or more containers filled with one or more of the ingredients of the pharmaceutical compositions described herein, such as one or more anti-CD47 antibodies provided herein. Optionally associated with such container(s) can be a notice in the form prescribed by a governmental agency regulating the manufacture, use or sale of pharmaceuticals or biological products, which notice reflects approval by the agency of manufacture, use or sale for human administration.

Also provided herein are kits comprising one or more of the antibodies or antibody fragments described herein. In one embodiment, a kit comprises an antibody or antibody fragment described herein, in one or more containers. In a specific embodiment, kits described herein contain a substantially purified CD47 antigen as a control. In another specific embodiment, the kits described herein further comprise a control antibody which does not react with a CD47 antigen. In another specific embodiment, kits described herein contain one or more elements for detecting the binding of a modified antibody to a CD47 antigen (e.g., the antibody can be conjugated to a detectable substrate such as a fluorescent compound, an enzymatic substrate, a radioactive compound or a luminescent compound, or a second antibody which recognizes the first antibody can be conjugated to a detectable substrate). In specific embodiments, a kit provided herein can include a recombinantly produced or chemically synthesized CD47 antigen. The CD47 antigen provided in the kit can also be attached to a solid support. In a more specific embodiment, the detecting means of the above described kit includes a solid support to which a CD47 antigen is attached. Such a kit can also include a non-attached reporter-labeled anti-human antibody or anti-mouse/rat antibody. In this embodiment, binding of the antibody to the CD47 antigen can be detected by binding of the said reporter-labeled antibody.

5.4 Uses and Methods

In particular aspects, provided herein are methods of modulating CD47 activity with an anti-CD47 antibody or an antigen-binding fragment thereof described herein.

In specific embodiments, provided herein are methods of inhibiting (e.g., partially inhibiting) a CD47 activity with an anti-CD47 antibody described herein. In certain embodiments, provided herein are methods of managing or treating a condition or disorder, such as cancer, using an anti-CD47 antibody described herein. In certain embodiments, provided herein are methods of protecting against a condition or disorder, such as cancer, using an anti-CD47 antibody described herein.

In particular embodiments, provided herein are methods for managing, treating, preventing or protecting against cancer, comprising administering to a subject in need thereof a therapeutically effective amount of an antibody or an antigen-binding fragment described herein that binds specifically to CD47 (e.g., human CD47). In certain embodiments, provided herein is a method of alleviating, inhibiting or reducing the progression or severity of one or more symptoms associated with cancer.

As used herein, "administer" or "administration" refers to the act of injecting or otherwise physically delivering a substance (e.g., a humanized anti-CD47 antibody provided herein or an antigen-binding fragment thereof) to a subject or a patient (e.g., human), such as by mucosal, topical, intradermal, parenteral, intravenous, subcutaneous, intramuscular delivery and/or any other method of physical delivery described herein or known in the art.

As used herein, the terms "effective amount" or "therapeutically effective amount" refer to an amount of a therapy (e.g., an antibody or pharmaceutical composition provided herein) which is sufficient to reduce and/or ameliorate the severity and/or duration of a given condition, disorder or disease (e.g., cancer, metastasis, or angiogenesis) and/or a symptom related thereto. These terms also encompass an amount necessary for the reduction, slowing, or amelioration of the advancement or progression of a given disease, reduction, slowing, or amelioration of the recurrence, development or onset of a given disease, and/or to improve or enhance the prophylactic or therapeutic effect(s) of another therapy (e.g., a therapy other than an anti-CD47 antibody provided herein). In some embodiments, "effective amount" as used herein also refers to the amount of an antibody described herein to achieve a specified result.

As used herein, the term "in combination" in the context of the administration of other therapies refers to the use of more than one therapy. The use of the term "in combination" does not restrict the order in which therapies are administered. The therapies may be administered, e.g., serially, sequentially, concurrently, or concomitantly.

As used herein, the terms "manage," "managing," and "management" refer to the beneficial effects that a subject derives from a therapy (e.g., a prophylactic or therapeutic agent), which does not result in a cure of a condition associated with CD47. In certain embodiments, a subject is administered one or more therapies (e.g., prophylactic or therapeutic agents, such as an antibody described herein) to "manage" a condition or disorder described herein, one or more symptoms thereof, so as to prevent the progression or worsening of the condition or disorder.

As used herein, the terms "impede" or "impeding" in the context of a condition or disorder provided herein (e.g., autoimmune disorder, immunological disorder, cancer, or inflammation) refer to the total or partial inhibition (e.g., less than 100%, 95%, 90%, 80%, 70%, 60%, 50%, 40%, 30%, 20%, 10%, or 5%) or blockage of the development, recurrence, onset or spread of a condition or disorder provided herein (e.g., cancer, metastasis, or angiogenesis) and/or symptom related thereto, resulting from the administration of a therapy or combination of therapies provided herein (e.g., a combination of prophylactic or therapeutic agents, such as an antibody described herein).

As used herein, the terms "subject" and "patient" are used interchangeably. As used herein, a subject is a mammal such as a non-primate (e.g., cows, pigs, horses, cats, dogs, goats, rabbits, rats, mice, etc.) or a primate (e.g., monkey and human), for example a human. In one embodiment, the subject is a mammal, e.g., a human, diagnosed with a condition or disorder provided herein (e.g., cancer, metastasis, or angiogenesis). In another embodiment, the subject is a mammal, e.g., a human, at risk of developing a condition or disorder provided herein (e.g., cancer, metastasis, or angiogenesis). In another embodiment, the subject is human.

In certain embodiments, CD47 is amplified in cells of a subject, e.g., the human subject. Identification of cd47 amplification in a sample from a subject can be performed by assays known to one of ordinary skill in the art, such as, e.g., quantitative reverse transcription PCR, immunoblot assays, DNA fingerprinting, karyotyping (for example, by multicolor fluorescence in situ hybridization (mFISH)), comparative genome hybridization, and gene expression profiling. As a non-limiting example, protein expression of tumor samples can be characterized using immunohistochemical assays to measure the amount of CD47 protein present in a sample.

Identification of mutations or deltions in a sample from a subject can be performed by assays known to one of ordinary skill in the art, such as, e.g., DNA extraction, generation of complementary DNA, and cDNA sequencing. The cDNA sequence, for example, can be utilized to obtain the translation product by methods known to one of ordinary skill in the art. Genetic deletions and amino acid substitutions can be identified by, for example, comparing the sequence from the sample from the subject to a a wild type and/or consensus sequence.

In certain embodiments, CD47 is amplified in the subject treated in accordance with the methods provided herein. Identification of CD47 amplification in a sample from a subject is performed by assays known to one of ordinary skill in the art, such as, e.g., quantitative reverse transcription PCR or immunoblot assays. Identification of mutations or deletions in a sample from a subject are performed by assays known to one of ordinary skill in the art, such as, e.g., DNA extraction, generation of complementary DNA, and cDNA sequencing. The cDNA sequence, for example, is utilized to obtain the translation product by methods known to one of ordinary skill in the art. Genetic deletions and amino acid substitutions are identified by, for example, comparing the sequence from the sample from the subject to a a wild type and/or consensus sequence.

As used herein, the terms "therapies" and "therapy" can refer to any protocol(s), method(s), compositions, formulations, and/or agent(s) that can be used in the prevention, treatment, management, or amelioration of a condition or disorder or symptom thereof (e.g., a condition or disorder provided herein (e.g., cancer) or one or more symptoms or condition associated therewith). In certain embodiments, the terms "therapies" and "therapy" refer to drug therapy, adjuvant therapy, radiation, surgery, biological therapy, supportive therapy, and/or other therapies useful in treatment, management, prevention, or amelioration of a condition or disorder or one or more symptoms thereof (e.g., cancer or one or more symptoms or condition associated therewith). In certain embodiments, the term "therapy" refers to a therapy other than an anti-CD47 antibody described herein or pharmaceutical composition thereof. In specific embodiments, an "additional therapy" and "additional therapies" refer to a therapy other than a treatment using an anti-CD47 antibody described herein or pharmaceutical composition thereof. In a specific embodiment, a therapy includes the use of an anti-CD47 antibody described herein as an adjuvant therapy. For example, using an anti-CD47 antibody described herein in conjunction with a drug therapy, biological therapy, surgery, and/or supportive therapy.

As used herein, "hematological cancer" refers to a cancer of the blood, and includes leukemia, lymphoma and myeloma among others. "Leukemia" refers to a cancer of the blood in which too many white blood cells that are ineffective in fighting infection are made, thus crowding out the other parts that make up the blood, such as platelets and red blood cells. It is understood that cases of leukemia are classified as acute or chronic. Certain forms of leukemia include, by way of non-limiting example, acute lymphocytic leukemia (ALL); acute myeloid leukemia (AML); chronic lymphocytic leukemia (CLL); chronic myelogenous leukemia (CML); Myeloproliferative disorder/neoplasm (MPDS); and myelodysplasia syndrome. "Lymphoma" may refer to a Hodgkin's lymphoma, both indolent and aggressive non-Hodgkin's lymphoma, Burkitt's lymphoma, and follicular lymphoma (small cell and large cell), among others. Myeloma may refer to multiple myeloma (MM), giant cell myeloma, heavy-chain myeloma, and light chain or Bence-Jones myeloma.

Non-limiting examples of a condition which can be treated or managed with an anti-CD47 antibody described herein include hematological caner and/or solid tumors.

Diseases or disorders related to aberrant CD47 expression, activity and/or signaling include, by way of non-limiting example, hematological cancer and/or solid tumors. Hematological cancers include, e.g., leukemia, lymphoma and myeloma. Certain forms of leukemia include, by way of non-limiting example, acute lymphocytic leukemia (ALL); acute myeloid leukemia (AML); chronic lymphocytic leukemia (CLL); chronic myelogenous leukemia (CML); Myeloproliferative disorder/neoplasm (MPDS); and myelodysplasia syndrome. Certain forms of lymphoma include, by way of non-limiting example, Hodgkin's lymphoma, both indolent and aggressive non-Hodgkin's lymphoma, Burkitt's lymphoma, and follicular lymphoma (small cell and large cell). Certain forms of myeloma include, by way of non-limiting example, multiple myeloma (MM), giant cell myeloma, heavy-chain myeloma, and light chain or Bence-Jones myeloma. Solid tumors include, e.g., breast tumors, ovarian tumors, lung tumors, pancreatic tumors, prostate tumors, melanoma tumors, colorectal tumors, lung tumors, head and neck tumors, bladder tumors, esophageal tumors, liver tumors, and kidney tumors.

Symptoms associated with cancers and other neoplastic disorders include, for example, inflammation, fever, general malaise, fever, pain, often localized to the inflamed area, loss of appetite, weight loss, edema, headache, fatigue, rash, anemia, muscle weakness, muscle fatigue and abdominal symptoms such as, for example, abdominal pain, diarrhea or constipation.

In specific aspects, provided herein are anti-CD47 antibodies useful in treating, delaying the progression of, impeding, preventing relapse of or alleviating a symptom of a cancer (e.g., MM, NHL, AML, breast cancer, bladder cancer, non-small cell lung cancer/carcinoma, hepatocellular carcinoma (HCC), sarcoma, and head and neck cancer). For example, the CD47 antibodies described herein are useful in treating hematological malignancies and/or tumors, e.g., hematological malignancies and/or tumors. For example, the CD47 antibodies described herein are useful in treating CD47+ tumors. By way of non-limiting example, the CD47 antibodies described herein are useful in treating non-Hodgkin's lymphoma (NHL), acute lymphocytic leukemia (ALL), acute myeloid leukemia (AML), chronic lymphocytic leukemia (CLL), chronic myelogenous leukemia (CML), multiple myeloma (MM), breast cancer, ovarian cancer, head and neck cancer, bladder cancer, melanoma, colorectal cancer, pancreatic cancer, lung cancer, leiomyoma, leiomyosarcoma, glioma, glioblastoma, and so on. Solid tumors include, e.g., breast tumors, ovarian tumors, lung tumors (e.g., NSCLC), pancreatic tumors, prostate tumors, melanoma tumors, colorectal tumors, lung tumors, head and neck tumors, bladder tumors, esophageal tumors, liver tumors (e.g., hepatocellular carcinoma), sarcoma, and kidney tumors.

In a specific embodiment, provided herein is a method of treating cancer (e.g., a hematological disorder/cancer or solid cancer) in a subject comprising administering (e.g., administering concurrently or sequentially) to a subject in need thereof (i) an anti-CD47 antibody described herein or antigen-binding fragment thereof which specifically binds to CD47 such as human CD47, and (ii) another anti-cancer agent. In certain embodiments, the anti-cancer agent is a chermotherapeutic agent (e.g., microtubule disassembly blocker, antimetabolite, topisomerase inhibitor, and DNA crosslinker or damaging agent). In certain embodiments, the anti-cancer agent is a tyrosine kinase inhibitor (e.g., GLEEVEC® (imatinib mesylate) or SUTENT® (SU11248 or Sunitinib)). Other non-limiting examples of tyrosine kinse inhibitors include 706 and AMNI07 (nilotinib). RADOOI, PKC412, gefitinib (IRESSA™), erlotinib (TARCEVA®), sorafenib (NEXAVAR®), pazopanib (VOTRIENT™), axitinib, bosutinib, cediranib (RECENTIN®), SPRYCEL® (dasatinib), lapatinib (TYKERB®), lestaurtinib, neratinib, nilotinib (TASIGNA®), semaxanib, toceranib (PALLADIA™), vandetanib (ZACTIMA™), and vatalanib.

In a specific aspect, provided herein is a method of treating cancer (e.g., a hematological disorder/cancer or solid cancer) in a subject comprising administering (e.g., administering concurrently or sequentially) to a subject in need thereof (i) an anti-CD47 antibody described herein or antigen-binding fragment thereof which specifically binds to CD47 such as human CD47, and (ii) radiation therapy.

In a particular aspect, provided herein is a method of promoting (e.g., inducing or increasing) phagocytosis, e.g., macrophage mediated phagocytic killing of tumor cells, comprising contacting an effective amount of an anti-CD47 antibody described herein which specifically binds to human CD47 with tumor cells. Also provided herein is a method of promoting (e.g., inducing or increasing) phagocytosis, e.g., macrophage mediated phagocytic killing of tumor cells, in a subject in need thereof (e.g., a subject with tumor cells, such as tumor cells expressing CD47), comprising administering to the subject an effective amount of an anti-CD47 antibody described herein which specifically binds to human CD47.

In a particular aspect, provided herein is a method of reducing tumor volume, comprising contacting an effective amount of an anti-CD47 antibody described herein which specifically binds to human CD47 with the tumor. Also provided herein is a method of reducing tumor volume in a subject in need thereof (e.g., a subject with a tumor, such as a CD47 expressing tumor), comprising administering to the subject an effective amount of an anti-CD47 antibody described herein which specifically binds to human CD47.

In a particular aspect, provided herein is a method of inhibiting cancer cell growth or proliferation, comprising contacting an effective amount of an anti-CD47 antibody described herein which specifically binds to human CD47 with cancer cells. Also provided herein is a method of inhibiting cancer cell growth or proliferation in a subject in need thereof (e.g., a subject with cancer cells, such as CD47 expressing cancer cells), comprising administering to the subject an effective amount of an anti-CD47 antibody described herein which specifically binds to human CD47.

5.4.1 Diagnostic Uses

In one aspect, anti-CD47 antibodies described herein and antigen-binding fragments thereof, which specifically bind to an ECD of human CD47 can be used for diagnostic purposes to detect, diagnose, or monitor a condition described herein (e.g., a condition involving CD47 and/or abnormal CD47 signaling and/or abnormal CD47 expression), such as cancer (e.g., colorectal cancer, gastric cancer, lung cancer, or melanoma). In specific embodiments, anti-CD47 antibodies described herein or an antigen-binding fragment thereof for use in diagnostic purposes are labeled. Methods provided herein for diagnostic purposes to detect, diagnose, or monitor a condition described herein can be in vitro methods, in situ methods, or ex vivo methods. Methods provided herein for diagnostic purposes to detect, diagnose, or monitor a condition described herein can be in vivo methods.

In certain embodiments, provided herein are methods for the detection of a condition described herein, such as cancer, comprising: (a) assaying the expression of CD47 in a sample of a subject using one or more antibodies described herein or an antigen-binding fragment thereof; and (b) comparing the level of CD47 expression with a control level, e.g., levels in normal tissue samples (e.g., from a patient not having a condition described herein, or from the same patient before onset of the condition), whereby an increase or decrease in the assayed level of CD47 expression compared to the control level of CD47 expression is indicative of a condition described herein.

In certain embodiments, provided herein are methods for the detection of cancer expressing CD47 (e.g., overexpressing CD47), comprising: (a) assaying the expression of CD47 in a sample of a subject using one or more antibodies described herein or an antigen-binding fragment thereof; and (b) comparing the level of CD47 expression with a control level, e.g., levels in normal samples (e.g., from a patient not having cancer, a patient having cancer that does not overexpress CD47, or from the same patient before onset of cancer). In specific aspects, an increase or decrease in the assayed level of CD47 expression compared to a control level of CD47 expression is indicative of cancer expressing CD47.

In a specific embodiment, provided herein is a method of diagnosing a CD47-expressing cancer in a patient, wherein the method comprises the steps of:
(a) contacting a biological sample from the patient with one or more antibodies described herein or an antigen-binding fragment thereof;
(b) detecting binding of the antibody or antigen-binding fragment to CD47 to determine a CD47 protein level in the biological sample from the patient; and
(c) comparing the CD47 protein level with a standard CD47 protein level.

In a specific embodiment, provided herein is a method of monitoring CD47 protein level during treatment of a CD47-expressing cancer in a patient, wherein the method comprises the steps of:
(a) contacting a biological sample from the patient with one or more antibodies described herein or an antigen-binding fragment thereof;
(b) detecting binding of the antibody or antigen-binding fragment to CD47 to determine a CD47 protein level in the biological sample from the patient; and
(c) comparing the CD47 protein level with a standard CD47 protein level.

Any sample (e.g., bodily fluid or tissue sample) from a subject can be used in diagnostic methods provided herein. Non-limiting examples of samples which can be used in diagnostic methods provided herein include, serum sample, plasma sample, tissue sample, urine sample, tumor sample, and stool sample.

Antibodies described herein can be used to assay CD47 levels in a biological sample using classical immunohistological methods as described herein or as known to those of skill in the art (e.g., see Jalkanen et al., 1985, J. Cell. Biol. 101:976-985; and Jalkanen et al., 1987, J. Cell. Biol. 105: 3087-3096). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($125I$, $121I$), carbon ($14C$), sulfur ($35S$), tritium ($3H$), indium ($121In$), and technetium ($99Tc$); luminescent labels, such as luminol; and fluorescent labels, such as fluorescein and rhodamine, and biotin.

In one embodiment, monitoring of a condition described herein (e.g., a condition involving CD47 and/or abnormal CD47 signaling and/or abnormal CD47 expression), such as cancer, is carried out by repeating the method for diagnosing for a period of time after initial diagnosis.

Presence of the labeled molecule can be detected in the subject using methods known in the art for in vivo scanning. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

6. EXAMPLES

The examples in this section (i.e., Section 6) are offered by way of illustration, and not by way of limitation.

6.1 Example 1: Cell-Free (CF) Antibody Production

Unefficient assembly of the heavy and light chains of anti-CD47 antibody AB6.12 has been observed when co-expressed in the cell-free (CF) system. One approach to improve this process include pre-addition of folded light chain into a heavy chain reaction. In another approach, heavy chain framework sequence modification surprisingly resulted in more efficient assembly and co-expression of the heavy and light chains of anti-CD47 antibodies in the CF system. Characterization of these anti-CD47 antibodies with heavy chain framework sequence modifications are described in more detail below.

Small-Scale Production

Cell-free extracts with over-expression of DsbC (2×DsbC) were thawed to room temperature and incubated with 50 uM iodoacetamide for 30 min. Cell-free reactions were run at 30° C. for up to 10 hours containing 30% (v/v) iodoacetamide-treated extract with 8 mM magnesium glutamate, 10 mM ammonium glutamate, 130 mM potassium glutamate, 35 mM sodium pyruvate, 1.2 mM AMP, 0.86 mM each of GMP, UMP, and CMP, 2 mM amino acids for all 19 amino acids except tyrosine which was added at 0.5 mM, 4 mM sodium oxalate, 1 mM putrescine, 1.5 mM spermidine, 15 mM potassium phosphate, 100 nM T7 RNAP, and 2 mM oxidized (GSSG) glutathione. The concentrations of heavy chain plasmid and light chain plasmid in the reactions were 7.5 ug/mL and 2.5 ug/mL respectively. To label synthesized protein with $^{14}$C, 3.33% (v/v) 1-[U-14C]-leucine (300 mCi/mmole; GE Life Sciences, Piscataway, N.J.) was added to the reaction as well. In this experiment, the following heavy chains (HCs) paired with the same light chain (LC), SEQ ID NO: 13, were expressed.

| sample # | IgG | HC Description | SEQ ID NO: | Antibody name |
|---|---|---|---|---|
| 1 | IgG1 | parental | 2 | IgG1-parental |
| 2 | IgG1 | 5 mutations | 7 | IgG1-5m |
| 3 | IgG1 | 13 mutations | 5 | IgG1-13m |
| 4 | IgG1 Z allotype | 13 mutations Z allotype or 13 + 2 mutations | 6 | IgG1-13mZ |
| 5 | IgG4P | Parental | 3 | IgG4P-parental |
| 6 | IgG4P | 5 mutations | 9 | IgG4P-5m |
| 7 | IgG4P | 13 mutations | 8 | IgG4P-13m |
| 8 | IgG4PE | Parental | 4 | IgG4PE-parental |
| 9 | IgG4PE | 5 mutations | 11 | IgG4PE-5m |
| 10 | IgG4PE | 13 mutations | 10 | IgG4PE-13m |

Exemplary nucleotide sequences encoding the above heavy chain sequences are provided at SEQ ID Nos. 23, 26, 27, 24, 28, 29, 25, 32 and 31, respectively.

For non-reducing SDS-PAGE, 4 uL of sample, 8 uL of deionized water (DI H$_2$O) and 4 uL of 4×LDS buffer (Invitrogen, Carlsbad, Calif.) were mixed before being loaded on gel. For reducing gel, 4 uL of sample, 1 uL of 1 M DTT, 7 uL of DI H$_2$O and 4 uL of 4×LDS buffer (Invitrogen, Carlsbad, Calif.) were mixed and heated in hot blot at 70° C. for 5 minutes. Samples were analyzed by 4~12% Bis-Tris SDS-PAGE gels (Invitrogen, Carlsbad, Calif.) according to the manufacturer's recommendations. Gels were dried and analyzed by autoradiography using a Storm 840 PhospholImager after about 16 hours exposure. The autoradiography is shown in FIG. 1A.

Figure 1B:
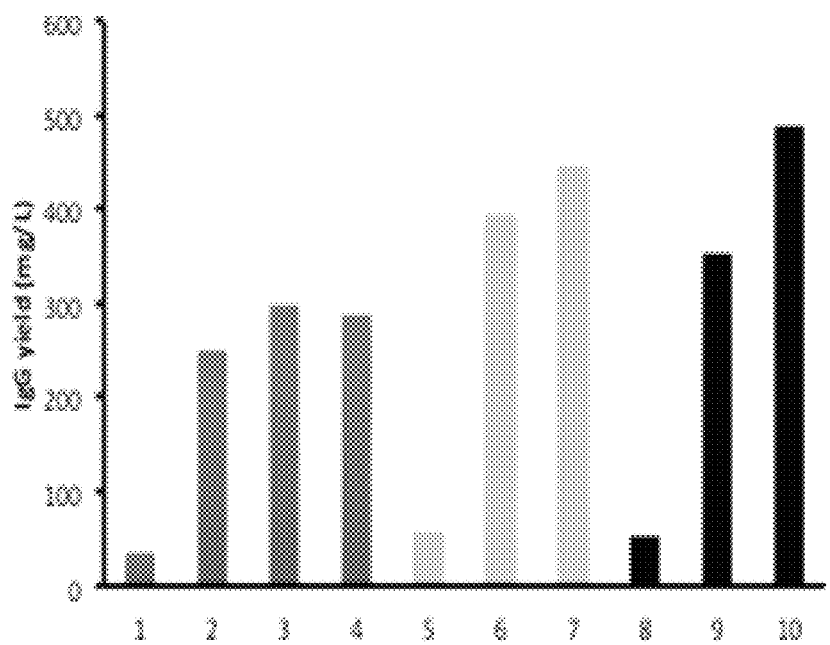
FIG. 1B depicts a graph showing anti-CD47 antibody titers (mg/L) obtained from aCF expression system. Samples 1-10 correspond to CF-expressed anti-CD47 IgG1 (1), IgG1-5m (2), IgG1-13m (3), IgG1-13mZ (4), IgG4P (5), IgG4P-5m (6), IgG4P-13m (7), IgG4PE (8), IgG4PE-5m (9), and IgG4PE-13m (10) antibodies, respectively.

The data indicate that the CF expression titers of IgG1, IgG4P and IgG4PE were each dramatically improved by engineering the 5 mutations and the 13 mutations on their HC sequences. The titers are reported in FIG. 1B.

Scale-Up Production—IgG1 Variants

Scale-up CF production of IgG1 variant antibodies, such as IgG1-5m and IgG1-13mZ, and purification were carried out. The scale-up conditions are described in more details in the Tables (e.g., Tables 3-6) below. Both variants were made with essentially the same method; the most significant difference was in reaction temperature. IgG1-5m was expressed at 25° C. and IgG1-13mZ was run at 30° C. IgG1-13mZ showed similar results at 25° C. and 30° C., but IgG1-5m showed higher titer at 25° C. versus 30° C. The slight differences in reaction timing between the two variants are simply the result of scheduling convenience and not likely to have any significant impact on the process. Different extracts were used for the variants based on extract availability, not on specific extract requirements. Any extract with over-expression of DsbC would be expected to work similarly for these products.

IgG1-13mZ (IgG1, VH1-18 framework, 13+2 mutations) Scale-up Expression:

S30 cell-free extract was treated with 50 uM iodoacetamide (IAM) for 30 minutes at room temperature. After this treatment, the extract was combined with the reagents in Table 3 and transferred to a bioreactor (Dci-BioLafitte Evo Bioreactor, 10 L maximum working volume). The bioreactor controls were configured as listed in Table 4. After 6 hours of reaction, an additional 5 mM (final concentration) oxidized glutathione was added to the reaction. The oxidized glutathione was prepared as a 250 mM stock solution with the pH adjusted to between 7 and 8 before addition to the reactor. The reaction was run for a total of 15 hours before transferring to downstream processing.

TABLE 3

Cell-free reaction components

| Reagent | Final Concentration in CF reaction |
|---|---|
| AMP | 1.2 mM |
| GMP | 0.86 mM |
| UMP | 0.86 mM |
| CMP | 0.86 mM |
| Sodium phosphate | 15 mM |
| 19 amino acids (excluding tyrosine) | 2 mM each |
| Oxalic Acid | 4 mM |
| Putrescine | 1 mM |
| Spermidine | 1.5 mM |
| Ammonium glutamate | 10 mM |
| Potassium glutamate | 130 mM |

TABLE 3-continued

Cell-free reaction components

| Reagent | Final Concentration in CF reaction |
| --- | --- |
| Magnesium glutamate | 8 mM |
| Tyrosine | 1 mM |
| Pyruvate | 35 mM |
| Oxidized glutathione | 2 mM |
| Bacteriophage T7 RNA polymerase | 0.02 g/L |
| Plasmid encoding light chain protein | 2.5 mg/L |
| Plasmid encoding heavy chain protein | 7.5 mg/L |
| Cipro | 1 mg/L |
| Pluronic-R 31R1 | 0.005% (v/v) |
| IAM treated extract from E. coli strain SBDG028 | 30% (v/v) |

TABLE 4

Bioreactor control settings (5 L reaction volume)

| Parameter | Setpoint |
| --- | --- |
| Temperature | 30° C. |
| pH | no control |
| Air flow (sparger) | 1.5 SLPM |
| DO | 100% air saturation |
| Agitation | 200-400 RPM as needed for DO control (primary DO cascade) |
| Oxygen flow (sparger) | 0-2 SLPM as needed for DO control (secondary DO cascade) |

Anti-CD47 Antibody IgG1-5m (IgG1, VH1-18 Framework, 5 Mutations) Scale-Up Expression:

S30 cell-free extract was treated with 50 uM iodoacetamide (IAM) for 30 minutes at room temperature. After this treatment, the extract was combined with the reagents in Table 5 and transferred to a bioreactor (Sartorius Biostat Q Bioreactor, 500 mL maximum working volume). The bioreactor controls were configured as listed in Table 6. After 5.5 hours of reaction, an additional 5 mM (final concentration) oxidized glutathione was added to the reaction. The oxidized glutathione was prepared as a 250 mM stock solution with the pH adjusted to between 7 and 8 before addition to the reactor. The reaction was run for a total of 15.7 hours before transferring to downstream processing.

TABLE 5

Cell-free reaction components

| Reagent | Final Concentration in CF reaction |
| --- | --- |
| AMP | 1.2 mM |
| GMP | 0.86 mM |
| UMP | 0.86 mM |
| CMP | 0.86 mM |
| Sodium phosphate | 15 mM |
| 19 amino acids (excluding tyrosine) | 2 mM each |
| Oxalic Acid | 4 mM |
| Putrescine | 1 mM |
| Spermidine | 1.5 mM |
| Ammonium glutamate | 10 mM |
| Potassium glutamate | 130 mM |
| Magnesium glutamate | 8 mM |
| Tyrosine | 1 mM |
| Pyruvate | 35 mM |
| Oxidized glutathione | 2 mM |
| Bacteriophage T7 RNA polymerase | 0.02 g/L |
| Plasmid encoding light chain protein | 2.5 mg/L |
| Plasmid encoding heavy chain protein | 7.5 mg/L |
| Cipro | 1 mg/L |

TABLE 5-continued

Cell-free reaction components

| Reagent | Final Concentration in CF reaction |
| --- | --- |
| Pluronic-R 31R1 | 0.005% (v/v) |
| IAM treated extract from E. coli strain SBDG031 | 30% (v/v) |

TABLE 6

Bioreactor control settings (0.5 L reaction volume)

| Parameter | Setpoint |
| --- | --- |
| Temperature | 25° C. |
| pH | no control |
| Air flow (sparger) | 0.25 SLPM |
| DO | 80% air saturation |
| Agitation | 200-400 RPM as needed for DO control (primary DO cascade) |
| Oxygen flow (sparger) | 0-1 SLPM as needed for DO control (secondary DO cascade) |

6.2 Example 2: Biacore Analysis of CD47 Binding

Material and Methods:

Immobilization: Anti-human Fc (AHC) surfaces were prepared by amine-coupling monoclonal mouse anti-human Fc IgG (included in the Biacore Human Antibody Capture Kit, GE Life Sciences Cat #BR-1008-39) to a Biacore CM5 sensor chip surface. The running buffer for the immobilization procedure for the immobilization procedure was HBS-EP+ (10 mM HEPES, 150 mM NaCl, 3 mM EDTA, 0.05% v/v P-20 as surfactant). The following was performed in all four flow cells to prepare surfaces amine-coupled anti-human Fc IgG. The CM5 chip surface was activated by injecting a 1:1 (v/v) mixture of 400 mM EDC and 100 mM NHS for 7 minutes at 10 µL/min. Following this treatment, anti-human IgG was diluted to 25 µg/mL in 10 mM sodium acetate buffer pH 5.0, and injected over all the flow cells at 10 µL/min for 7 minutes. Then, Ethanolamine was injected at 10 µL/min for 7 minutes to block all the surfaces. This procedure resulted in immobilization levels of ~10,000-11,000 RU on the sensor chip.

Kinetic Assays: For kinetic assays anti-CD47 antibodies were captured onto the anti-human Fc surfaces (surface preparation described above). For capture of the antibodies with human Fc, the antibodies were diluted to 10 µg/mL in HBS-EP+ running buffer. The antibody variants were immobilized by flowing over flow cell 2, 3 or 4 at a flow rate of 10 uL/min for 12 seconds. The analyte (human CD47 antigen) was diluted into running buffer to prepare a serial dilution series created with a 2-fold dilution factor to give concentrations of 3.125, 6.25, 12.5, 25 and 50 nM. After anti-CD47 antibody capture, the CD47 analyte was injected over the flow cells for 180 seconds (3 minutes) at 50 µL/min, and complex dissociation was monitored for 900 seconds (15 minutes). Buffer blanks were also run, and were used to reference the analyte binding data before fitting. Anti-human Fc surfaces were regenerated with two 30-second injections of 3M $MgCl_2$ at 30 uL/min between each analyte binding cycle.

Kinetic data analysis: Experimental data for a given antibody—antigen interaction were fit using the 1:1 binding model, using global $R_{max}$, global $k_a$ (association), global $k_d$ (dissociation) parameters, and constant RI (bulk refractive index) parameters. Fraction activity (% ligand activity) was determined using the following formula to calculate the relationship between the theoretical $R_{max}$ ($R_{max}$ Theo) and the experimental $R_{max}$ ($R_{max}$ exp). In the formula, stoichiometry represents the instances of interaction between antibody and antigen, for instance, when the antibody is the ligand, each of the antibody arms can interact with antigen, thus the stoichiometry is 2.

$$R\max{}_{theo} = \text{Ligand Level} \times \left(\frac{\text{MW analyte}}{\text{MW ligand}}\right) \times \text{Stochiometry}$$

$$\% \text{ Ligand Activity} = \left(\frac{R\max \text{ exp}}{R\max \text{ theo}}\right) \times 100$$

Results: Biacore analysis showed that all three anti-CD47 antibody variants with 5 mutations (regardless of isotype) have similar off-rate and affinity, with fraction activity (% ligand activity) around 38%. Also, affinity for the antibody variants with 5 mutations agrees well with the parental antibody. The data is summarized in the table (Table 7) below.

TABLE 7

Biacore results summary

| # mutations | Antigen | Ligand | ka (1/Ms) | kd (1/s) | KD (M) | Rmax (RU) | Chi$^2$ (RU$^2$) | % Ligand activity |
|---|---|---|---|---|---|---|---|---|
| PGRTV | CD47 | IgG1 - 5m | 6.36E+05 | 2.60E-03 | 4.09E-09 | 123.4 | 1.83 | 37.4 |
| 5 Mutations | CD47 | IgG4P - 5m | 7.04E+05 | 2.54E-03 | 3.60E-09 | 106.5 | 1.86 | 38.2 |
|  | CD47 | IgG4PE - 5m | 5.94E+05 | 2.54E-03 | 4.27E-09 | 115.4 | 2.5 | 39.2 |
| Control Antibody | CD47 | Anti-CD47 CF Control | 7.32E+05 | 2.31E-03 | 3.16E-09 | 99.68 | 1.36 | 39.4 |

The data for the anti-CD47 antibody variants 13m (with 13 mutations) and 13mZ (with 13 mutations and IgG1 Z allotype) displayed a very fast off-rate, and analysis of the kinetic parameters did not result in a reliable fit based on the 1:1 binding model.

Figure 2A:
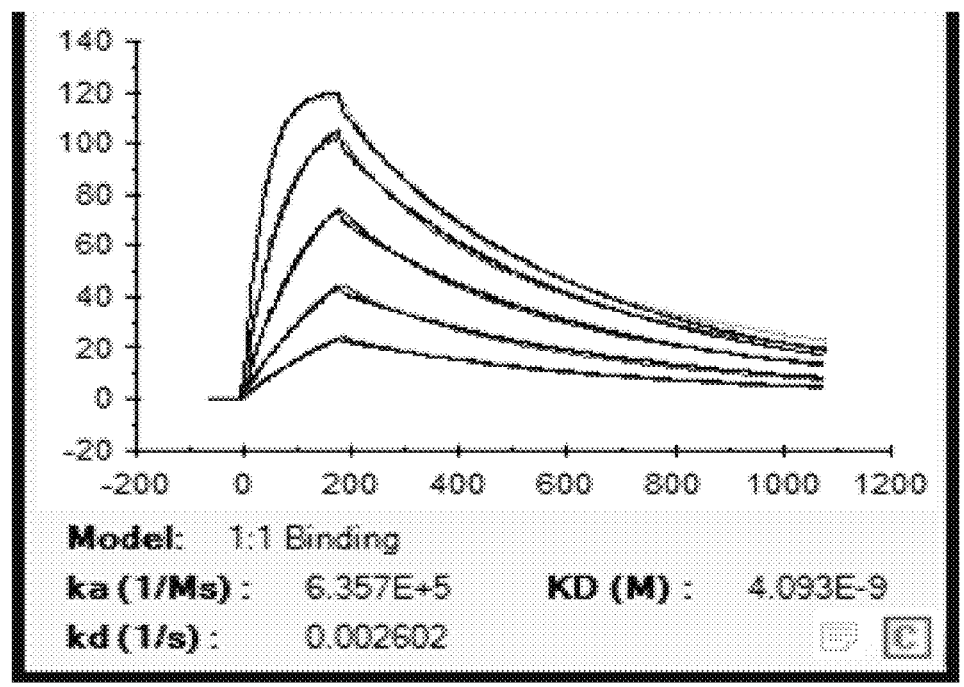
FIGS. 2A-2F depict individual sensorgrams from Biacore analysis of anti-CD47 IgG1-5m (2A), IgG1-13m (2B), IgG1-13mZ (2C), IgG4P-5m (2D), IgG4PE-5m (2E), and control antibody (2F).
Figure 2B:
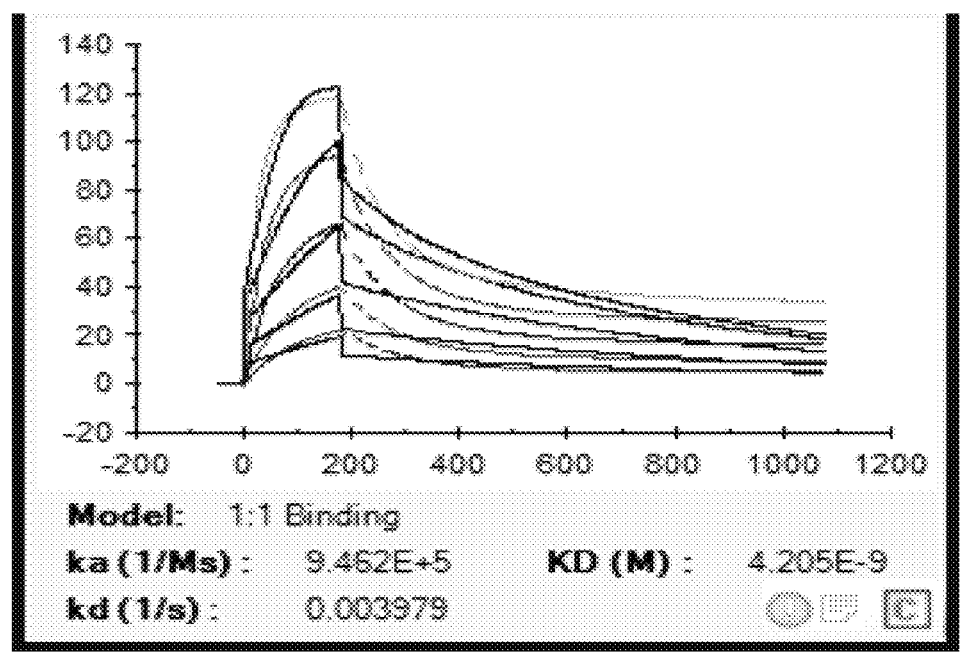
Figure 2C:
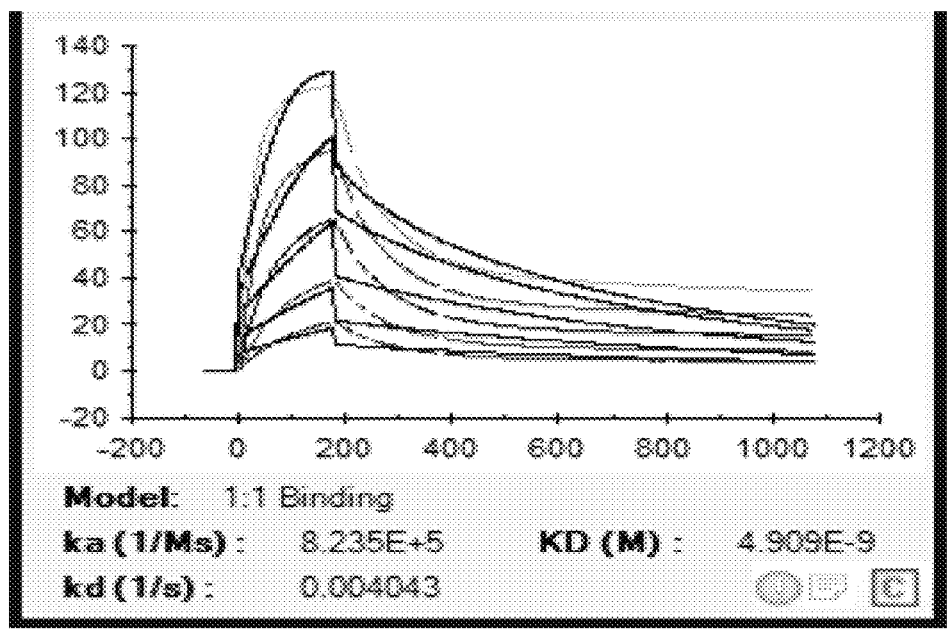
Figure 2D:
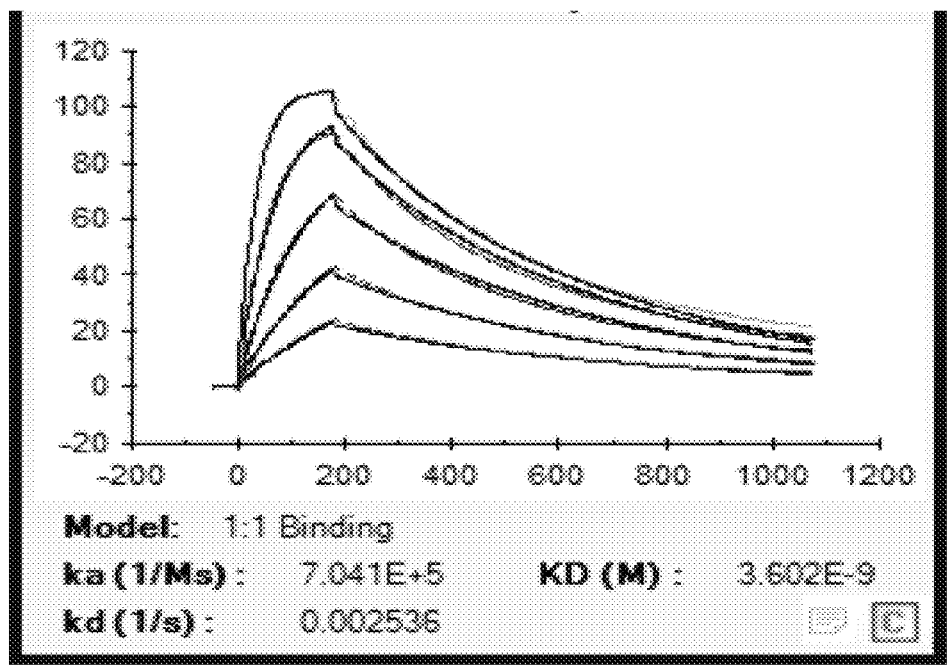
Figure 2E:
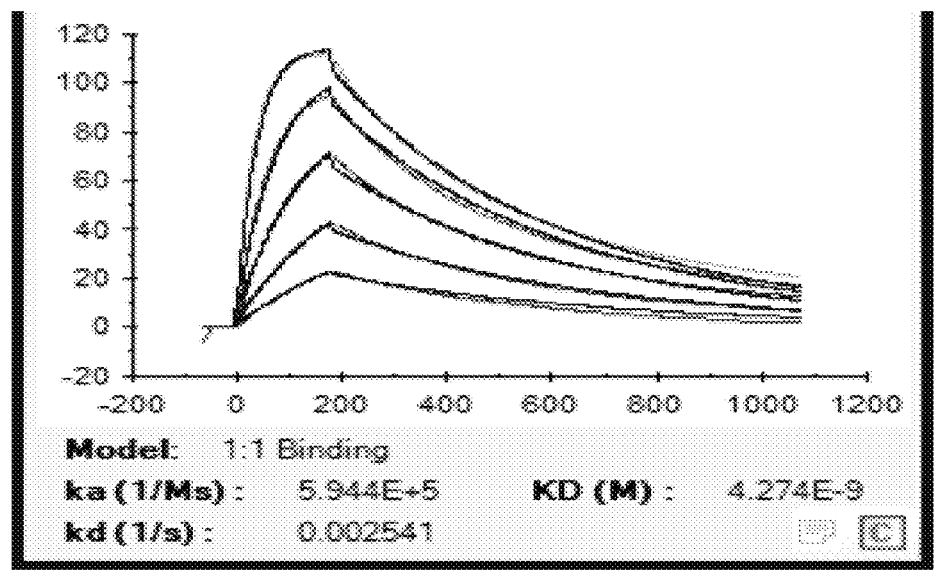
Figure 2F:
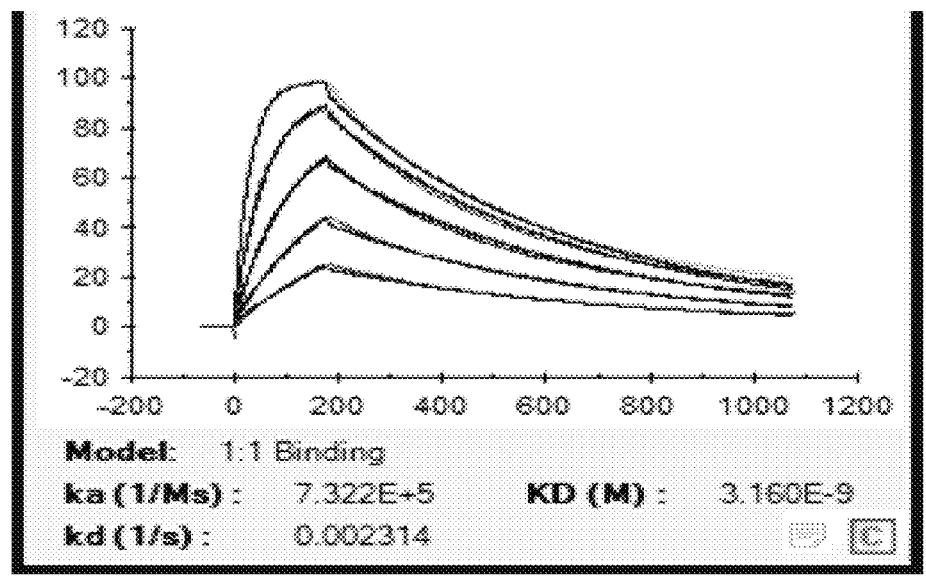

FIGS. 2A-2E depict individual sensorgrams for antibody variants IgG1-5m (FIG. 2A), IgG1-13m (FIG. 2B), IgG1-13mZ (FIG. 2C), IgG4P-5m (FIG. 2D), and IgG4PE-5m (FIG. 2E); and FIG. 2F depicts a sensorgram for anti-CD47 control antibody.

6.3 Example 3: Direct CD47 Cell Binding Assay

To obtain binding curves, sample variants were titrated 1:2 in FACS buffer (PBS 2% FCS) starting from a high concentration of ~66 nM for each sample. 0.1×10$^6$ CCRF-EM cells were plated in a 96 well plate and incubated in 50 µl FACS buffer containing the indicated concentration of sample variants for 1 hour in ice. Cells were then washed with 150 µl FACS buffer and incubated in 50 µl FACS buffer containing the secondary antibody (anti-human-IgG-PE, Jackson ImmunoResearch) diluted 1:100, for 1 hr in ice. Cells were then washed with FACS buffer and fixed in 2% PFA for acquisition with LSR II, DB flow cytometer (BD Biosciences, San Jose, Calif.). Flow Cytometry analysis was performed using FloJo software Version 9.6.4. To obtain titration curves and Kd, Mean Fluorescence Intensity (MFI) values were plotted against concentration (nM). Kd values were calculated using Prism 6, Non linear regression curve fit analysis, One Site Specific Binding with Hill Slope.

Results: All CHO and CF anti-CD47 monoclonal antibodies showed equivalent binding Kd on surface of CCRF-CEM cells, which are human T lymphoblast cells (ATCC® CCL-119™). The calculated Kd (nM) values are presented in the table below (Table 8).

TABLE 8

| anti-CD47 Mabs | Kd (nM) |
|---|---|
| IgG1-parental-CHO | 0.18 |
| IgG1-parental-CF | 0.14 |
| IgG1-13m-CF | 0.15 |
| IgG1-13mZ-CF | 0.21 |
| IgG1-5m-CF | 0.12 |
| IgG4P-parental-CHO | 0.18 |
| IgG4P-5m-CF | 0.14 |
| IgG4PE-parental-CHO | 0.21 |
| IgG4PE-5m-CF | 0.14 |
| B6H12, mu anti-hu CD47 | ~16.0 |

6.4 Example 4: Phagocytosis Assay

Generation of human macrophages: Human peripheral blood mononuclear cells (PBMCs) were isolated from buffy coats (white layer between red blood cells and plasma in a unit of whole blood after it has been spun down in a centrifuge) purchased from the Stanford Blood Center (Palo Alto, Calif., USA). Buffy coats were diluted with PBS 2-fold and layered over 15 ml NycoPrep 1.077 (Axis-Shield, Dundee, Scotland) in 50 ml Leucosep tubes (Greiner Bio One, Monroe, N.C., USA) and centrifuged at 1,000×g for 20 minutes. PBMCs were collected from the interface, washed with 35 ml PBS and centrifuged at 250×g for 5 minutes. Contaminating red blood cells were lysed with 10 ml ACK Lysing Buffer (Lonza, Allendale, N.J., USA) for 2 min and cells were diluted with 40 ml PBS and passed through a 40 um cell strainer (BD Biosciences, San Jose, Calif., USA). Cells were centrifuged at 250×g for 5 mins and resuspended in 30 ml RPMI media containing 10% FBS, 2 mM glutamine and penicillin-streptomycin. PBMCs were counted and cultured at 5×10$^6$ cells/ml in RPMI media overnight. The next day, CD14-positive monocytes were isolated with CD14 microbeads (Miltenyi Biotech, Auburn, Calif., USA) using the AutoMacs Pro and cultured in RPMI media containing 50 ng/ml M-CSF (Peprotech, Rocky Hill, N.J., USA) for 5-7 days to obtain differentiated macrophages. Cells were frozen down in Recovery Cell Culture Freezing Medium (Life Technologies, Grand Island, N.Y., USA).

Measurement of Phagocytosis Activity: Frozen or fresh human macrophages were cultured overnight in 96-well (20,000 cells in 0.1 nil RPMI media supplemented with 50 ng/ml M-CSF). The next day, media was exchanged for 50 µl RPMI media without M-CSF after one wash. CD47-positive CCRF-CEM cells (ATCC, Manassas, Va., USA), passaged under 1.5×10$^6$ cells/ml density, were labeled with 10 µM. CellTrace Oregon Green 488 (Life Technologies, Grand Island, N.Y., USA) for 30 minutes and washed 3× with RPMI media. Labeled CCRF-CEM cells (80,000 cells in 50 µl) and anti-CD47 antibodies in 50 µl RPMI media were added to macrophages. Anti-CD47 antibodies were tested at a final concentration of 4 ng/ml to 10 mg/ml. Plates were briefly centrifuged and incubated at 37° C. for 3 hours.

Macrophages were washed 3× with PBS to remove CCRF-CEM cells and detached with 50 μl Accutase (BD Biosciences, San Jose, Calif., USA) at 37° C. for 10 minutes. Macrophages were collected, washed once with FACS wash buffer (PBS containing 0.2% FBS) and stained with anti-CD14-APC for 15 minute. Cells were washed twice and fixed in 4% paraformaldehyde for 10 minutes. Cells were analyzed by flow cytometry to determine the phagocytic index (% of CD14-positive cells that are Oregon Green labeled). Data was analyzed using GraphPad Prism to obtain dose-response curves and half maximal effective concentration ($EC_{50}$) values using the variable slope (4 parameters) non-linear regression analysis.

Results: Phagocytosis activity was observed for all IgG1 variants (CF and CHO), and IgG4P and IgG4PE from CHO only. $EC_{50}$ values are presented in the table below (Table 9).

TABLE 9

|  | Anti-CD47 variants | $EC_{50}$ (nM) |
|---|---|---|
| IgG1 | IgG1-parental-CHO | 0.3 |
|  | IgG1-parental-CF | 0.5 |
|  | IgG1-5m-CF (R&D) | 0.6 |
|  | IgG1-5m-CF (PD) | 0.3 |
| IgG4P | IgG4P-parental-CHO | 0.5 |
|  | IgG4P-parental-CF | nd |
|  | IgG4P-5m-CF | nd |
| IgG4PE | IgG4PE-parental-CHO | 0.7 |
|  | IgG4PE-parental-CF | nd |
|  | IgG4PE-5m-CF | nd |

6.5 Example 5: Hemagglutination Assay

Published studies suggest that some anti-CD47 antibodies may cause hemagglutination of human red blood cells (RBCs). Therefore, hemagglutination assays were carried out to characterize anti-CD47 antibodies ability to promote agglutination of RBCs.

Human RBCs were sourced from Innovative Research (Cat #IPLA-WB3). Human RBCs (2 mLs) were washed in 10 mLs of 1× dPBS (pH 7.4) and centrifuged for 10 minutes at 500 g (1500 rpm). The supernatant was aspirated, and human RBCs were washed twice, resuspended in 8 mL 1× dPBS for a 20% solution of RBCs. Dilution for the Anti-Human RBC (Rabbit) antibody (Rockland Immunochemicals Inc., Catalog #109-4139, Lot 27233), positive control, was 1:64 with 1:3 serial dilutions (10×). The starting concentration for the samples was 1000 nM with 1:3 serial dilutions (10×). Each antibody titration were pipette (50 μL) to all wells of a U-bottom 96well plate. RBC solution (50 μL of 20% RBC solution) was added to all wells of the plate, and the plate was incubated at 37° C. for at least 1.5 hours to 12 hours (Note: there is no visual difference in the results between 1.5 and overnight). Anti-Human RBC (Rabbit) antibody and MCA911 (Mouse Anti-Human CD47 (clone BRIC 126, Abnova)) served as positive controls. Assays were visualized from the top of the plate. Negative (non-hemagglutination) results appear as intact red dots, while positive (hemagglutination) results appear as a dispersed red mat.

Results: Only positive controls (rabbit anti-human RBC antibody and MCA911 (mouse anti-human CD47 antibody)) showed hemagglutination. No CHO and cell free (CF)-expressed anti-CD47 monoclonal antibodies, including IgG1-parental, IgG4P-parental, IgG4PE-parental, IgG1-13mZ-CF, IgG1-13m-CF, IgG1-5m-CF, IgG4P-5m-CF, IgG4PE-5m-CF, show evidence of hemagglutination.

6.6 Example 6: C1Q Binding ELISA

Method: 96-well high protein binding ELISA plates (MaxSorp Nunc) were coated overnight at 4° C. with sample anti-CD47 antibody variants diluted in 0.05 M Sodium Bicarbonate Buffer (pH 9). Samples were diluted at a high concentration of 133.4 nM (20 μg/ml) and titrated 1:2 in an 11-point dilution curve. Plates were washed three times in PBS, 0.05% Tween 20 and blocked for 1 hour at room temperature with ELISA Diluent (0.1 M $NAPO_4$, 0.1 M NaCl, 0.1% gelatin, 0.05% Tween 20, 0.05% ProClin300). Plates were then washed again three times and incubated for two hours at room temperature with 2 μg/mL human C1q (AbD Serotec 2221-5504, 1 mg/mL stock) diluted in ELISA Diluent. Plates were then washed three times and incubated with sheep anti-human C1q HRP (AbD Serotec 2221-5004P) diluted 1:200 in ELISA Diluent for 1 hour at room temperature to detect bound C1q. Plates were then washed three times, then 100 μL of TMB solution was added. Reaction was quenched by adding 100 μl of 1M Phosphoric Acid and plate was read at 450 nM. Data are plotted using Prism6 as non-linear regression with log (inhibitor) vs. response—Variable slope (four parameters).

Results: IgG1-QN1-CHO shows activity in the C1Q ELISA assay, while IgG4P, IgG4PE, and scFv anti-CD47 monoclonal antibodies do not show activity ("NA") in C1Q ELISA assay. $EC_{50}$ values are presented in the table below (Table 10).

TABLE 10

| Sample | $EC_{50}$ (nM) |
|---|---|
| IgG1-parental-CHO | 3.6 |
| IgG1-parental-CF | NA |
| IgG1-13mZ-CF | NA |
| IgG1-13m-CF | NA |
| IgG1-5m-CF | NA |
| IgG4P-parental-CHO | NA |
| IgG4P-parental-CF | NA |
| IgG4P-5m-CF | NA |
| Anti-CD47 B6H12 scFv | NA |
| IgG4PE-parental-CHO | NA |
| IgG4PE-parental-CF | NA |
| IgG4PE-5m-CF | NA |

6.7 Example 7: Complement-Dependent Cytotoxicity (CDC) Assay

Methods: CD47-expressing cell lines (Raji and/or CCRF) were harvested and re-suspended in CDC buffer (RPMI 1640, L-glutamine (100× stock), and 1% BSA) at 0.3 million cells per mL. Cells were then plated at 10,000 cells per well in a 96 well white tissue culture plate (Falcon) and incubated with sample anti-CD47 antibody variants at a final concentration of 10 μg/mL in CDC buffer at 37° C. for 1 hour. Spin filters (Costar SpinX microcentrifuge tubes) were used to remove residual contaminants. Rabbit (7.5%) or human (30%) serum were then added at a final concentration of 2.5% and 10%, respectively and incubate for 2 hours at 37° C. Sera were diluted in CDC assay buffer. Cell death was then measured using the Cell Tox Glo kit (Promega G292) and following the manufacturer's instructions. Plates were read on Envision luminescent plate reader (Luminescent 96 well full area program) and processed percent CDC activity as (Treated Cells-Spontaneous Cells)/(Total Lysis-Spontaneous Lysis)*100.

Results: CDC activity was observed in Bric 126 antibodies, anti-CD20 IgG1 antibodies and anti-CD20 IgG4 antibodies, while CDC activity was not observed ("NA") in any other antibodies tested. $EC_{50}$ values are presented in the table below (Table 11).

TABLE 11

| Name | EC$_{50}$ (nM) |
| --- | --- |
| CD20 IgG1 | 0.21 |
| BRIC 126 (anti-CD47 antibody) | 0.0014 |
| B6H12 (anti-CD47 antibody) | NA |
| IgG1-parental-CHO | NA |
| IgG4P-parental-CHO | NA |
| IgG4PE-parental-CHO | NA |
| IgG1-parental-CF | NA |
| IgG1-5m-CF | NA |
| IgG1-13m-CF | NA |
| IgG1-13mZ-CF | NA |
| IgG4P-parental-CF | NA |
| IgG4P-5m-CF | NA |
| Control IgG1 Isotype | NA |
| Control IgG4 Isotype | NA |
| IgG4PE-parental-CF | NA |
| IgG4PE-5m-CF | NA |

6.8 Example 8: Antibody-Dependent Cytotoxicity (ADCC) Assay

Methods: PBC were prepared from buffy coats. Buffy coats were diluted with PBS 2-fold and layered over 15 ml NycoPrep 1.077 (Axis-Shield, Dundee, Scotland) in 50 ml Leucosep tubes (Greiner Bio One, Monroe, N.C., USA) and centrifuged at 1,000×g for 20 minutes. PBMCs were collected from the interface and washed with 35 ml PBS and centrifuged at 250×g for 5 minutes. Contaminating red blood cells were lysed with 10 ml ACK Lysing Buffer (Lonza, Allendale, N.J., USA) for 2 minutes and cells were diluted with 40 ml PBS and passed through a 40 µm cell strainer (BD Biosciences, San Jose, Calif., USA). Cells were centrifuged at 250×g for 5 minutes and resuspended in 30 ml RPMI media containing 10% FBS, 2 mM glutamine and penicillin-streptomycin. 10,000 CCRF-CEM or SKBR3 cells were co-cultured with 300,000 PBMCs per each well in a 96 well U bottom polypropylene plate. PBMC were prepared from human buffy coats received from Stanford blood center Three-fold dilutions of the sample variants were added to each well in duplicates, starting from a highest concentration of 22.2 nM and incubated in 37° C. for 3 hours. Cells were then lysed in 50 µL of Glo reagent following manufacturer's instructions. Plates were read on Envision luminescent plate reader (Luminescent 96 well full area program). Percent ADCC activity was calculated as (Treated Cells-Spontaneous Cells)/(Total Lysis-Spontaneous Lysis)*100.

Results: ADCC activity was observed in Trastuzumab (CHO) and IgG1 parental-CHO, both expressed in CHO cells; while ADCC activity was not observed ("NA") in any other anti-CD47 antibody (CHO cell expression or CF expression) tested. EC$_{50}$ values are presented in the table below (Table 12).

TABLE 12

| Antibody Name | IC$_{50}$ (nM) |
| --- | --- |
| IgG1-parental-CHO | 0.06 |
| Trastuzumab (CHO) | 0.001 |
| Trastuzumab (CF) | NA |
| Control IgG1 Isotype | NA |
| IgG4P-parental-CHO | NA |
| IgG4PE-parental-CHO | NA |
| Control IgG4 Isotype | NA |
| IgG1-parental-CF | NA |
| IgG1-5m-CF | NA |
| IgG1-13m-CF | NA |
| IgG1-13mZ-CF | NA |
| IgG4P-parental-CF | NA |
| IgG4P-5m-CF | NA |
| IgG4PE-parental-CF | NA |
| IgG4PE-5m-CF | NA |

6.9 Example 9: Differential Scanning Calorimetry (DSC) (Thermostability) Analysis Method: Differential Scanning calorimetry (DSC) was performed on a GE VP Capillary DSC Instrument. Analysis was performed from 20-100° C. with 60° C./hr heating ramps. Feedback mode was disabled, and a filtering period of 10s was utilized. Pre-scan thermostating was set to 5 minutes. All samples were tested at a concentration of 1 mg/mL in the following buffer: 50 mM L-histidine, 150 mM NaCl, 2% trehalose, pH 6.0

Figure 3A:
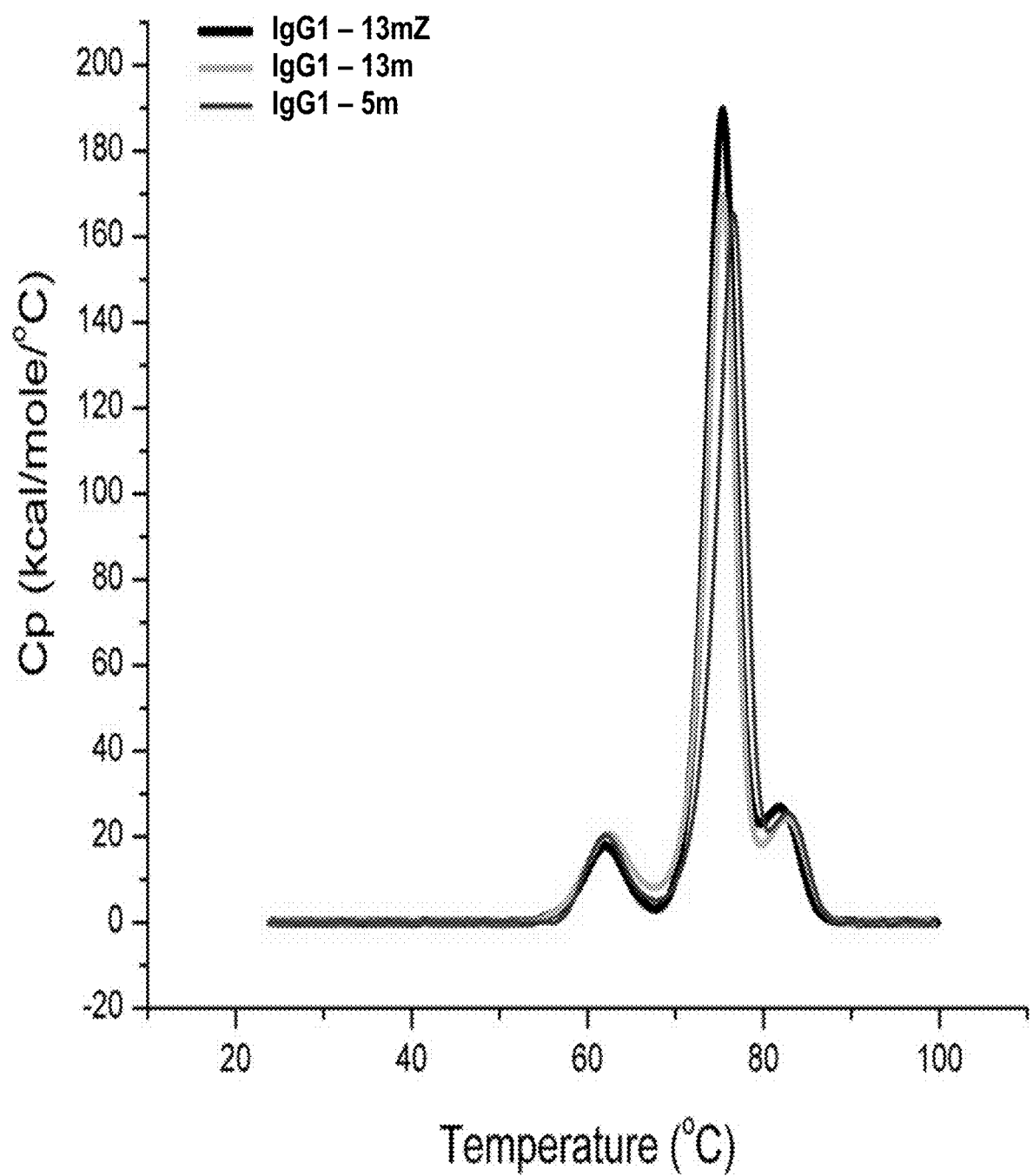
FIGS. 3A-3C depict graphs plotting specific heat capacity (kcal/mol/° C.) versus temperature (° C.) from thermostability analysis using Differential Scanning calorimetry (DSC) for anti-CD47 IgG1-13mZ (3A), IgG1-13m (3B), and IgG1-5m (3C) antibodies.

Results: Three different anti-CD47 IgG$_1$ antibody constructs were analyzed by DSC:
1) IgG1-13mZ
2) IgG1-13m
3) IgG1-5m In particular, the melting transition of the Fab domain (TM2) was of interest, given that the three antibodies differed only in residues located in the Fab domain. As the data shows in FIG. 3A, good cooperative unfolding is observed for the Fab transition for all three constructs, with IgG1-5m exhibiting the highest TM2.

The table below (Table 13) summarizes the transition temperatures of the three different transitions for all three anti-CD47 IgG1 constructs. As can be observed, only minor (<1.0° C.) TM differences can be observed for the CH2 (TM1) and CH3 (TM3) transitions. The TM2 of IgG1-5m, however, does show a 1.5° C. stabilization over the other variants.

TABLE 13

| Variant | TM1 [° C.] | TM2 [° C.] | TM3 [° C.] |
| --- | --- | --- | --- |
| IgG1-13mZ | 62.0 | 75.3 | 81.8 |
| IgG1-13m | 62.5 | 75.3 | 82.5 |
| IgG1-5m | 62.2 | 76.6 | 82.8 |

Figure 3B:
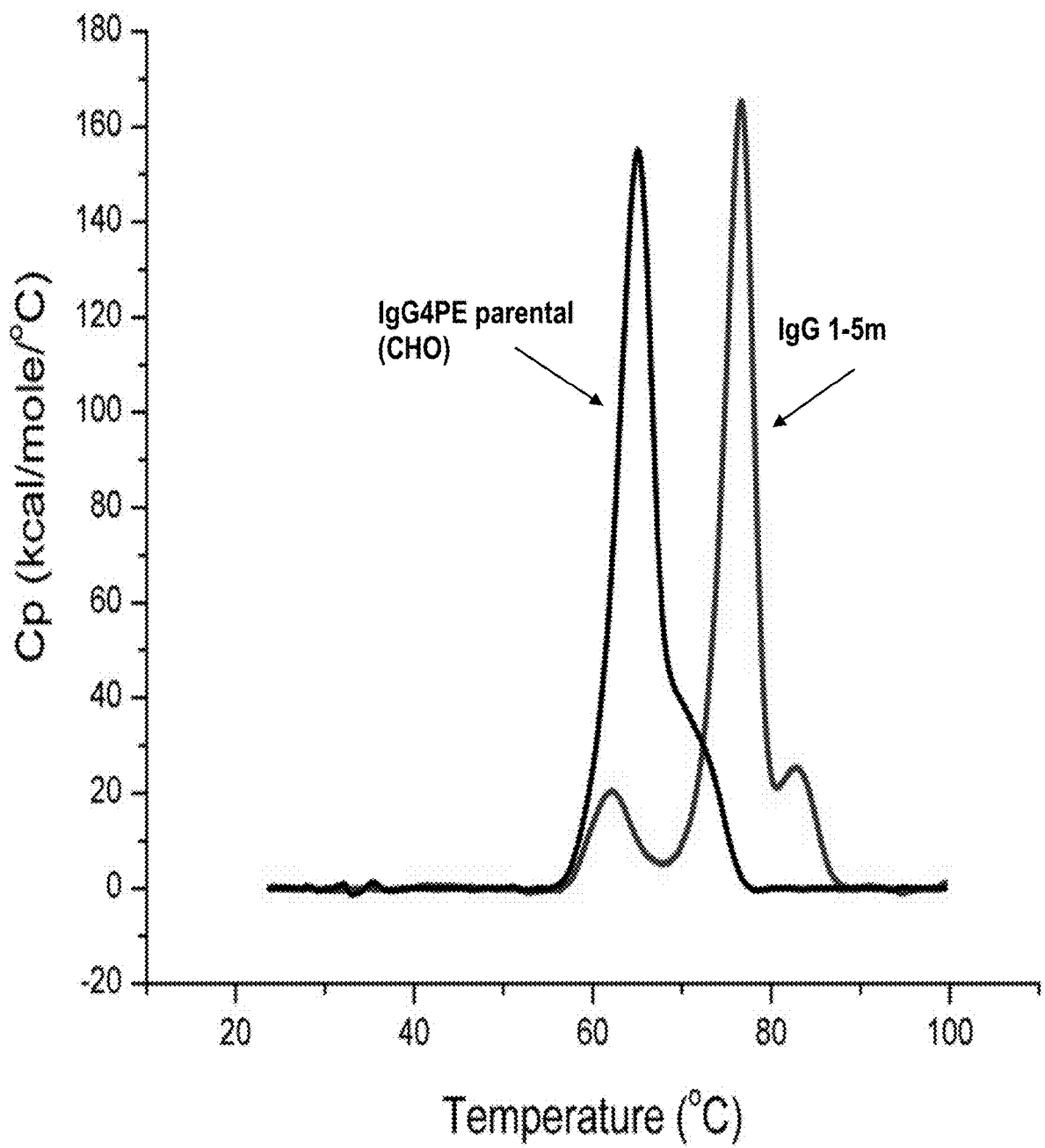

In particular, the IgG1-5m exhibits strikingly improved thermal stability when compared against CHO cell-culture derived IgG4PE (CHO IgG4PE) reference standard (FIG. 3B). As can be observed, all thermal transitions for the CHO IgG4PE material lie below 75° C., while the IgG1-5m is significantly stabilized and denatures at higher temperatures, with the exception of the CH2 domain at 62.2° C.

Figure 3C:
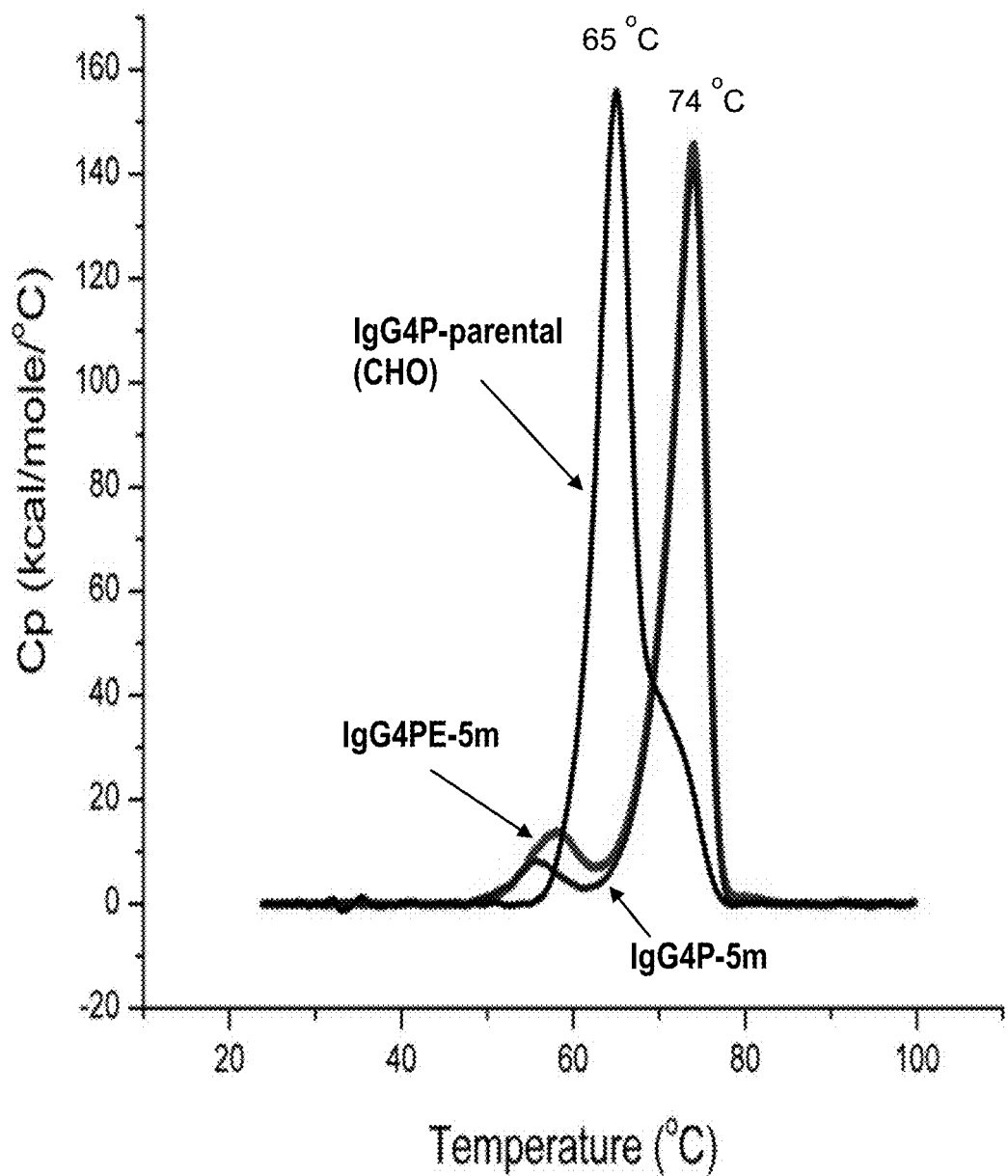
Figure 4:
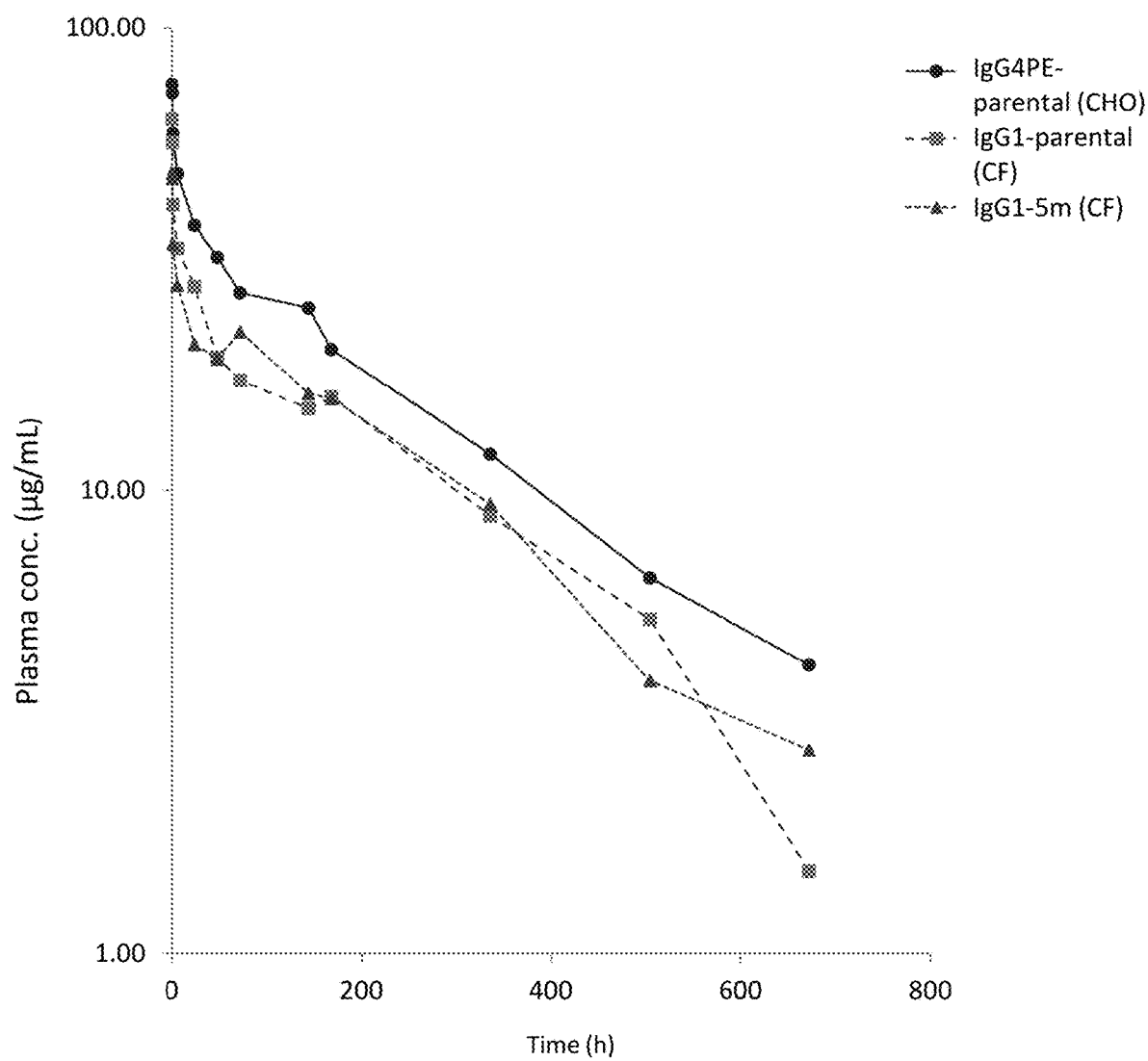
FIG. 4 depicts a graph plotting anti-CD47 antibody plasma concentration (μg/mL) versus time (hours) from pharmacokinetic studies with anti-CD47 IgG4-PE antibody produced with CHO cells and anti-CD47 IgG1 and IgG1-5m antibodies produced by the CF expression system.

To see whether the thermal stabilization observed in the IgG1 context would also translate to the IgG4 scaffold, the following three anti-CD47 IgG4 variants were compared via DSC:
1) IgG4PE-5m
2) IgG4P-5m
3) IgG4PE CHO As can be seen in the thermogram presented in FIG. 3C, Fab region melting in the IgG4P and IgG4PE context is improved by 9° C., by introduction of the 5-mutations, when compared to IgG4PE CHO reference material.

Altogether, these results show that significant thermal stabilization of the Fab domain can be achieved by the introduction of select mutations. As the Fab region remains unchanged between IgG1 and IgG4 scaffolds, the thermal stability gains seem to translate from one scaffold to another, indicating that this should also hold true for other IgG1 isotypes.

6.10 Example 10: The Pharmacokinetics Properties of Anti-CD47 Antibodies

Methods: The anti-CD47 antibodies IgG4-PE CHO, IgG1-CF and IgG1-5m-CF were administered by bolus intravenous injection to mice at dose levels of 3.0, 3.0 and 2.5 mg/kg, respectively. Plasma samples were collected at selected times out to 28 days (672 hours) after dosing, and the concentration of the respective protein determined by immunoassay. The pharmacokinetic parameters were then calculated using a non-compartmental approach with Win-Nonlin 'v' 5.3, Phoenix 64 (Certara, Calif.). The AUC was calculated using the linear trapezoidal rule for the ascending portion of the curve and the log trapezoidal rule for the descending portion. The terminal half-life was determined from a regression of the log of the plasma concentration versus time. The number of points used for the regression was determined by visual inspection of the data using a minimum of three terminal time points. The initial volume of distribution was calculated from the dose/plasma concentration extrapolated to zero time. All other parameters were calculated within WinNonlin using standard methods.

Results: The pharmacokinetics of IgG4-PE CHO, IgG1-CF and IgG1-5m-CF were similar to each other. The clearances are low resulting in relatively long half-lives despite the volumes of distribution also being low, typical for these types of compounds. The initial volume of distribution approximated blood volume whereas the volumes of distribution based on area and at steady-state were approximately half that of extracellular water.

| Conjugate | $C_0$ (µg/mL) | $AUC_{last}$ (µg*h/mL) | $AUC_\infty$ (µg*h/mL) | Terminal $t_{1/2}$ (h) | Cl (mL/h/kg) | Initial V (mL/kg) | $V_z$ (mL/kg) | $V_{ss}$ (mL/kg) |
|---|---|---|---|---|---|---|---|---|
| IgG4-PE CHO | 76.13 | 10063 | 11391 | 218.8 | 0.26 | 39.40627873 | 83.2 | 80 |
| IgG1-CF | 64.9 | 7009 | 7368 | 165 | 0.41 | 46.22496148 | 96.9 | 100.8 |
| IgG1 (5 mut)-CF | 48.8 | 7021 | 7789 | 193.1 | 0.32 | 51.2295082 | 89.4 | 92.4 |

6.11 Example 11: In Vivo Anti-Tumor Activity

The anti-tumor activity of anti-CD47 antibodies produced by the cell-free system were tested in vivo using a xenograft tumor model with the human myeloma cell line RPMI8226.

Methods: NOD/SCID mice were injected subcutaneously with RPMI 8226 cells. Subsequently, mice were treated with vehicle control, hIgG4, or CF anti-CD47 antibodies, such as anti-CD47 IgG1-5m, were administered (qwx3) at a dose of 1 mg/kg, 0.3 mg/kg, or 0.1 mg/kg. Tumor volume were monitored.

Figure 5:
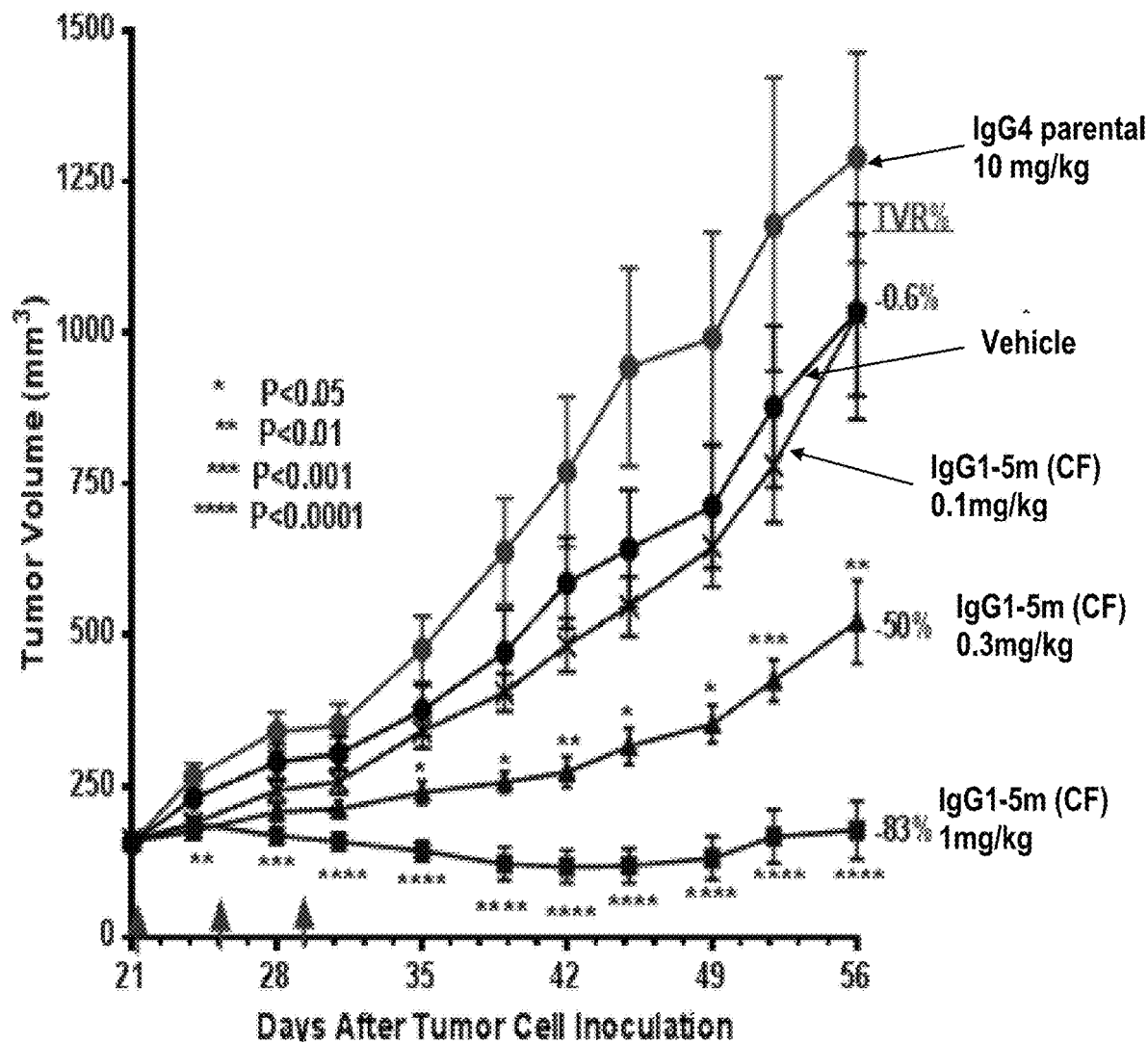
FIG. 5 depicts a graph plotting tumor volume (mm$^3$) versus days after RPMI8226 tumor cell inoculation from in vivo mouse tumor xenograft studies using anti-CD47 IgG1-5m antibodies produced by the CF expression system at doses of 1 mg/kg, 0.3 mg/kg, and 0.1 mg/kg (qwx3).

Results: FIG. 5 depicts a graph of tumor volume versus days after tumor cell inoculation. CF anti-CD47 IgG1-5m antibody achieved tumor volume reduction (TVR) of 83% at a dose of 1 mg/kg and a TVR of 50% at a dose of 0.3 mg/kg. The percentage of tumor free mice at termination is 25% (2/8) for the 1 mg/kg dose of CF anti-CD47 IgG1-5m antibody.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes.

Other embodiments are within the following claims.

What is claimed:

1. A method of treating cancer, or alleviating a symptom of cancer, the method comprising administering a monoclonal anti-CD47 antibody which specifically binds to human CD47 to a subject in need thereof, wherein the anti-CD47 antibody comprises a heavy chain variable region ($V_H$) comprising the amino acid sequence:

(SEQ ID NO: 20)
X1QX2QLVQSGAEVKKX3GX4SVKVSCKASGFNIKDYYLHWVRQAPGQX5

LEWMGWIDPDQGDTEYAQKX6QX7RVTX8TX9DX10SX11STAYMELX12

SLRSX13DTAX14YYCNAAYGSSSYPMDYWGQGTTVTV, wherein $X_1$ is M or there is no amino acid at position $X_1$, $X_2$ is M or V, $X_3$ is P, $X_4$ is S or A, $X_5$ is A or G, $X_6$ is F or L, $X_7$ is G, $X_8$ is I or M, $X_9$ is R or T, $X_{10}$ is R or T, $X_{11}$ is T, $X_{12}$ is R, $X_{13}$ is E or D, and $X_{14}$ is V;

wherein the anti-CD47 antibody comprises a light chain variable region ($V_L$) comprising CDR1, CDR2, and CDR3 comprising amino acid sequences KASQDIHRYLS (SEQ ID NO:17), RANRLVS (SEQ ID NO: 18), and LQYDEFPYT (SEQ ID NO:19), respectively.

2. The method of claim 1, wherein the anti-CD47 antibody has an expression titer or yield when produced using a cell-free system that is higher than an expression titer or yield of a parental anti-CD47 antibody produced using the cell-free system, wherein the parental anti-CD47 antibody comprises a heavy chain variable region comprising an amino acid sequence of SEQ ID NO: 1, 2, 3 or 4.

3. The method of claim 1, wherein the antibody expression titer or yield is higher by at least 1 fold, at least 2 fold, or at least 3 fold compared to said parental antibody.

4. The method of claim 1, which is an IgG1 antibody or an IgG4 antibody.

5. The method of claim 1, which is an IgG4 antibody comprising a S228P amino acid substitution or comprising S228P and L235E amino acid substitutions according to the EU numbering index.

6. The method of claim 2, wherein the parental antibody comprises a light chain variable region comprising the amino acid sequence of SEQ ID NO: 12.

7. The method of claim 2, wherein the antibody comprises 13 or 14 amino acid modifications in the framework region of the heavy chain variable region of the amino acid sequence of SEQ ID NO:1.

8. The method of claim 1, wherein the antibody comprises 10 amino acid modifications in the heavy chain variable region of the amino acid sequence of SEQ ID NO:1.

9. The method of claim 1, wherein the $V_H$ comprises the amino acid sequence of SEQ ID NO:21 or SEQ ID NO:22.

10. The method of claim 1, wherein the antibody comprises a heavy chain comprising the amino acid sequence of SEQ ID NO:5, SEQ ID NO:6, SEQ ID NO:7, SEQ ID NO:8, SEQ ID NO:9, SEQ ID NO:10, or SEQ ID NO:11.

11. The method of claim 1, which comprises a light chain comprising the amino acid sequence of SEQ ID NO:13 or SEQ ID NO:13 without amino acid M at the N-terminus.

12. The method of claim 1, wherein the antibody: (i) does not cause substantial red blood cell depletion, anemia, or both red blood cell depletion and anemia after administration; (ii) inhibits CD47 from interacting with signal-regulatory-protein α (SIRPα); (iii) promotes macrophage-mediated phagocytosis of a CD47-expressing cell; (iv) does not cause a significant level of effector function; or (v) does not cause or promote a significant level of ADCC or CDC.

13. The method of claim 12, wherein the antibody does not cause substantial red blood cell depletion, anemia, or both red blood cell depletion and anemia after administration, and wherein the antibody does not cause substantial platelet depletion, agglutination of cells, or hemagglutination of red blood cells after administration.

14. The method of claim 1, wherein the antibody: (i) when expressed using a cell-free system, exhibits lower binding affinity, or does not bind, to an FcγR than when expressed using CHO cells; or (ii) is aglycosylated or has less glycosylation when expressed using the cell-free system compared to when expressed in CHO cells.

15. The method of claim 14, wherein the antibody when expressed using a cell-free system, exhibits lower binding affinity, or does not bind, to an FcγR than when expressed using CHO cells, and wherein the lower binding affinity is at least 1 log lower or at least 2 log lower.

16. The method of claim 15, wherein the FcγR is FcγRI, FcγRIIA R131, FcγRIIA H131, FcγRIIB, or FcγRIIIA V158.

17. The method of claim 1, wherein the anti-CD47 antibody is a bispecific antibody.

18. The method of claim 1, wherein the anti-CD47 antibody is conjugated to an agent, and wherein the agent is a label or a toxin.

19. The method of claim 1, wherein $X_1$ is M or there is no M at position $X_1$, $X_2$ is M, $X_3$ is P, $X_4$ is S, $X_5$ is G, $X_6$ is F, $X_7$ is G, $X_8$ is I, $X_9$ is R, $X_{10}$ is R, $X_{11}$ is T, $X_{12}$ is R, $X_{13}$ is E, and $X_{14}$ is V.

20. The method of claim 1, wherein the anti-CD47 antibody comprises the $V_H$ within HC SEQ ID NO: 7.

21. The method of claim 1, wherein $X_1$ is M or there is no M at position $X_1$, $X_2$ is M, $X_3$ is P, $X_4$ is S, $X_5$ is A, $X_6$ is F, $X_7$ is G, $X_8$ is I, $X_9$ is R, $X_{10}$ is R, $X_{11}$ is T, $X_{12}$ is R, $X_{13}$ is E, and $X_{14}$ is V.

* * * * *

UNITED STATES PATENT AND TRADEMARK OFFICE
CERTIFICATE OF CORRECTION

| | | |
|---|---|---|
| PATENT NO. | : 11,787,860 B2 | Page 1 of 1 |
| APPLICATION NO. | : 16/949459 | |
| DATED | : October 17, 2023 | |
| INVENTOR(S) | : Aaron Sato et al. | |

It is certified that error appears in the above-identified patent and that said Letters Patent is hereby corrected as shown below:

In the Claims

In Claim 1, Column 121, Lines 62-66, delete:
"(SEQ ID NO: 20)
X1QX2QLVQSGAEVKKX3GX4SVKVSCKASGFNIKDYYLHWVRQAPGQX5LEWMGWIDPDQGDTEYAQKX6QX7RVTX8TX9DX10SX11STAYMELX12SLRSX13DTAX14YYCNAAYGSSSYPMDYWGQGTTVTV,"

And insert:
-- "(SEQ ID NO:20)
$X_1QX_2QLVQSGAEVKKX_3GX_4SVKVSCKASGFNIKDYYLHWVRQAPGQX_5LEWMGWIDPDQGDTEYAQKX_6QX_7RVTX_8TX_9DX_{10}SX_{11}STAYMELX_{12}SLRSX_{13}DTAX_{14}YYCNAAYGSSSYPMDYWGQGTTVTV$ (SEQ ID NO: 20)," --.

Signed and Sealed this
Thirtieth Day of April, 2024

Katherine Kelly Vidal
*Director of the United States Patent and Trademark Office*

SEQUENCE LISTING

```
<160> NUMBER OF SEQ ID NOS: 39

<210> SEQ ID NO 1
<211> LENGTH: 118
<212> TYPE: PRT
<213> ORGANISM: Artificial Sequence
<220> FEATURE:
<223> OTHER INFORMATION: Anti-CD47 antibody AB6.12 heavy chain variable
      region
```

```
<400> SEQUENCE: 1

Gln Met Gln Leu Val Gln Ser Gly Ala Glu Val Lys Lys Thr Gly Ser
 1               5                  10                  15

Ser Val Lys Val Ser Cys Lys Ala Ser Gly Phe Asn Ile Lys Asp Tyr
                20                  25                  30

Tyr Leu His Trp Val Arg Gln Ala Pro Gly Gln Ala Leu Glu Trp Met
             35                  40                  45

Gly Trp Ile Asp Pro Asp Gln Gly Asp Thr Glu Tyr Ala Gln Lys Phe
     50                  55                  60

Gln Asp Arg Val Thr Ile Thr Arg Asp Arg Ser Met Ser Thr Ala Tyr
 65                  70                  75                  80

Met Glu Leu Ser Ser Leu Arg Ser Glu Asp Thr Ala Met Tyr Tyr Cys
                 85                  90                  95

Asn Ala Ala Tyr Gly Ser Ser Tyr Pro Met Asp Tyr Trp Gly Gln
             100                 105                 110

Gly Thr Thr Val Thr Val
             115

<210> SEQ ID NO 2
<211> LENGTH: 451
<212> TYPE: PRT
<213> ORGANISM: Artificial Sequence
<220> FEATURE:
<223> OTHER INFORMATION: Anti-CD47 antibody IgG1 heavy chain

<400> SEQUENCE: 2

Met Gln Met Gln Leu Val Gln Ser Gly Ala Glu Val Lys Lys Thr Gly
 1               5                  10                  15

Ser Ser Val Lys Val Ser Cys Lys Ala Ser Gly Phe Asn Ile Lys Asp
                20                  25                  30

Tyr Tyr Leu His Trp Val Arg Gln Ala Pro Gly Gln Ala Leu Glu Trp
             35                  40                  45

Met Gly Trp Ile Asp Pro Asp Gln Gly Asp Thr Glu Tyr Ala Gln Lys
     50                  55                  60

Phe Gln Asp Arg Val Thr Ile Thr Arg Asp Arg Ser Met Ser Thr Ala
 65                  70                  75                  80

Tyr Met Glu Leu Ser Ser Leu Arg Ser Glu Asp Thr Ala Met Tyr Tyr
                 85                  90                  95

Cys Asn Ala Ala Tyr Gly Ser Ser Tyr Pro Met Asp Tyr Trp Gly
             100                 105                 110

Gln Gly Thr Thr Val Thr Val Ser Ser Ala Ser Thr Lys Gly Pro Ser
         115                 120                 125

Val Phe Pro Leu Ala Pro Ser Ser Lys Ser Thr Ser Gly Gly Thr Ala
     130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Thr Val
            180                 185                 190

Pro Ser Ser Ser Leu Gly Thr Gln Thr Tyr Ile Cys Asn Val Asn His
         195                 200                 205

Lys Pro Ser Asn Thr Lys Val Asp Lys Lys Val Glu Pro Lys Ser Cys
     210                 215                 220
```

```
Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Asp Glu Leu Thr Lys Asn Gln Val Ser
    355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
    435                 440                 445

Pro Gly Lys
    450

<210> SEQ ID NO 3
<211> LENGTH: 448
<212> TYPE: PRT
<213> ORGANISM: Artificial Sequence
<220> FEATURE:
<223> OTHER INFORMATION: Anti-CD47 antibody IgG4P heavy chain

<400> SEQUENCE: 3

Met Gln Met Gln Leu Val Gln Ser Gly Ala Glu Val Lys Lys Thr Gly
1               5                   10                  15

Ser Ser Val Lys Val Ser Cys Lys Ala Ser Gly Phe Asn Ile Lys Asp
            20                  25                  30

Tyr Tyr Leu His Trp Val Arg Gln Ala Pro Gly Gln Ala Leu Glu Trp
        35                  40                  45

Met Gly Trp Ile Asp Pro Asp Gln Gly Asp Thr Glu Tyr Ala Gln Lys
    50                  55                  60

Phe Gln Asp Arg Val Thr Ile Thr Arg Asp Arg Ser Met Ser Thr Ala
65                  70                  75                  80

Tyr Met Glu Leu Ser Ser Leu Arg Ser Glu Asp Thr Ala Met Tyr Tyr
            85                  90                  95

Cys Asn Ala Ala Tyr Gly Ser Ser Ser Tyr Pro Met Asp Tyr Trp Gly
        100                 105                 110

Gln Gly Thr Thr Val Thr Val Ser Ser Ala Ser Thr Lys Gly Pro Ser
    115                 120                 125
```

```
Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 4
<211> LENGTH: 448
<212> TYPE: PRT
<213> ORGANISM: Artificial Sequence
<220> FEATURE:
<223> OTHER INFORMATION: Anti-CD47 antibody IgG4PE heavy chain
      (comprising S228P and L235E substitutions)

<400> SEQUENCE: 4

Met Gln Met Gln Leu Val Gln Ser Gly Ala Glu Val Lys Lys Thr Gly
1               5                   10                  15

Ser Ser Val Lys Val Ser Cys Lys Ala Ser Gly Phe Asn Ile Lys Asp
            20                  25                  30

Tyr Tyr Leu His Trp Val Arg Gln Ala Pro Gly Gln Ala Leu Glu Trp
        35                  40                  45
```

```
Met Gly Trp Ile Asp Pro Asp Gln Gly Asp Thr Glu Tyr Ala Gln Lys
         50                  55                  60

Phe Gln Asp Arg Val Thr Ile Thr Arg Asp Arg Ser Met Ser Thr Ala
 65                  70                  75                  80

Tyr Met Glu Leu Ser Ser Leu Arg Ser Glu Asp Thr Ala Met Tyr Tyr
                     85                  90                  95

Cys Asn Ala Ala Tyr Gly Ser Ser Tyr Pro Met Asp Tyr Trp Gly
                100                 105                 110

Gln Gly Thr Thr Val Thr Val Ser Ser Ala Ser Thr Lys Gly Pro Ser
             115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Lys Thr Tyr Thr Cys Asn Val Asp His
             195                 200                 205

Lys Pro Ser Asn Thr Lys Val Asp Lys Arg Val Glu Ser Lys Tyr Gly
210                 215                 220

Pro Pro Cys Pro Pro Cys Pro Ala Pro Glu Phe Glu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
                260                 265                 270

Glu Val Gln Phe Asn Trp Tyr Val Asp Gly Val Glu Val His Asn Ala
             275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
             340                 345                 350

Pro Pro Ser Gln Glu Glu Met Thr Lys Asn Gln Val Ser Leu Thr Cys
             355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
             420                 425                 430

Leu His Asn His Tyr Thr Gln Lys Ser Leu Ser Leu Ser Leu Gly Lys
             435                 440                 445
```

<210> SEQ ID NO 5
<211> LENGTH: 451
<212> TYPE: PRT
<213> ORGANISM: Artificial Sequence
<220> FEATURE:
<223> OTHER INFORMATION: Anti-CD47 antibody IgG1-13m heavy chain

<400> SEQUENCE: 5

```
Met Gln Val Gln Leu Val Gln Ser Gly Ala Glu Val Lys Lys Pro Gly
1               5                   10                  15

Ala Ser Val Lys Val Ser Cys Lys Ala Ser Gly Phe Asn Ile Lys Asp
            20                  25                  30

Tyr Tyr Leu His Trp Val Arg Gln Ala Pro Gly Gln Gly Leu Glu Trp
        35                  40                  45

Met Gly Trp Ile Asp Pro Asp Gln Gly Asp Thr Glu Tyr Ala Gln Lys
    50                  55                  60

Leu Gln Gly Arg Val Thr Met Thr Thr Asp Thr Ser Thr Ser Thr Ala
65                  70                  75                  80

Tyr Met Glu Leu Arg Ser Leu Arg Ser Asp Asp Thr Ala Val Tyr Tyr
                85                  90                  95

Cys Asn Ala Ala Tyr Gly Ser Ser Ser Tyr Pro Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365
```

```
Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 6
<211> LENGTH: 451
<212> TYPE: PRT
<213> ORGANISM: Artificial Sequence
<220> FEATURE:
<223> OTHER INFORMATION: Anti-CD47 antibody IgG1-13mZ heavy chain

<400> SEQUENCE: 6

Met Gln Val Gln Leu Val Gln Ser Gly Ala Glu Val Lys Lys Pro Gly
1               5                   10                  15

Ala Ser Val Lys Val Ser Cys Lys Ala Ser Gly Phe Asn Ile Lys Asp
            20                  25                  30

Tyr Tyr Leu His Trp Val Arg Gln Ala Pro Gly Gln Gly Leu Glu Trp
        35                  40                  45

Met Gly Trp Ile Asp Pro Asp Gln Gly Asp Thr Glu Tyr Ala Gln Lys
    50                  55                  60

Leu Gln Gly Arg Val Thr Met Thr Thr Asp Thr Ser Thr Ser Thr Ala
65                  70                  75                  80

Tyr Met Glu Leu Arg Ser Leu Arg Ser Asp Asp Thr Ala Val Tyr Tyr
                85                  90                  95

Cys Asn Ala Ala Tyr Gly Ser Ser Ser Tyr Pro Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270
```

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 7
<211> LENGTH: 451
<212> TYPE: PRT
<213> ORGANISM: Artificial Sequence
<220> FEATURE:
<223> OTHER INFORMATION: Anti-CD47 antibody IgG1-5m heavy chain

<400> SEQUENCE: 7

Met Gln Met Gln Leu Val Gln Ser Gly Ala Glu Val Lys Lys Pro Gly
1               5                   10                  15

Ser Ser Val Lys Val Ser Cys Lys Ala Ser Gly Phe Asn Ile Lys Asp
            20                  25                  30

Tyr Tyr Leu His Trp Val Arg Gln Ala Pro Gly Gln Ala Leu Glu Trp
        35                  40                  45

Met Gly Trp Ile Asp Pro Asp Gln Gly Asp Thr Glu Tyr Ala Gln Lys
    50                  55                  60

Phe Gln Gly Arg Val Thr Ile Thr Arg Asp Arg Ser Thr Ser Thr Ala
65                  70                  75                  80

Tyr Met Glu Leu Arg Ser Leu Arg Ser Glu Asp Thr Ala Val Tyr Tyr
                85                  90                  95

Cys Asn Ala Ala Tyr Gly Ser Ser Ser Tyr Pro Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

```
Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 8
<211> LENGTH: 448
<212> TYPE: PRT
<213> ORGANISM: Artificial Sequence
<220> FEATURE:
<223> OTHER INFORMATION: Anti-CD47 antibody IgG4P-13m heavy chain

<400> SEQUENCE: 8

Met Gln Val Gln Leu Val Gln Ser Gly Ala Glu Val Lys Lys Pro Gly
1               5                   10                  15

Ala Ser Val Lys Val Ser Cys Lys Ala Ser Gly Phe Asn Ile Lys Asp
            20                  25                  30

Tyr Tyr Leu His Trp Val Arg Gln Ala Pro Gly Gln Gly Leu Glu Trp
        35                  40                  45

Met Gly Trp Ile Asp Pro Asp Gln Gly Asp Thr Glu Tyr Ala Gln Lys
    50                  55                  60

Leu Gln Gly Arg Val Thr Met Thr Thr Asp Thr Ser Thr Ser Thr Ala
65                  70                  75                  80
```

```
Tyr Met Glu Leu Arg Ser Leu Arg Ser Asp Thr Ala Val Tyr Tyr
             85                  90                  95

Cys Asn Ala Ala Tyr Gly Ser Ser Tyr Pro Met Asp Tyr Trp Gly
            100                 105                 110

Gln Gly Thr Thr Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
130             135                 140

Ala Leu Gly Cys Leu Val Lys Asp Tyr Phe Pro Glu Pro Val Thr Val
145             150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
            210                 215                 220

Pro Pro Cys Pro Pro Cys Pro Ala Pro Glu Phe Leu Gly Gly Pro Ser
225             230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
            290                 295                 300

Ser Val Leu Thr Val Leu His Gln Asp Trp Leu Asn Gly Lys Glu Tyr
305             310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385             390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

<210> SEQ ID NO 9
<211> LENGTH: 448
<212> TYPE: PRT
<213> ORGANISM: Artificial Sequence
<220> FEATURE:
<223> OTHER INFORMATION: Anti-CD47 antibody IgG4P-5m heavy chain
```

<400> SEQUENCE: 9

```
Met Gln Met Gln Leu Val Gln Ser Gly Ala Glu Val Lys Lys Pro Gly
1               5                   10                  15

Ser Ser Val Lys Val Ser Cys Lys Ala Ser Gly Phe Asn Ile Lys Asp
            20                  25                  30

Tyr Tyr Leu His Trp Val Arg Gln Ala Pro Gly Gln Ala Leu Glu Trp
        35                  40                  45

Met Gly Trp Ile Asp Pro Asp Gln Gly Asp Thr Glu Tyr Ala Gln Lys
    50                  55                  60

Phe Gln Gly Arg Val Thr Ile Thr Arg Asp Arg Ser Thr Ser Thr Ala
65                  70                  75                  80

Tyr Met Glu Leu Arg Ser Leu Arg Ser Glu Asp Thr Ala Val Tyr Tyr
                85                  90                  95

Cys Asn Ala Ala Tyr Gly Ser Ser Ser Tyr Pro Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415
```

Arg Trp Gln Glu Gly Asn Val Phe Ser Cys Ser Val Met His Glu Ala
                420                 425                 430

Leu His Asn His Tyr Thr Gln Lys Ser Leu Ser Leu Ser Leu Gly Lys
            435                 440                 445

<210> SEQ ID NO 10
<211> LENGTH: 448
<212> TYPE: PRT
<213> ORGANISM: Artificial Sequence
<220> FEATURE:
<223> OTHER INFORMATION: Anti-CD47 antibody IgG4PE-13m heavy chain

<400> SEQUENCE: 10

Met Gln Val Gln Leu Val Gln Ser Gly Ala Glu Val Lys Lys Pro Gly
1               5                   10                  15

Ala Ser Val Lys Val Ser Cys Lys Ala Ser Gly Phe Asn Ile Lys Asp
            20                  25                  30

Tyr Tyr Leu His Trp Val Arg Gln Ala Pro Gly Gln Gly Leu Glu Trp
        35                  40                  45

Met Gly Trp Ile Asp Pro Asp Gln Gly Asp Thr Glu Tyr Ala Gln Lys
    50                  55                  60

Leu Gln Gly Arg Val Thr Met Thr Thr Asp Thr Ser Thr Ser Thr Ala
65                  70                  75                  80

Tyr Met Glu Leu Arg Ser Leu Arg Ser Asp Asp Thr Ala Val Tyr Tyr
                85                  90                  95

Cys Asn Ala Ala Tyr Gly Ser Ser Tyr Pro Met Asp Tyr Trp Gly
            100                 105                 110

Gln Gly Thr Thr Val Thr Val Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Thr Val
        180                 185                 190

Pro Ser Ser Ser Leu Gly Thr Lys Thr Tyr Thr Cys Asn Val Asp His
    195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Glu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

```
Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

<210> SEQ ID NO 11
<211> LENGTH: 448
<212> TYPE: PRT
<213> ORGANISM: Artificial Sequence
<220> FEATURE:
<223> OTHER INFORMATION: Anti-CD47 antibody IgG4PE-5m heavy chain

<400> SEQUENCE: 11

Met Gln Met Gln Leu Val Gln Ser Gly Ala Glu Val Lys Lys Pro Gly
1               5                   10                  15

Ser Ser Val Lys Val Ser Cys Lys Ala Ser Gly Phe Asn Ile Lys Asp
            20                  25                  30

Tyr Tyr Leu His Trp Val Arg Gln Ala Pro Gly Gln Ala Leu Glu Trp
        35                  40                  45

Met Gly Trp Ile Asp Pro Asp Gln Gly Asp Thr Glu Tyr Ala Gln Lys
    50                  55                  60

Phe Gln Gly Arg Val Thr Ile Thr Arg Asp Arg Ser Thr Ser Thr Ala
65                  70                  75                  80

Tyr Met Glu Leu Arg Ser Leu Arg Ser Glu Asp Thr Ala Val Tyr Tyr
                85                  90                  95

Cys Asn Ala Ala Tyr Gly Ser Ser Tyr Pro Met Asp Tyr Trp Gly
            100                 105                 110

Gln Gly Thr Thr Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Glu Gly Gly Pro Ser
225                 230                 235                 240

Val Phe Leu Phe Pro Pro Lys Pro Lys Asp Thr Leu Met Ile Ser Arg
                245                 250                 255
```

Thr Pro Glu Val Thr Cys Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 12
<211> LENGTH: 107
<212> TYPE: PRT
<213> ORGANISM: Artificial Sequence
<220> FEATURE:
<223> OTHER INFORMATION: Anti-CD47 antibody AB6.12 light chain variable
      region

<400> SEQUENCE: 12

Asn Ile Gln Met Thr Gln Ser Pro Ser Ala Met Ser Ala Ser Val Gly
1               5                   10                  15

Asp Arg Val Thr Ile Thr Cys Lys Ala Ser Gln Asp Ile His Arg Tyr
            20                  25                  30

Leu Ser Trp Phe Gln Gln Lys Pro Gly Lys Val Pro Lys His Leu Ile
        35                  40                  45

Tyr Arg Ala Asn Arg Leu Val Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gly Gly Thr Lys Val Glu Ile Lys
            100                 105

<210> SEQ ID NO 13
<211> LENGTH: 215
<212> TYPE: PRT
<213> ORGANISM: Artificial Sequence
<220> FEATURE:
<223> OTHER INFORMATION: Light chain (Ig Kappa)

-continued

<400> SEQUENCE: 13

Met Asn Ile Gln Met Thr Gln Ser Pro Ser Ala Met Ser Ala Ser Val
1               5                   10                  15

Gly Asp Arg Val Thr Ile Thr Cys Lys Ala Ser Gln Asp Ile His Arg
                20                  25                  30

Tyr Leu Ser Trp Phe Gln Gln Lys Pro Gly Lys Val Pro Lys His Leu
            35                  40                  45

Ile Tyr Arg Ala Asn Arg Leu Val Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gln Tyr Asp Glu Phe Pro
                85                  90                  95

Tyr Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 14
<211> LENGTH: 10
<212> TYPE: PRT
<213> ORGANISM: Artificial Sequence
<220> FEATURE:
<223> OTHER INFORMATION: VH CDR1

<400> SEQUENCE: 14

Gly Phe Asn Ile Lys Asp Tyr Tyr Leu His
1               5                   10

<210> SEQ ID NO 15
<211> LENGTH: 10
<212> TYPE: PRT
<213> ORGANISM: Artificial Sequence
<220> FEATURE:
<223> OTHER INFORMATION: VH CDR2

<400> SEQUENCE: 15

Trp Ile Asp Pro Asp Gln Gly Asp Thr Glu
1               5                   10

<210> SEQ ID NO 16
<211> LENGTH: 13
<212> TYPE: PRT
<213> ORGANISM: Artificial Sequence
<220> FEATURE:
<223> OTHER INFORMATION: VH CDR3

```
<400> SEQUENCE: 16

Asn Ala Ala Tyr Gly Ser Ser Ser Tyr Pro Met Asp Tyr
1               5                   10

<210> SEQ ID NO 17
<211> LENGTH: 11
<212> TYPE: PRT
<213> ORGANISM: Artificial Sequence
<220> FEATURE:
<223> OTHER INFORMATION: VL CDR1

<400> SEQUENCE: 17

Lys Ala Ser Gln Asp Ile His Arg Tyr Leu Ser
1               5                   10

<210> SEQ ID NO 18
<211> LENGTH: 7
<212> TYPE: PRT
<213> ORGANISM: Artificial Sequence
<220> FEATURE:
<223> OTHER INFORMATION: VL CDR2

<400> SEQUENCE: 18

Arg Ala Asn Arg Leu Val Ser
1               5

<210> SEQ ID NO 19
<211> LENGTH: 9
<212> TYPE: PRT
<213> ORGANISM: Artificial Sequence
<220> FEATURE:
<223> OTHER INFORMATION: VL CDR3

<400> SEQUENCE: 19

Leu Gln Tyr Asp Glu Phe Pro Tyr Thr
1               5

<210> SEQ ID NO 20
<211> LENGTH: 119
<212> TYPE: PRT
<213> ORGANISM: Artificial Sequence
<220> FEATURE:
<223> OTHER INFORMATION: consensus sequence for anti-CD47 antibody
      heavy chain variable region
<220> FEATURE:
<221> NAME/KEY: misc_feature
<222> LOCATION: (1)..(1)
<223> OTHER INFORMATION: Xaa = any amino acid or absent
<220> FEATURE:
<221> NAME/KEY: misc_feature
<222> LOCATION: (3)..(3)
<223> OTHER INFORMATION: Xaa = any amino acid
<220> FEATURE:
<221> NAME/KEY: misc_feature
<222> LOCATION: (15)..(15)
<223> OTHER INFORMATION: Xaa = any amino acid
<220> FEATURE:
<221> NAME/KEY: misc_feature
<222> LOCATION: (17)..(17)
<223> OTHER INFORMATION: Xaa = any amino acid
<220> FEATURE:
<221> NAME/KEY: misc_feature
<222> LOCATION: (45)..(45)
<223> OTHER INFORMATION: Xaa = any amino acid
<220> FEATURE:
<221> NAME/KEY: misc_feature
<222> LOCATION: (65)..(65)
<223> OTHER INFORMATION: Xaa = any amino acid
```

```
<220> FEATURE:
<221> NAME/KEY: misc_feature
<222> LOCATION: (67)..(67)
<223> OTHER INFORMATION: Xaa = any amino acid
<220> FEATURE:
<221> NAME/KEY: misc_feature
<222> LOCATION: (71)..(71)
<223> OTHER INFORMATION: Xaa = any amino acid
<220> FEATURE:
<221> NAME/KEY: misc_feature
<222> LOCATION: (73)..(73)
<223> OTHER INFORMATION: Xaa = any amino acid
<220> FEATURE:
<221> NAME/KEY: misc_feature
<222> LOCATION: (75)..(75)
<223> OTHER INFORMATION: Xaa = Arg or Thr
<220> FEATURE:
<221> NAME/KEY: misc_feature
<222> LOCATION: (77)..(77)
<223> OTHER INFORMATION: Xaa = any amino acid
<220> FEATURE:
<221> NAME/KEY: misc_feature
<222> LOCATION: (85)..(85)
<223> OTHER INFORMATION: Xaa = any amino acid
<220> FEATURE:
<221> NAME/KEY: misc_feature
<222> LOCATION: (90)..(90)
<223> OTHER INFORMATION: Xaa = any amino acid
<220> FEATURE:
<221> NAME/KEY: misc_feature
<222> LOCATION: (94)..(94)
<223> OTHER INFORMATION: Xaa = any amino acid

<400> SEQUENCE: 20

Xaa Gln Xaa Gln Leu Val Gln Ser Gly Ala Glu Val Lys Lys Xaa Gly
1               5                   10                  15

Xaa Ser Val Lys Val Ser Cys Lys Ala Ser Gly Phe Asn Ile Lys Asp
            20                  25                  30

Tyr Tyr Leu His Trp Val Arg Gln Ala Pro Gly Gln Xaa Leu Glu Trp
        35                  40                  45

Met Gly Trp Ile Asp Pro Asp Gln Gly Asp Thr Glu Tyr Ala Gln Lys
    50                  55                  60

Xaa Gln Xaa Arg Val Thr Xaa Thr Xaa Asp Xaa Ser Xaa Ser Thr Ala
65                  70                  75                  80

Tyr Met Glu Leu Xaa Ser Leu Arg Ser Xaa Asp Thr Ala Xaa Tyr Tyr
                85                  90                  95

Cys Asn Ala Ala Tyr Gly Ser Ser Tyr Pro Met Asp Tyr Trp Gly
            100                 105                 110

Gln Gly Thr Thr Val Thr Val
        115

<210> SEQ ID NO 21
<211> LENGTH: 119
<212> TYPE: PRT
<213> ORGANISM: Artificial Sequence
<220> FEATURE:
<223> OTHER INFORMATION: anti-CD47 antibody VH - 13m

<400> SEQUENCE: 21

Met Gln Val Gln Leu Val Gln Ser Gly Ala Glu Val Lys Lys Pro Gly
1               5                   10                  15

Ala Ser Val Lys Val Ser Cys Lys Ala Ser Gly Phe Asn Ile Lys Asp
            20                  25                  30

Tyr Tyr Leu His Trp Val Arg Gln Ala Pro Gly Gln Gly Leu Glu Trp
        35                  40                  45
```

Met Gly Trp Ile Asp Pro Asp Gln Gly Asp Thr Glu Tyr Ala Gln Lys
            50                  55                  60

Leu Gln Gly Arg Val Thr Met Thr Thr Asp Thr Ser Thr Ser Thr Ala
 65                  70                  75                  80

Tyr Met Glu Leu Arg Ser Leu Arg Ser Asp Asp Thr Ala Val Tyr Tyr
                 85                  90                  95

Cys Asn Ala Ala Tyr Gly Ser Ser Ser Tyr Pro Met Asp Tyr Trp Gly
            100                 105                 110

Gln Gly Thr Thr Val Thr Val
        115

<210> SEQ ID NO 22
<211> LENGTH: 119
<212> TYPE: PRT
<213> ORGANISM: Artificial Sequence
<220> FEATURE:
<223> OTHER INFORMATION: anti-CD47 antibody VH - 5m

<400> SEQUENCE: 22

Met Gln Met Gln Leu Val Gln Ser Gly Ala Glu Val Lys Lys Pro Gly
 1               5                  10                  15

Ser Ser Val Lys Val Ser Cys Lys Ala Ser Gly Phe Asn Ile Lys Asp
            20                  25                  30

Tyr Tyr Leu His Trp Val Arg Gln Ala Pro Gly Gln Ala Leu Glu Trp
        35                  40                  45

Met Gly Trp Ile Asp Pro Asp Gln Gly Asp Thr Glu Tyr Ala Gln Lys
            50                  55                  60

Leu Gln Gly Arg Val Thr Met Thr Thr Asp Thr Ser Thr Ser Thr Ala
 65                  70                  75                  80

Tyr Met Glu Leu Arg Ser Leu Arg Ser Asp Asp Thr Ala Val Tyr Tyr
                 85                  90                  95

Cys Asn Ala Ala Tyr Gly Ser Ser Ser Tyr Pro Met Asp Tyr Trp Gly
            100                 105                 110

Gln Gly Thr Thr Val Thr Val
        115

<210> SEQ ID NO 23
<211> LENGTH: 1356
<212> TYPE: DNA
<213> ORGANISM: Artificial Sequence
<220> FEATURE:
<223> OTHER INFORMATION: Anti-CD47 antibody IgG1 heavy chain

<400> SEQUENCE: 23
atgcaaatgc aattggtaca aagcggtgcg gaagtaaaga aaacgggttc gtcggtaaag      60
gttagctgta aagcttctgg cttcaatatc aaggattact atctgcactg ggtgcgtcag     120
gcgccaggtc aggccttgga atggatgggc tggattgacc cggatcaagg tgacaccgaa     180
tatgcccaaa agtttcagga ccgtgtgacc atcacccgtg accgtagcat gtccaccgca     240
tatatggagc tgagcagcct gcgcagcgaa gatactgcga tgtattactg caatgcggcc     300
tatggtagca gctcctatcc gatggattac tggggccagg gtaccacggt gacggttagc     360
agcgcaagca ccaagggccc gagcgttttc cctctggcgc cgagcagcaa aagcactagc     420
ggcggtacgg cagccctggg ttgtctggtt aaagattact tcccggaacc ggttaccgtg     480
tcctggaact ctggcgcgct gaccagcggg gttcacacgt tccggcggt tctgcagagc     540 agcggtctgt attctttgag ctccgtcgtc accgtcccgt ctagctcgct gggcacgcag     600

| | |
|---|---:|
| acgtacatct gcaatgttaa ccataagccg agcaatacca aagttgacaa gaaagtcgaa | 660 |
| cctaagagct gtgataagac gcatacctgt ccgccgtgcc cggcaccgga actgttgggc | 720 |
| ggtccgagcg tgttcctgtt tccgccgaag ccgaaagata ccctgatgat tagccgcacc | 780 |
| cctgaggtga cgtgcgtggt tgtggacgtt agccatgagg atccagaggt caaattcaat | 840 |
| tggtatgtcg atggtgttga ggttcacaat gccaagacca accgcgtga agaacagtac | 900 |
| aatagcacct accgcgtggt gagcgtgctg acggtcctgc accaggactg gctgaacggc | 960 |
| aaagagtaca agtgtaaggt cagcaacaag gcgctgccag caccgattga aaagaccatt | 1020 |
| tctaaagcga aaggtcagcc gcgtgagccg caagtctata ccctgccgcc gtcgcgcgat | 1080 |
| gagctgacta aaaaccaggt tagcctgacg tgcctggtga aaggtttcta cccgagcgac | 1140 |
| atcgcggtgg agtgggagag caacggtcaa ccggagaata actacaaaac caccccaccg | 1200 |
| gtcttggact ccgatggcag cttctttctg tactctaaac tgaccgttga caaaagccgt | 1260 |
| tggcaacagg gcaacgtctt tagctgcagc gtgatgcatg aggctctgca caaccactac | 1320 |
| acccaaaaat ccctgagcct gagcccgggt aagtaa | 1356 |

<210> SEQ ID NO 24
<211> LENGTH: 1347
<212> TYPE: DNA
<213> ORGANISM: Artificial Sequence
<220> FEATURE:
<223> OTHER INFORMATION: Anti-CD47 antibody IgG4P heavy chain

<400> SEQUENCE: 24

| | |
|---|---:|
| atgcagatgc aattggttca aagcggtgcg gaagttaaga aaacgggttc gtcggtgaag | 60 |
| gtttcctgca agccagcggt ttttaacatc aaggattact atctgcattg gtacgtcag | 120 |
| gcaccgggtc aagcgttgga gtggatgggt tggatcgacc cggaccaggg tgatacggag | 180 |
| tatgcgcaga aattccagga ccgcgttacc atcacccgcg accgcagcat gagcacggcg | 240 |
| tacatggagc tgagcagcct gcgttccgaa gataccgcga tgtactactg taatgctgcg | 300 |
| tatggtagca gcagctatcc aatggactat tggggccagg gcacgacggt caccgttagc | 360 |
| agcgctagca ccaagggccc gtctgtgttt ccgttggcac cgtgcagccg tagcactagc | 420 |
| gaatccactg cagcgctggg ttgcctggtt aaggactatt tcccggagcc ggttaccgtg | 480 |
| tcctggaact ctggcgccct gaccagcggt gttcacacgt ttccagccgt cctgcagagc | 540 |
| agcggtctgt acagcctgag ctcggtggtg accgttccga gcagctctct gggtaccaaa | 600 |
| acctatacct gtaatgtcga tcacaaaccg tctaacacga aggtcgataa acgtgttgaa | 660 |
| agcaagtacg gtccgccttg tccgccgtgc ccggcaccgg agtttctggg cggtccgtcc | 720 |
| gtattcctgt tcccgccgaa accgaaagat accttgatga ttagccgtac gccagaggtc | 780 |
| acgtgcgtcg tggtggacgt tagccaagag gatccggaag tccaattcaa ctggtacgtg | 840 |
| gacggtgtcg aggtgcacaa tgccaaaacc aagccgcgtg aagaacagtt taacagcact | 900 |
| taccgcgtcg ttagcgtcct gaccgtgctg caccaagatt ggctgaatgg taaagagtac | 960 |
| aagtgcaagg ttagcaataa gggtctgccg agcagcatcg agaaaaccat tagcaaggcg | 1020 |
| aaaggtcaac cgcgcgagcc acaggtctac acgctgccgc cgagccaaga agaaatgacc | 1080 |
| aaaaatcagg ttagcctgac ttgtctggtg aaaggcttct acccgagcga tattgcagtt | 1140 |
| gaatgggaga gcaacggcca gcctgagaac aactataaga cgaccccgcc agtgctggac | 1200 |
| agcgatggca gcttcttttt gtattctcgt ctgaccgtgg acaagtcccg ttggcaagag | 1260 |

```
ggcaatgtgt tcagctgttc tgtcatgcac gaagcgctgc ataaccatta cacccagaag   1320
tccctgagcc tgtcgctggg caaataa                                       1347

<210> SEQ ID NO 25
<211> LENGTH: 1347
<212> TYPE: DNA
<213> ORGANISM: Artificial Sequence
<220> FEATURE:
<223> OTHER INFORMATION: Anti-CD47 antibody IgG4PE heavy chain

<400> SEQUENCE: 25
atgcagatgc aattggttca aagcggtgcg gaagttaaga aaacgggttc gtcggtgaag     60
gtttcctgca aagccagcgg ttttaacatc aaggattact atctgcattg ggtacgtcag    120
gcaccgggtc aagcgttgga gtggatgggt tggatcgacc cggaccaggg tgatacggag    180
tatgcgcaga attccagga ccgcgttacc atcacccgcg accgcagcat gagcacggcg     240
tacatggagc tgagcagcct gcgttccgaa gataccgcga tgtactactg taatgctgcg    300
tatggtagca gcagctatcc aatggactat tggggccagg gcacgacggt caccgttagc    360
agcgctagca ccaagggccc gtctgtgttt ccgttggcac cgtgcagccg tagcactagc    420
gaatccactg cagcgctggg ttgcctggtt aaggactatt cccggagcc ggttaccgtg     480 tcctggaact ctggcgccct gaccagcggg gttcacacgt ttccagccgt cctgcagagc    540
agcggtctgt acagcctgag ctcggtggtg accgttccga gcagctctct gggtaccaaa    600
acctatacct gtaatgtcga tcacaaaccg tctaacacga aggtcgataa acgtgttgaa    660
agcaagtacg gtccgccttg tccgccgtgc ccggcaccgg agtttgaggg cggtccgtcc    720
gtattcctgt tcccgccgaa accgaaagat accttgatga ttagccgtac gccagaggtc    780
acgtgcgtcg tggtggacgt tagccaagag gatccggaag tccaattcaa ctggtacgtg    840
gacggtgtcg aggtgcacaa tgccaaaacc aagccgcgtg aagaacagtt taacagcact    900
taccgcgtcg ttagcgtcct gaccgtgctg caccaagatt ggctgaatgg taaagagtac    960
aagtgcaagg ttagcaataa gggtctgccg agcagcatcg agaaaaccat tagcaaggcg   1020
aaaggtcaac cgcgcgagcc acaggtctac acgctgccgc cgagccaaga agaaatgacc   1080
aaaaatcagg ttagcctgac ttgtctggtg aaaggcttct acccgagcga tattgcagtt   1140
gaatgggaga gcaacggcca gcctgagaac aactataaga cgaccccgcc agtgctggac   1200
agcgatggca gcttcttttt gtattctcgt ctgaccgtgg acaagtcccg ttggcaagag   1260
ggcaatgtgt tcagctgttc tgtcatgcac gaagcgctgc ataaccatta cacccagaag   1320
tccctgagcc tgtcgctggg caaataa                                       1347

<210> SEQ ID NO 26
<211> LENGTH: 1356
<212> TYPE: DNA
<213> ORGANISM: Artificial Sequence
<220> FEATURE:
<223> OTHER INFORMATION: Anti-CD47 antibody IgG1-13m heavy chain

<400> SEQUENCE: 26
atgcaagtcc aattggtcca gagcggtgcg gaagtcaaga aaccgggtgc aagcgtcaaa     60
gtttcgtgca aggcgagcgg tttcaatatc aaagactatt atctgcactg ggttcgtcag    120
gctccgggcc aaggcctgga gtggatgggt tggatcgatc cggaccaggg cgacacggag    180
tacgctcaga agctgcaggg tcgtgttacc atgaccaccg acaccagcac gagcaccgcg    240
tacatggaac tgcgctctct gcgttcggat gataccgcgg tgtactattg caacgccgcg    300
```

| | |
|---|---|
| tacggtagca gcagctatcc gatggattat tggggtcaag cactacggt gactgtcagc | 360 |
| agcgccagca ccaagggccc gtccgtgttt ccgctggcgc aagctccaa gagcaccagc | 420 |
| ggtggcacgg ccgcactggg ttgtctggta aagattact ttcctgagcc ggtgaccgtg | 480 |
| agctggaatt caggtgcact gacgtccggc gttcacacgt tcccggcagt tctgcagagc | 540 |
| tccggtttgt acagcctgtc tagcgtcgtg acggtgccga gcagcagcct gggtacccaa | 600 |
| acctacattt gcaacgttaa ccataagccg agcaatacca aagttgacaa gaaagtcgaa | 660 |
| cctaagagct gtgataagac gcatacctgt ccgccgtgcc cggcaccgga actgttgggc | 720 |
| ggtccgagcg tgttcctgtt tccgccgaag ccgaaagata ccctgatgat tagccgcacc | 780 |
| cctgaggtga cgtgcgtggt tgtggacgtt agccatgagg atccagaggt caaattcaat | 840 |
| tggtatgtcg atggtgttga ggttcacaat gccaagacca accgcgtga agaacagtac | 900 |
| aatagcacct accgcgtggt gagcgtgctg acggtcctgc accaggactg gctgaacggc | 960 |
| aaagagtaca gtgtaaggt cagcaacaag gcgctgccag caccgattga aaagaccatt | 1020 |
| tctaaagcga aaggtcagcc gcgtgagccg caagtctata ccctgccgcc gtcgcgcgat | 1080 |
| gagctgacta aaaaccaggt tagcctgacg tgcctggtga aggtttcta cccgagcgac | 1140 |
| atcgcggtgg agtgggagag caacggtcaa ccggagaata actacaaaac cacccaccg | 1200 |
| gtcttggact ccgatggcag cttctttctg tactctaaac tgaccgttga caaaagccgt | 1260 |
| tggcaacagg gcaacgtctt tagctgcagc gtgatgcatg aggctctgca caaccactac | 1320 |
| acccaaaaat ccctgagcct gagcccgggt aagtaa | 1356 |

<210> SEQ ID NO 27
<211> LENGTH: 1356
<212> TYPE: DNA
<213> ORGANISM: Artificial Sequence
<220> FEATURE:
<223> OTHER INFORMATION: Anti-CD47 antibody IgG1-13mZ heavy chain

<400> SEQUENCE: 27

| | |
|---|---|
| atgcaagtcc aattggtcca gagcggtgcg gaagtcaaga accgggtgc aagcgtcaaa | 60 |
| gtttcgtgca aggcgagcgg tttcaatatc aaagactatt atctgcactg ggttcgtcag | 120 |
| gctccgggcc aaggcctgga gtggatgggt tggatcgatc cggaccaggg cgacacggag | 180 |
| tacgctcaga agctgcaggg tcgtgttacc atgaccaccg acaccagcac gagcaccgcg | 240 |
| tacatggaac tgcgctctct gcgttcggat gataccgcgg tgtactattg caacgccgcg | 300 |
| tacggtagca gcagctatcc gatggattat tggggtcaag cactacggt gactgtcagc | 360 |
| agcgccagca ccaagggccc gtccgtgttt ccgctggcgc aagctccaa gagcaccagc | 420 |
| ggtggcacgg ccgcactggg ttgtctggta aagattact ttcctgagcc ggtgaccgtg | 480 |
| agctggaatt caggtgcact gacgtccggc gttcacacgt tcccggcagt tctgcagagc | 540 |
| tccggtttgt acagcctgtc tagcgtcgtg acggtgccga gcagcagcct gggtacccaa | 600 |
| acctacattt gcaacgttaa ccataagccg agcaatacca aggttgacaa aaagttgaa | 660 |
| ccgaaatctt gtgataaaac tcatacctgt ccgccgtgcc ggcgcctga gctgttgggt | 720 |
| ggtccgtcgg tctttctgtt cccgccgaag ccgaaagaca ccctgatgat tagccgcacc | 780 |
| ccggaagtta cgtgcgtcgt cgtggatgtc agccacgagg acccggaggt taagttcaat | 840 |
| tggtatgtcg atggcgttga ggttcacaac gcgaaaacca gccgcgtga ggaacaatac | 900 |
| aatagcacgt atcgcgtagt gagcgtgctg acgtgctgc accaagattg gctgaatggt | 960 |
| aaagaataca gtgcaaagt gagcaacaag gcattgccgg caccgatcga aaagacgatc | 1020 |

```
agcaaagcga aaggccaacc gcgtgaaccg caggtctata ccctgccgcc gagccgtgaa    1080
gaaatgacga aaaaccaagt tagcctgacc tgtctggtga agggcttttta cccgagcgac   1140 atcgccgtcg agtgggagtc taacggccag ccggaaaaca attacaaaac cacgccgcca    1200
gtcctggaca gcgacggtag cttctttctg tatagcaagc tgaccgtcga taaaagccgt    1260
tggcagcagg gtaatgtgtt cagctgcagc gttatgcatg aggcgctgca caatcactat    1320
acccagaaat ccttgtccct gtccccgggt aagtaa                              1356

<210> SEQ ID NO 28
<211> LENGTH: 1356
<212> TYPE: DNA
<213> ORGANISM: Artificial Sequence
<220> FEATURE:
<223> OTHER INFORMATION: Anti-CD47 antibody IgG1-5m heavy chain

<400> SEQUENCE: 28
atgcaaatgc aattggtaca aagcggtgcg gaagtaaaga aaccggggttc gtcggtaaag     60 gttagctgta aagcttctgg cttcaatatc aaggattact atctgcactg ggtgcgtcag    120
gcgccaggtc aggccttgga atggatgggc tggattgacc cggatcaagg tgacaccgaa    180
tatgcccaaa agtttcaggg tcgtgtgacc atcacccgtg accgtagcac ctccaccgca    240
tatatggagc tgcgtagcct gcgcagcgaa gatactgcgg tgtattactg caatgcggcc    300
tatggtagca gctcctatcc gatggattac tggggccagg gtaccacggt gacggttagc    360
agcgcaagca ccaagggccc gagcgttttc cctctggcgc cgagcagcaa agcactagc    420 ggcggtacgg cagccctggg ttgtctggtt aaagattact tccggaacc ggttaccgtg    480 tcctggaact ctggcgcgct gaccagcggt gttcacacgt tccggcggt tctgcagagc    540 agcggtctgt attctttgag ctccgtcgtc accgtcccgt ctagctcgct gggcacgcag    600
acgtacatct gcaatgttaa ccataagccg agcaatacca agttgacaa gaaagtcgaa    660 cctaagagct gtgataagac gcatacctgt ccgccgtgcc cggccaccgga actgttgggc    720 ggtccgagcg tgttcctgtt ccgccgaag ccgaaagata ccctgatgat tagccgcacc    780
cctgaggtga cgtgcgtggt tgtggacgtt agccatgagg atccagaggt caaattcaat    840
tggtatgtcg atggtgttga ggttcacaat gccaagacca accgcgtga agaacagtac    900 aatagcacct accgcgtggt gagcgtgctg acggtcctgc accaggactg gctgaacggc    960
aaagagtaca agtgtaaggt cagcaacaag gcgctgccag caccgattga aaagaccatt   1020
tctaaagcga aaggtcagcc gcgtgagccg caagtctata ccctgccgcc gtcgcgcgat   1080
gagctgacta aaaaccaggt tagcctgacg tgcctggtga aggtttcta cccgagcgac   1140 atcgcggtgg agtgggagag caacggtcaa ccggagaata actacaaaac cacccccaccg   1200 gtcttggact ccgatggcag cttctttctg tactctaaac tgaccgttga caaaagccgt   1260
tggcaacagg gcaacgtctt tagctgcagc gtgatgcatg aggctctgca caaccactac   1320
acccaaaaat ccctgagcct gagcccgggt aagtaa                              1356

<210> SEQ ID NO 29
<211> LENGTH: 1347
<212> TYPE: DNA
<213> ORGANISM: Artificial Sequence
<220> FEATURE:
<223> OTHER INFORMATION: Anti-CD47 antibody IgG4P-13m heavy chain
```

<400> SEQUENCE: 29

```
atgcaagtcc aattggtcca gagcggtgcg gaagtcaaga aaccgggtgc aagcgtcaaa        60
gtttcgtgca aggcgagcgg tttcaatatc aaagactatt atctgcactg ggttcgtcag       120
gctccgggcc aaggcctgga gtggatgggt tggatcgatc cggaccaggg cgacacggag       180
tacgctcaga agctgcaggg tcgtgttacc atgaccaccg acaccagcac gagcaccgcg       240
tacatggaac tgcgctctct gcgttcggat gataccgcgg tgtactattg caacgccgcg       300
tacggtagca gcagctatcc gatggattat tggggtcaag gcactacggt gactgtcagc       360
agcgccagca ccaagggccc gtctgtgttt ccgttggcac cgtgcagccg tagcactagc       420
gaatccactg cagcgctggg ttgcctggtt aaggactatt tcccggagcc ggttaccgtg       480
tcctggaact ctggcgccct gaccagcggg gttcacacgt ttccagccgt cctgcagagc       540
agcggtctgt acagcctgag ctcggtggtg accgttccga gcagctctct gggtaccaaa       600
acctatacct gtaatgtcga tcacaaaccg tctaacacga aggtcgataa acgtgttgaa       660
agcaagtacg gtccgccttg tccgccgtgc ccggcaccgg agtttctggg cggtccgtcc       720
gtattcctgt tcccgccgaa accgaaagat accttgatga ttagccgtac gccagaggtc       780
acgtgcgtcg tggtggacgt tagccaagag gatccggaag tccaattcaa ctggtacgtg       840
gacggtgtcg aggtgcacaa tgccaaaacc aagccgcgtg aagaacagtt taacagcact       900
taccgcgtcg ttagcgtcct gaccgtgctg caccaagatt ggctgaatgg taaagagtac       960
aagtgcaagg ttagcaataa gggtctgccg agcagcatcg agaaaaccat tagcaaggcg      1020
aaaggtcaac cgcgcgagcc acaggtctac acgctgccgc cgagccaaga agaaatgacc      1080
aaaaatcagg ttagcctgac ttgtctggtg aaaggcttct acccgagcga tattgcagtt      1140
gaatgggaga gcaacggcca gcctgagaac aactataaga cgaccccgcc agtgctggac      1200
agcgatggca gcttcttttt gtattctcgt ctgaccgtgg acaagtcccg ttggcaagag      1260
ggcaatgtgt tcagctgttc tgtcatgcac gaagcgctgc ataaccatta cacccagaag      1320
tccctgagcc tgtcgctggg caaataa                                          1347
```

<210> SEQ ID NO 30
<211> LENGTH: 1347
<212> TYPE: DNA
<213> ORGANISM: Artificial Sequence
<220> FEATURE:
<223> OTHER INFORMATION: Anti-CD47 antibody IgG4P-5m heavy chain

<400> SEQUENCE: 30

```
atgcaaatgc aattggtaca aagcggtgcg gaagtaaaga aaccgggttc gtcggtaaag        60
gttagctgta agcttctggc ttcaatatc aaggattact atctgcactg ggtgcgtcag       120
gcgccaggtc aggccttgga atggatgggc tggattgacc cggatcaagg tgacaccgaa       180
tatgcccaaa agtttcaggg tcgtgtgacc atcacccgtg accgtagcac ctccaccgca       240
tatatggagc tgcgtagcct gcgcagcgaa gatactgcgg tgtattactg caatgcggcc       300
tatggtagca gctcctatcc gatggattac tggggccagg gtaccacggt gacggttagc       360
agcgcaagca ccaagggccc gtctgtgttt ccgttggcac cgtgcagccg tagcactagc       420
gaatccactg cagcgctggg ttgcctggtt aaggactatt tcccggagcc ggttaccgtg       480
tcctggaact ctggcgccct gaccagcggg gttcacacgt ttccagccgt cctgcagagc       540
agcggtctgt acagcctgag ctcggtggtg accgttccga gcagctctct gggtaccaaa       600
acctatacct gtaatgtcga tcacaaaccg tctaacacga aggtcgataa acgtgttgaa       660
```

```
agcaagtacg gtccgccttg tccgccgtgc ccggcaccgg agtttctggg cggtccgtcc    720
gtattcctgt tcccgccgaa accgaaagat accttgatga ttagccgtac gccagaggtc    780
acgtgcgtcg tggtggacgt tagccaagag gatccggaag tccaattcaa ctggtacgtg    840
gacggtgtcg aggtgcacaa tgccaaaacc aagccgcgtg aagaacagtt taacagcact    900
taccgcgtcg ttagcgtcct gaccgtgctg caccaagatt ggctgaatgg taaagagtac    960
aagtgcaagg ttagcaataa gggtctgccg agcagcatcg agaaaaccat tagcaaggcg   1020
aaaggtcaac cgcgcgagcc acaggtctac acgctgccgc cgagccaaga agaaatgacc   1080
aaaaatcagg ttagcctgac ttgtctggtg aaaggcttct acccgagcga tattgcagtt   1140
gaatgggaga gcaacggcca gcctgagaac aactataaga cgaccccgcc agtgctggac   1200
agcgatggca gcttctttttt gtattctcgt ctgaccgtgg acaagtcccg ttggcaagag   1260
ggcaatgtgt tcagctgttc tgtcatgcac gaagcgctgc ataaccatta cacccagaag   1320
tccctgagcc tgtcgctggg caaataa                                       1347
```

```
<210> SEQ ID NO 31
<211> LENGTH: 1347
<212> TYPE: DNA
<213> ORGANISM: Artificial Sequence
<220> FEATURE:
<223> OTHER INFORMATION: Anti-CD47 antibody IgG4PE-13m heavy chain

<400> SEQUENCE: 31
atgcaagtcc aattggtcca gagcggtgcg gaagtcaaga aaccgggtgc aagcgtcaaa     60
gtttcgtgca aggcgagcgg tttcaatatc aaagactatt atctgcactg ggttcgtcag    120
gctccgggcc aaggcctgga gtggatgggt tggatcgatc cggaccaggg cgacacggag    180
tacgctcaga agctgcaggg tcgtgttacc atgaccaccg acaccagcac gagcaccgcg    240
tacatggaac tgcgctctct gcgttcggat gataccgcgg tgtactattg caacgccgcg    300
tacggtagca gcagctatcc gatggattat tggggtcaag gcactacggt gactgtcagc    360
agcgccagca ccaagggccc gtctgtgttt ccgttggcac cgtgcagccg tagcactagc    420
gaatccactg cagcgctggg ttgcctggtt aaggactatt tcccggagcc ggttaccgtg    480
tcctggaact ctggcgccct gaccagcggt gttcacacgt ttccagccgt cctgcagagc    540
agcggtctgt acagcctgag ctcggtggtg accgttccga gcagctctct gggtaccaaa    600
acctatacct gtaatgtcga tcacaaaccg tctaacacga aggtcgataa acgtgttgaa    660
agcaagtacg gtccgccttg tccgccgtgc ccggcaccgg agtttgaggg cggtccgtcc    720
gtattcctgt tcccgccgaa accgaaagat accttgatga ttagccgtac gccagaggtc    780
acgtgcgtcg tggtggacgt tagccaagag gatccggaag tccaattcaa ctggtacgtg    840
gacggtgtcg aggtgcacaa tgccaaaacc aagccgcgtg aagaacagtt taacagcact    900
taccgcgtcg ttagcgtcct gaccgtgctg caccaagatt ggctgaatgg taaagagtac    960
aagtgcaagg ttagcaataa gggtctgccg agcagcatcg agaaaaccat tagcaaggcg   1020
aaaggtcaac cgcgcgagcc acaggtctac acgctgccgc cgagccaaga agaaatgacc   1080
aaaaatcagg ttagcctgac ttgtctggtg aaaggcttct acccgagcga tattgcagtt   1140
gaatgggaga gcaacggcca gcctgagaac aactataaga cgaccccgcc agtgctggac   1200
agcgatggca gcttctttttt gtattctcgt ctgaccgtgg acaagtcccg ttggcaagag   1260
ggcaatgtgt tcagctgttc tgtcatgcac gaagcgctgc ataaccatta cacccagaag   1320
tccctgagcc tgtcgctggg caaataa                                       1347
```

<210> SEQ ID NO 32
<211> LENGTH: 1347
<212> TYPE: DNA
<213> ORGANISM: Artificial Sequence
<220> FEATURE:
<223> OTHER INFORMATION: Anti-CD47 antibody IgG4PE-5m heavy chain

<400> SEQUENCE: 32

```
atgcaaatgc aattggtaca aagcggtgcg gaagtaaaga accgggttc gtcggtaaag      60
gttagctgta aagcttctgg cttcaatatc aaggattact atctgcactg ggtgcgtcag     120
gcgccaggtc aggccttgga atggatgggc tggattgacc cggatcaagg tgacaccgaa     180
tatgcccaaa agtttcaggg tcgtgtgacc atcacccgtg accgtagcac ctccaccgca     240
tatatggagc tgcgtagcct gcgcagcgaa gatactgcgg tgtattactg caatgcggcc     300
tatggtagca gctcctatcc gatggattac tggggccagg gtaccacggt gacggttagc     360
agcgcaagca ccaagggccc gtctgtgttt ccgttggcac cgtgcagccg tagcactagc     420
gaatccactg cagcgctggg ttgcctggtt aaggactatt cccggagcc ggttaccgtg     480
tcctggaact ctggcgccct gaccagcggt gttcacacgt tccagccgt cctgcagagc     540
agcggtctgt acagcctgag ctcggtggtg accgttccga gcagctctct gggtaccaaa     600
acctatacct gtaatgtcga tcacaaaccg tctaacacga aggtcgataa acgtgttgaa     660
agcaagtacg gtccgccttg tccgccgtgc ccggcaccgg agtttgaggg cggtccgtcc     720
gtattcctgt tcccgccgaa accgaaagat accttgatga ttagccgtac gccagaggtc     780
acgtgcgtcg tggtggacgt tagccaagag gatccggaag tccaattcaa ctggtacgtg     840
gacggtgtcg aggtgcacaa tgccaaaacc aagccgcgtg aagaacagtt taacagcact     900
taccgcgtcg ttagcgtcct gaccgtgctg caccaagatt ggctgaatgg taaagagtac     960
aagtgcaagg ttagcaataa gggtctgccg agcagcatcg agaaaaccat tagcaaggcg    1020
aaaggtcaac cgcgcgagcc acaggtctac acgctgccgc cgagccaaga agaaatgacc    1080
aaaaatcagg ttagcctgac ttgtctggtg aaaggcttct acccgagcga tattgcagtt    1140
gaatgggaga gcaacggcca gcctgagaac aactataaga cgaccccgcc agtgctggac    1200
agcgatggca gcttctttt gtattctcgt ctgaccgtgg acaagtcccg ttggcaagag    1260
ggcaatgtgt tcagctgttc tgtcatgcac gaagcgctgc ataaccatta cacccagaag    1320
tccctgagcc tgtcgctggg caaataa                                        1347
```

<210> SEQ ID NO 33
<211> LENGTH: 648
<212> TYPE: DNA
<213> ORGANISM: Artificial Sequence
<220> FEATURE:
<223> OTHER INFORMATION: Anti-CD47 antibody (Igk) light chain

<400> SEQUENCE: 33

```
atgaacatcc aaatgactca atccccatcc gcaatgtccg catccgtagg tgaccgcgtg      60
accatcacgt gcaaggcgag ccaggatatt catcgttatc tgagctggtt tcaacagaaa     120
ccgggcaagg ttcctaagca tctgatttac cgcgcgaacc gcttggttag cggtgttccg     180
agccgtttta gcggcagcgg ttctggcacc gagttcaccc tgacgatctc cagcctgcaa     240
ccggaagatt ttgcgacgta ctactgcctg cagtatgacg agttcccgta cctttggt      300
ggtggtacga aggtggaaat caaacgtact gtggccgctc cgagcgtttt cattttccg      360
ccgtcggatg agcaattgaa atctggtacc gcgagcgtcg tttgtctgct gaacaatttc     420
```

```
tacccgcgtg aggctaaggt gcaatggaag gtcgataacg cgctgcagag cggtaatagc      480
caggaaagcg tcaccgaaca ggatagcaaa gacagcacct actctttgag cagcaccctg      540
accctgagca aggccgacta tgagaaacac aaagtttacg catgtgaggt cacgcaccag      600
ggcctgagca gcccggtgac caaaagcttc aatcgtggcg aatgctaa                   648
```

<210> SEQ ID NO 34
<211> LENGTH: 330
<212> TYPE: PRT
<213> ORGANISM: Homo sapiens
<220> FEATURE:
<223> OTHER INFORMATION: human IgG1 isotype

<400> SEQUENCE: 34

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 35
<211> LENGTH: 326
<212> TYPE: PRT
<213> ORGANISM: Homo sapiens
<220> FEATURE:
<223> OTHER INFORMATION: human IgG2 isotype

<400> SEQUENCE: 35

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 36
<211> LENGTH: 377
<212> TYPE: PRT
<213> ORGANISM: Homo sapiens
<220> FEATURE:
<223> OTHER INFORMATION: human IgG3 isotype

<400> SEQUENCE: 36

```
Ala Ser Thr Lys Gly Pro Ser Val Phe Pro Leu Ala Pro Cys Ser Arg
1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350
```

```
Phe Ser Cys Ser Val Met His Glu Ala Leu His Asn Arg Phe Thr Gln
            355                 360                 365

Lys Ser Leu Ser Leu Ser Pro Gly Lys
            370                 375

<210> SEQ ID NO 37
<211> LENGTH: 327
<212> TYPE: PRT
<213> ORGANISM: Homo sapiens
<220> FEATURE:
<223> OTHER INFORMATION: human IgG4 isotype

<400> SEQUENCE: 37

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 38
<211> LENGTH: 323
<212> TYPE: PRT
<213> ORGANISM: Homo sapiens
<220> FEATURE:
<223> OTHER INFORMATION: exemplary human CD47 (GenBank Accession No.
      Q08722.1 (GI:1171879))

<400> SEQUENCE: 38

Met Trp Pro Leu Val Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Lys
    290                 295                 300

Ala Val Glu Glu Pro Leu Asn Ala Phe Lys Glu Ser Lys Gly Met Met
305                 310                 315                 320

Asn Asp Glu

<210> SEQ ID NO 39
<211> LENGTH: 305
<212> TYPE: PRT
<213> ORGANISM: Homo sapiens
<220> FEATURE:
<223> OTHER INFORMATION: exemplary human CD47 excluding signal sequence

```
<400> SEQUENCE: 39

Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
                20                  25                  30

Thr Thr Glu Val Tyr Val Lys Trp Lys Phe Lys Gly Arg Asp Ile Tyr
            35                  40                  45

Thr Phe Asp Gly Ala Leu Asn Lys Ser Thr Val Pro Thr Asp Phe Ser
    50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
            100                 105                 110

Tyr Arg Val Val Ser Trp Phe Ser Pro Asn Glu Asn Ile Leu Ile Val
            115                 120                 125

Ile Phe Pro Ile Phe Ala Ile Leu Leu Phe Trp Gly Gln Phe Gly Ile
    130                 135                 140

Lys Thr Leu Lys Tyr Arg Ser Gly Gly Met Asp Glu Lys Thr Ile Ala
145                 150                 155                 160

Leu Leu Val Ala Gly Leu Val Ile Thr Val Ile Val Ile Val Gly Ala
                165                 170                 175

Ile Leu Phe Val Pro Gly Glu Tyr Ser Leu Lys Asn Ala Thr Gly Leu
            180                 185                 190

Gly Leu Ile Val Thr Ser Thr Gly Ile Leu Ile Leu Leu His Tyr Tyr
            195                 200                 205

Val Phe Ser Thr Ala Ile Gly Leu Thr Ser Phe Val Ile Ala Ile Leu
    210                 215                 220

Val Ile Gln Val Ile Ala Tyr Ile Leu Ala Val Val Gly Leu Ser Leu
225                 230                 235                 240

Cys Ile Ala Ala Cys Ile Pro Met His Gly Pro Leu Leu Ile Ser Gly
                245                 250                 255

Leu Ser Ile Leu Ala Leu Ala Gln Leu Leu Gly Leu Val Tyr Met Lys
            260                 265                 270

Phe Val Ala Ser Asn Gln Lys Thr Ile Gln Pro Pro Arg Lys Ala Val
            275                 280                 285

Glu Glu Pro Leu Asn Ala Phe Lys Glu Ser Lys Gly Met Met Asn Asp
    290                 295                 300

Glu
305
```